United States Patent
Roquet et al.

(10) Patent No.: US 11,306,353 B2
(45) Date of Patent: Apr. 19, 2022

(54) PROGRAMS AND FUNCTIONS IN DNA-BASED DATA STORAGE

(71) Applicant: CATALOG TECHNOLOGIES, INC., Charlestown, MA (US)

(72) Inventors: Nathaniel Roquet, Charlestown, MA (US); Swapnil P. Bhatia, Charlestown, MA (US); Michael Norsworthy, Charlestown, MA (US); Sarah Flickinger, Charlestown, MA (US); Tracy Kambara, Charlestown, MA (US)

(73) Assignee: CATALOG TECHNOLOGIES, INC., Charlestown, MA (US)

( * ) Notice: Subject to any disclaimer, the term of this patent is extended or adjusted under 35 U.S.C. 154(b) by 0 days.

(21) Appl. No.: 17/317,547

(22) Filed: May 11, 2021

(65) Prior Publication Data

US 2021/0348214 A1   Nov. 11, 2021

Related U.S. Application Data

(60) Provisional application No. 63/023,071, filed on May 11, 2020, provisional application No. 63/023,342, filed on May 12, 2020, provisional application No. 63/066,628, filed on Aug. 17, 2020, provisional application No. 63/165,559, filed on Mar. 24, 2021.

(51) Int. Cl.
| | | |
|---|---|---|
| *C12Q 1/686* | (2018.01) |
| *G16B 30/00* | (2019.01) |
| *C12Q 1/6813* | (2018.01) |
| *G06N 3/12* | (2006.01) |
| *G06F 3/06* | (2006.01) |

(52) U.S. Cl.
CPC ........... *C12Q 1/686* (2013.01); *C12Q 1/6813* (2013.01); *G06N 3/123* (2013.01); *G16B 30/00* (2019.02); *G06F 3/06* (2013.01)

(58) Field of Classification Search
CPC ...... C12Q 1/686; C12Q 1/6813; G06N 3/123; G16B 30/00; G06F 3/06
See application file for complete search history.

(56) References Cited

U.S. PATENT DOCUMENTS

| | | |
|---|---|---|
| 6,187,537 B1 | 2/2001 | Zinn, Jr. et al. |
| 6,221,653 B1 | 4/2001 | Caren et al. |
| 6,309,828 B1 | 10/2001 | Schleifer et al. |
| 6,384,210 B1 | 5/2002 | Blanchard |
| 6,419,883 B1 | 7/2002 | Blanchard |
| 6,446,642 B1 | 9/2002 | Caren et al. |
| 6,458,583 B1 | 10/2002 | Bruhn et al. |
| 6,537,747 B1 | 3/2003 | Mills, Jr. et al. |
| 6,796,634 B2 | 9/2004 | Caren et al. |
| 7,176,297 B2 | 2/2007 | Li et al. |
| 7,306,316 B2 | 12/2007 | Doak |
| 7,491,422 B2 | 2/2009 | Zhang et al. |
| 7,600,840 B2 | 10/2009 | Kim et al. |
| 7,802,517 B2 | 9/2010 | Wessels et al. |
| 7,833,701 B2 | 11/2010 | Oshima |
| 7,909,427 B2 | 3/2011 | Kim et al. |
| 7,951,334 B2 | 5/2011 | Mirkin et al. |
| 8,071,168 B2 | 12/2011 | Cruchon-Dupeyrat et al. |
| 8,114,207 B2 | 2/2012 | Josten |
| 8,136,936 B2 | 3/2012 | Hook et al. |
| 8,496,326 B2 | 7/2013 | Hook et al. |
| 8,735,327 B2 | 5/2014 | Macula |
| 8,769,689 B2 | 7/2014 | Hoglund |
| 8,806,127 B2 | 8/2014 | Brownell et al. |
| 8,856,940 B2 | 10/2014 | Kencl et al. |
| 8,937,564 B2 | 1/2015 | Aloni et al. |
| 9,061,494 B2 | 6/2015 | Rogers et al. |
| 9,062,218 B2 | 6/2015 | Oshima et al. |
| 9,187,777 B2 | 11/2015 | Jacobson et al. |
| 9,266,370 B2 | 2/2016 | Jung et al. |
| 9,317,664 B2 | 4/2016 | Ahuja et al. |
| 9,384,320 B2 | 7/2016 | Church |
| 9,403,180 B2 | 8/2016 | Ha et al. |
| 9,487,002 B2 | 11/2016 | Rogers et al. |
| 9,616,661 B2 | 4/2017 | Pierik et al. |

(Continued)

FOREIGN PATENT DOCUMENTS

| | | |
|---|---|---|
| EP | 1512749 A2 | 3/2005 |
| EP | 2329425 A1 | 6/2011 |

(Continued)

OTHER PUBLICATIONS

Lee et al, DNA detection using commercial mobile phones, Biosensors and Bioelectronics, 2011, 26, 4349-4354 (Year: 2011).*
Bonnet et al., "Rewritable digital data storage in live cells via engineered control of recombination directionality," Proceeding of the National Academy of Sciences, vol. 109(23): 8884-8889 (2012).
Bornholt et al., "A DNA-Based Archival Storage System," International Conference on Architectural Support for Programming Languages and Operating Systems (ASPLOS), Apr. 2-6, 2016, Atlanta, GA, 637-649.
Buschmann, et al., "Levenshtein Error-Correcting Barcodes for Multiplexed DNA Sequencing", BMC Bioinformatics, vol. 14, No. 1., pp. 1-10 (2013).
Bystrykh, et al., "Generalized DNA Barcode Design Based on Hamming Codes", PLOS ONE, vol. 7, No. 5, pp. 1-8, (May 2012).
Casini, A. "Advanced DNA assembly strategies and standards for synthetic biology," Thesis, Department of Life Sciences, Imperial College London: 1-178 (2014).

(Continued)

*Primary Examiner* — Narayan K Bhat
(74) *Attorney, Agent, or Firm* — White & Case LLP

(57) ABSTRACT

Systems and methods are provided herein for encoding and storing information in nucleic acids. Encoded information is partitioned and stored in nucleic acids having native key-value pairs that allow for storage of metadata or other data objects. Computation on the encoded information is performed by chemical implementation of if-then-else operations. Numerical data is stored in nucleic acids by producing samples having nucleic acid sequences copy counts corresponding to the numerical data. Data objects of a dataset are encoded by partitioning of bytes into parts and encoding of parts along distinct libraries of nucleic acids. These libraries can be used as inputs for computation on the dataset.

16 Claims, 26 Drawing Sheets

(56) References Cited

U.S. PATENT DOCUMENTS

| | | |
|---|---|---|
| 9,679,030 B2 | 6/2017 | Hatami-Hanza |
| 9,684,678 B2 | 6/2017 | Hatami-Hanza |
| 9,774,351 B2 | 9/2017 | Huetter et al. |
| 9,830,553 B2 | 11/2017 | Chen et al. |
| 9,904,734 B2 | 2/2018 | Murrah et al. |
| 9,928,869 B2 | 3/2018 | Church |
| 9,996,778 B2 | 6/2018 | Church |
| 10,020,826 B2 | 7/2018 | Gladwin et al. |
| 10,027,347 B2 | 7/2018 | Le Scouarnec et al. |
| 10,047,235 B2 | 8/2018 | Wilsher et al. |
| 10,050,959 B2 | 8/2018 | Soon-Shiong et al. |
| 10,287,573 B2 | 5/2019 | Macula |
| 10,289,801 B2 | 5/2019 | Church |
| 10,370,246 B1 | 8/2019 | Milenkovic et al. |
| 10,387,301 B2 | 8/2019 | Goldman et al. |
| 10,417,457 B2 | 9/2019 | Peck |
| 10,423,341 B1 | 9/2019 | Kermani |
| 10,438,662 B2 | 10/2019 | Predki |
| 10,460,220 B2 | 10/2019 | Church |
| 10,566,077 B1 | 2/2020 | Milenkovic et al. |
| 10,640,822 B2 | 5/2020 | Predki et al. |
| 10,650,312 B2 | 5/2020 | Roquet et al. |
| 10,669,558 B2 | 6/2020 | Ganjam |
| 10,742,233 B2 | 8/2020 | Erlich |
| 10,754,994 B2 | 8/2020 | Peck |
| 10,774,379 B2 | 9/2020 | Chen et al. |
| 10,787,699 B2 | 9/2020 | Chen et al. |
| 10,793,897 B2 | 10/2020 | Chen et al. |
| 10,818,378 B2 | 10/2020 | Hutchison, III et al. |
| 10,838,939 B2 | 11/2020 | Walder et al. |
| 10,839,295 B2 | 11/2020 | Shen et al. |
| 10,853,244 B2 | 12/2020 | Petti et al. |
| 10,883,140 B2 | 1/2021 | Church et al. |
| 10,902,939 B2 | 1/2021 | Merriman et al. |
| 10,917,109 B1 | 2/2021 | Dimopoulou et al. |
| 10,929,039 B2 | 2/2021 | Kwon et al. |
| 10,936,953 B2 | 3/2021 | Peck et al. |
| 10,956,806 B2 | 3/2021 | Masuda et al. |
| 2003/0116630 A1 | 6/2003 | Carey et al. |
| 2004/0244623 A1 | 12/2004 | Hayashizaki |
| 2005/0019760 A1 | 1/2005 | Southern |
| 2005/0166782 A2 | 8/2005 | Hayashizaki |
| 2005/0243618 A1 | 11/2005 | Boland et al. |
| 2006/0263534 A1 | 11/2006 | Laurent et al. |
| 2008/0252679 A1 | 10/2008 | Pierik et al. |
| 2008/0269152 A1 | 10/2008 | Verdine et al. |
| 2008/0303870 A1 | 12/2008 | Verbeek et al. |
| 2008/0309701 A1 | 12/2008 | Pierik et al. |
| 2009/0023607 A1 | 1/2009 | Rozhok et al. |
| 2009/0033690 A1 | 2/2009 | Pierik et al. |
| 2009/0062129 A1 | 3/2009 | McKernan et al. |
| 2009/0253141 A1 | 10/2009 | Quake |
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2013/0233709 A1 | 9/2013 | Dunbar et al. |
| 2014/0065609 A1 | 3/2014 | Hicks et al. |
| 2014/0296087 A1 | 10/2014 | Verdine et al. |
| 2014/0371100 A1 | 12/2014 | Kawashima et al. |
| 2015/0083797 A1 | 3/2015 | Tran et al. |
| 2015/0261664 A1 | 9/2015 | Goldman et al. |
| 2015/0269313 A1 | 9/2015 | Church |
| 2015/0312212 A1 | 10/2015 | Holmes et al. |
| 2015/0363550 A1 | 12/2015 | Green et al. |
| 2016/0007893 A1 | 1/2016 | Roberts |
| 2016/0051985 A1 | 2/2016 | Knight et al. |
| 2016/0168579 A1 | 6/2016 | Hutchison et al. |
| 2016/0258939 A1 | 9/2016 | Morin et al. |
| 2016/0304948 A1 | 10/2016 | Lee et al. |
| 2016/0371434 A1 | 12/2016 | Strauss et al. |
| 2017/0017436 A1 | 1/2017 | Church |
| 2017/0021611 A1 | 1/2017 | Jung et al. |
| 2017/0081716 A1 | 3/2017 | Peck |
| 2017/0093851 A1 | 3/2017 | Allen |
| 2017/0136452 A1 | 5/2017 | Niles et al. |
| 2017/0140095 A1 | 5/2017 | Kim |
| 2017/0218228 A1 | 8/2017 | Jose et al. |
| 2017/0363953 A1 | 12/2017 | Steinhart et al. |
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0137418 A1* | 5/2018 | Roquet .................. C12N 9/22 |
| 2018/0173710 A1 | 6/2018 | Maftuleac et al. |
| 2018/0173738 A1 | 6/2018 | Lopez-Ortiz et al. |
| 2018/0253563 A1 | 9/2018 | Peck et al. |
| 2019/0020651 A1 | 1/2019 | Soon-Shiong et al. |
| 2019/0136307 A1 | 5/2019 | Predki et al. |
| 2019/0142882 A1 | 5/2019 | Shepherd et al. |
| 2019/0271032 A1 | 9/2019 | Owen |
| 2019/0351673 A1 | 11/2019 | Roquet et al. |
| 2019/0355442 A1 | 11/2019 | Merriman |
| 2021/0010065 A1 | 1/2021 | Salk et al. |

FOREIGN PATENT DOCUMENTS

| | | |
|---|---|---|
| EP | 2856375 B1 | 7/2018 |
| EP | 3346404 | 7/2018 |
| JP | 2009244996 | 10/2009 |
| WO | WO-03025123 A2 | 3/2003 |
| WO | WO-2004009844 A1 | 1/2004 |
| WO | WO-2012058638 A1 | 5/2012 |
| WO | WO-2014014991 A2 | 1/2014 |
| WO | WO-2015144858 A1 | 10/2015 |
| WO | WO-2016015701 A1 | 2/2016 |
| WO | WO-2016059610 A1 | 4/2016 |
| WO | WO-2016081834 A2 | 5/2016 |
| WO | WO-2016164779 A1 | 10/2016 |
| WO | WO-2016182814 A2 | 11/2016 |
| WO | WO-2017151195 A1 | 9/2017 |
| WO | WO-2017189914 A1 | 11/2017 |
| WO | WO-2017190297 A1 | 11/2017 |
| WO | WO-2017192633 A1 | 11/2017 |
| WO | WO-2018017131 A1 | 1/2018 |
| WO | WO-2018049272 A1 | 3/2018 |
| WO | WO-2018094108 A1 | 5/2018 |
| WO | WO-2018132457 A1 | 7/2018 |
| WO | WO-2018148260 A1 | 8/2018 |
| WO | WO-2018148458 A1 | 8/2018 |
| WO | WO-2018213856 A2 | 11/2018 |
| WO | WO-2019081145 A1 | 5/2019 |
| WO | WO-2019178551 A1 | 9/2019 |
| WO | WO-2020028912 A1 | 6/2020 |

OTHER PUBLICATIONS

Clarke, et al., "Continuous base identification for single-molecule nanopore DNA sequencing", Nature Nanotechnology, vol. 4, pp. 265-270, (2009).

De Silva, et al., "New Trends of Digital Data Storage in DNA", BioMed Research International, vol. 2016, Article ID 8072463, 14 pages (Sep. 5, 2016) pp. 14.

Deorowicz et al., "Data compression for sequencing data," Algorithms for Molecular Biology, vol. 8(25): 1-13 (2013).

Engler et al., "A One Pot, One Step, Precision Cloning Method with High Throughput Capability," PLoS ONE, vol. 3(11): E3647 (2008) printed as pp. 1-7.

Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073, Springer Science+Business Media, New York: 141-156 (2013).

Extended European Search Report for EP Application No. 17872172.6 dated Oct. 27, 2020.

(56) References Cited

OTHER PUBLICATIONS

Fogg et al., "New Applications for Phage Integrases," Journal of Molecular Biology, vol. 426(15): 2703-2716 (2014).
Goldman et al., "Towards practical, high-capacity, low-maintenance information storage in synthesized DNA," Nature, vol. 494: 77-80 (2013).
Kivioja et al., "Counting absolute numbers of molecules using unique molecular identifiers," Nature Methods, vol. 9(1): 72-74 (2011), including pp. 1-2 of Online Methods, and pp. 1-14 of Supplementary Information.
Lee, et al, "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348987.full.pdf [retrieved on Nov. 20, 2019] abstract, pp. 31 pages (2018).
Leier et al., "Cryptography with DNA binary strands," Biosystems, vol. 57: 13-22 (2000).
Navarro, et al., "Compressed Full-Text Indexes", ACM Computing Surveys, ACM, New York, NY, vol. 39, No. 1, Apr. 12, 2007.
Organick, et al., "Random access in large-scale DNA data storage", Nature Biotechnology, 36(3): 242-248, (2018).
Patrick, et al., DNA Assembly in 3D Printed Fluidics, PLOS One, 10(12): e014636 18 pages (2015).
PCT/US2017/062098 International Search Report and Written Opinion dated Mar. 14, 2018.
PCT/US2017/062106 International Search Report and Written Opinion dated Feb. 22, 2018.
PCT/US2019/022596 International Search Report and Written Opinion dated Jun. 28, 2019.
PCT/US2019/032756 International Search Report and Written Opinion dated Sep. 4, 2019.
PCT/US2019/045160 International Search Report and Written Opinion dated Jan. 30, 2020.
PCT/US2020/032384 International Search Report and Written Opinion dated Jul. 30, 2020.
PCT/US2020/055351 International Search Report and Written Opinion dated Mar. 31, 2021.
Quetier et al., "The CRISPR-Cas9 technology: Closer to the ultimate toolkit for targeted genome editing," Plant Science, vol. 242: 65-76 (2015).
Roquet et al., "Synthetic recombinase-based state machines in living cells," Science, vol. 353(6297): 363, aad8559-1-aad8559-13 (2016).
Sands, B. and Brent, R., "Overview of Post Cohen-Boyer Methods for Single Segment Cloning and for Multisegment DNA Assembly," Current Protocols in Molecular Biology, vol. 113: 3.26.1-3.26-20 (2016).
Sorek et al., "CRISPR-Mediated Adaptive Immune Systems in Bacteria and Archaea," Annual Review of Biochemistry, vol. 82: 237-266 (2013).
Sun et al., "Recent advances in targeted genome engineering in mammalian systems," Biotechnology Journal, vol. 7: 1074-1087 (2012).
Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).
Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.
Yazdi et al., "A Rewritable, Random-Access DNA-Based Storage System," Scientific Reports, vol. 5(14138): 1-10 (2015), including pp. 1-19 of Supplementary Information.
Yazdi et al., "DNA-based storage: Trends and Methods," IEEE Transactions on Molecular, Biological, and Multi-Scale Communications, vol. 1(3): 230-248 (Sep. 1, 2015).
Yazdi, et al., "Portable and Error-Free DNA-Based Data Storage", bioRxiv preprint doi: https://doi.org/10.1101/079442 (2016).
Yim et al., "The essential component in DNA-based information storage system: robust error-tolerating module," Frontiers in Bioengineering and Biotechnology, vol. 2, Article 49: 1-5 (2014).
Zhu et al., "High-throughput DNA sequence data compression," Briefings in Bioinformatics, 16(1): 1-15 (2015).
Craig, et al., "Ordering of Cosmid Clones covering the Herpes Simplex Virus Type 1 (HSV-1) genome: a test case for fingerprinting by hybridisation", Nucleic Acids Research, vol. 18, pp. 2653-2660 (1990).

\* cited by examiner $C_{xy}$ is the yth Component in Layer x. for a Starting Library with M Layers, Each with N Components, the Identifiers Would have the Following Architecture:

where a, b, c Represent Elements in the set {1, 2, ..., N}

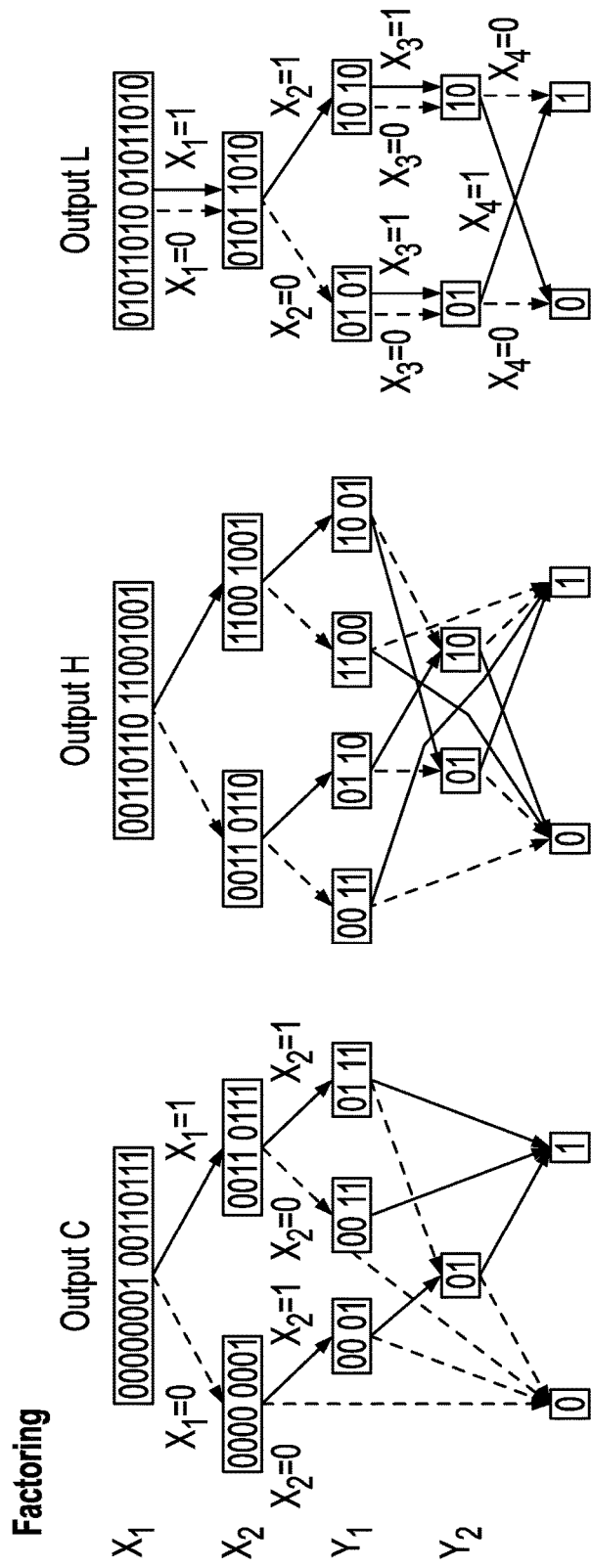

Relabeling

If-Then-Else Gate

Identifier data Map

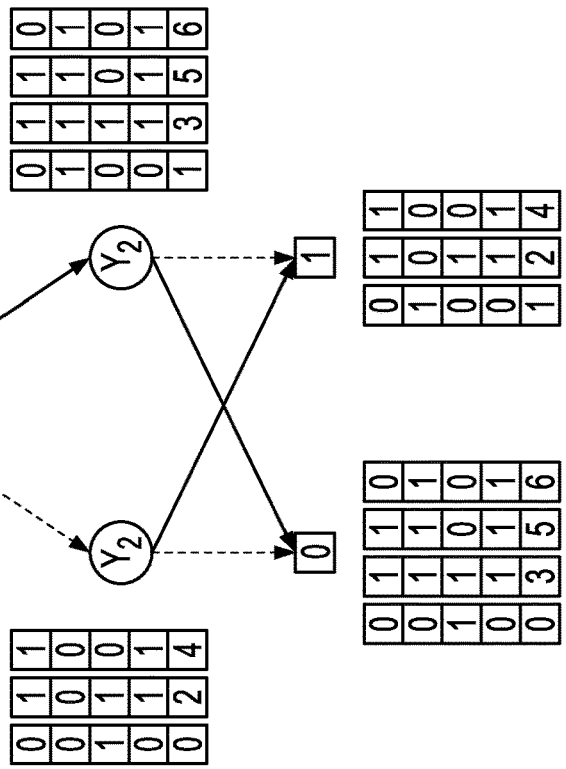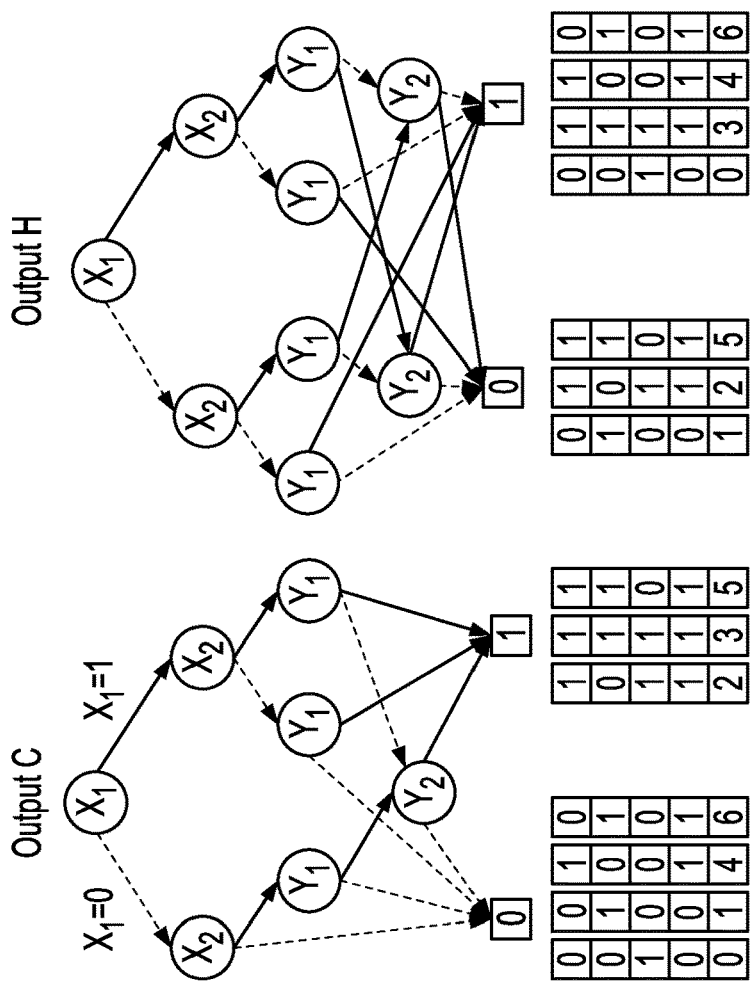

Result Collation

Output C

| Operands $X_1X_2$ | 00 | 01 | 10 | 11 | 10 | 11 | 01 |
|---|---|---|---|---|---|---|---|
| $Y_1Y_2$ | 10 | 00 | 11 | 11 | 01 | 01 | 01 |
| Value | 0 | 1 | 2 | 3 | 4 | 5 | 6 |
| C | 0 | 0 | 1 | 1 | 0 | 1 | 0 |

Output H

| Operands $X_1X_2$ | 00 | 01 | 10 | 11 | 10 | 11 | 01 |
|---|---|---|---|---|---|---|---|
| $Y_1Y_2$ | 10 | 00 | 11 | 11 | 01 | 01 | 01 |
| Value | 0 | 1 | 2 | 3 | 4 | 5 | 6 |
| H | 1 | 0 | 0 | 1 | 1 | 0 | 1 |

Output L

| Operands $X_1X_2$ | 00 | 01 | 10 | 11 | 10 | 11 | 01 |
|---|---|---|---|---|---|---|---|
| $Y_1Y_2$ | 10 | 00 | 11 | 11 | 01 | 01 | 01 |
| Value | 0 | 1 | 2 | 3 | 4 | 5 | 6 |
| L | 0 | 1 | 1 | 0 | 1 | 0 | 0 |

FIG. 14F

Input Samples: s1, s2
Numerical value: 4, 3

| Protocol | Output Sample | Logic |
|---|---|---|
| pcr(s1, s2) | | $2^2 \cdot 4 = 16$ |
| aliquot(s1, 1/2) | | $1/2 \cdot 4 = 2$ |
| mix(s1, s2) | | $4 + 3 = 7$ |
| mix(aliquot(pcr(s1, 1), 3/4), aliquot(pcr(s2,2), (5/6))) | | $3/2 \cdot 4 + 10/3 \cdot 3 = 16$ |

FIG. 15

Protocol: mix(mix(pcr(s1, 2), pcr(s2,1)), s3)

PROGRAMS AND FUNCTIONS IN DNA-BASED DATA STORAGE

REFERENCE TO RELATED APPLICATIONS

This application claims priority to and the benefit of U.S. Provisional Patent Application No. 63/023,071, filed on May 11, 2020, and entitled "BRANCHING PROGRAMS IN DNA-BASED DATA STORAGE"; U.S. Provisional Patent Application No. 63/023,342, filed on May 12, 2020, and entitled "BRANCHING PROGRAMS IN DNA-BASED DATA STORAGE"; U.S. Provisional Patent Application No. 63/066,628, filed on Aug. 17, 2020, and entitled "PROGRAMS AND FUNCTIONS IN DNA-BASED DATA STORAGE"; and U.S. Provisional Patent Application No. 63/165,559, filed on Mar. 24, 2021, and entitled "PROGRAMS AND FUNCTIONS IN DNA-BASED DATA STORAGE". The entire contents of the above-referenced applications are incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

One way to access the digital data stored in nucleic acid molecules, the nucleic acid molecules is to sequence them. As such, nucleic acid digital data storage may be an ideal method for storing data that is not frequently accessed but may have a high volume of information to be stored or archived for long periods of time.

Existing methods of storing data in nucleic acid molecules rely on encoding the digital information (e.g., binary code) into base-by-base nucleic acids sequences, such that the base-to-base relationship in the sequence directly translates into the digital information (e.g., binary code). However, such de novo base-by-base nucleic acid synthesis is error prone and expensive. Moreover, certain functions cannot be performed on data that is stored via these existing methods of nucleic acid digital data storage, when data is encoded at single base resolution, without first translating the entire set of molecules into the digital information. For example, such functions include basic tasks that are commonly performed when the data is stored on a disk, such as logic functions, addition, subtraction, and query search, including whether or not a specific query pattern occurs in a data set, the number of occurrences, and the location of each occurrence.

SUMMARY

The systems, devices, and methods described herein generally relate to methods for encoding data in nucleic acids. Encoding schemes, data structures, access methods, computational programs, and chemical implementations thereof are provided herein. These techniques allow for encoding of and computation on larger datasets than conventional techniques of nucleic acid-based data storage.

In a first aspect, provided herein is a method for storing digital information into nucleic acid molecules. The method comprises partitioning identifiers nucleic acid sequences into blocks, each identifier nucleic acid sequence comprising component nucleic acid sequences, at least a portion of which are configured to bind to one or more probes; allocating a string of symbols to a block of the blocks; mapping the string of symbols to a plurality of identifier nucleic acid sequences within the block; and constructing individual identifier nucleic acid molecules of the plurality of identifier nucleic acid sequences.

In some implementations, said mapping is performed using a codebook that maps words to codewords, wherein said words each comprise one or more symbols of the string, and wherein said codewords each comprise one or more identifier nucleic acid sequences of the identifier nucleic acid sequences to which the string is mapped. There may be a fixed number of codewords per block. A range of identifiers encoding the $g^{th}$ instance of a block can be calculated as the range encoding codeword instances $(g-1)*c+1$ through $g*c$.

In some implementations, a block can be accessed with an access program. A block may be associated with a location, wherein said location comprises information for accessing said block. A block may contain information about the location of another block. A block may represent a node in a graph. Said graph may be a tree. For example, said tree is a suffix tree or B-tree. A block may be an element of an inverted index. Multiple blocks may form a linked list wherein a first block points to a second block to accommodate a large symbol of strings.

In some implementations the identifier nucleic acid sequences of each block exclusively share the same component nucleic acid sequences in a specified set of key layers. Said key layers may encode a data object. Said data object may be a native key. The native key may be configured such that each symbol corresponds to a component nucleic acid sequence of a corresponding key layer. A range query over several keys sharing common symbol values at a specified set of positions may be performed by accessing all identifiers containing their corresponding components. A query for all keys that satisfy a finite automata, or regular expression, may be performed by an access program.

In some implementations, the method further comprises storing a value in the associated block of each key. The value can be retrieved using its corresponding key. The key may be a function of its value. For example, the key is a hash, bloom filter, structural array, classifier, signature, record, or fingerprint derived from its corresponding value. An access program may be designed to access all keys that are similar to, or share symbols values in common with, a query key derived from a reference value.

In some implementations, a count of the number of keys is determined by measuring DNA concentration. DNA concentration may be measured by qPCR assay, plate reader assay, fluorimetry, or spectrophotometry. DNA concentration may be normalized by a standard to determine the number of identifier sequences in a sample. A relative number of keys containing a particular symbol may be determined by performing qPCR with a probe for the corresponding component.

In some implementations, an identifier sequence for a reference key is created. The identifier sequence may be used as a hybridization probe in a hybridization reaction to search for all keys that are similar. The temperature or pH of the hybridization reaction may be used to control the stringency of the similarity search.

In a second aspect, provided herein is a method for operating on digital information stored in nucleic acid molecules. The method comprises (a) obtaining a first pool of identifier nucleic acid molecules, the pool having powder, liquid, or solid form, each identifier nucleic acid molecule in the first pool comprising component nucleic acid molecules, at least a portion of which are configured to bind to one or more probes, wherein the identifier nucleic acid molecules represent input strings of symbols; (b) screening the identifier nucleic acid molecules in the first pool by targeting at least one of the component nucleic acid molecules with a probe, to create an intermediate pool comprising a subset of identifier nucleic acid molecules from said first pool, wherein the intermediate pool represents a result of an if-then-else operation performed on the input strings; and (c) repeating step (b) wherein the intermediate pool replaces the first pool at every subsequent step until a final pool of identifier nucleic acid molecules is created that represents at least a portion of an output string of symbols.

In some implementations, each identifier nucleic acid molecule in the first pool comprises a distinct component nucleic acid sequence from each of M layers, wherein each layer comprises a set of component nucleic acid sequences. Each identifier nucleic acid molecule may represent a data object. A component nucleic acid sequence of the identifier nucleic acid molecule may represent an operand of the data object.

In some implementations, the probe comprises identifier nucleic acid molecules in a pool that include a specific component nucleic acid molecule. In some implementations, the probe is a polymerase chain reaction (PCR) primer, and the if-then-else operation is executed with PCR. In some implementations, the probe is an affinity tagged oligonucleotide, and the if-then-else operation is executed with an affinity pull down assay.

In some implementations, two or more if-then-else operations are performed on one or more pools of identifier nucleic acid molecules in parallel. In some implementations, the method further comprises splitting at least one of the first pool, the intermediate pool, or the final pool into at least two duplicate pools. The method may include replicating the at least one of the first pool, the intermediate pool, or the final pool prior to splitting. For example, replicating is executed with polymerase chain reaction (PCR). The method may include combining at least two intermediate pools of identifier nucleic acid molecules to form a new intermediate pool of identifier nucleic acid molecules or a second pool of identifier nucleic acid molecules.

In some implementations, the repetition of if-then-else operations of (b) in (c) represents execution a graph program, the output of which places an identifier nucleic acid molecule, representing a data object, into the final pool representing the at least a portion of the output string. Said graph program may represent a function on said data object. In some implementations, the at least a portion of the output string is an output of the function on the data object. The final pool to which an identifier nucleic acid molecule is placed into, according to the graph program, may determine the output of the function on the corresponding data object.

In a third aspect, provided herein is a method for storing numerical data in nucleic acids. The method comprises determining an expected copy count of an identifier nucleic acid sequence based on the numerical data and a proportionality constant; and generating a sample containing an actual number of identifier nucleic acid molecules each having the identifier nucleic acid sequence, wherein the actual number approximates the expected copy count.

In some implementations, the numerical data is a number and the expected copy count is proportional to the number. At least a portion of each identifier nucleic acid molecule may be configured to bind to one or more probes. The method may further comprise inputting the sample to an operation to produce an output sample. In some implementations, the operation comprises multiplying the number by a power of 2 by performing a polymerase chain reaction (PCR) with primers that bind to common regions on an edge of the identifier nucleic acid sequence to form the output sample containing a PCR product. For example, the power of 2 corresponds to a number of PCR cycles. In some implementations, the operation comprises multiplying the number by a fraction by performing an aliquot that isolates a fractional volume of the sample to form the output sample. In some implementations, the operation comprises adding the number as a first number to a second number in a second input sample by a mixing operation that combines the sample and the second input sample to form the output sample. The method may further comprise inputting the output sample to a second operation.

In some implementations, the number is a first element of a vector. In some implementations, the method further comprises determining a second expected copy count of the identifier nucleic acid sequence based on a second element of the vector and the proportionality constant; and generating a second sample containing a second actual number of identifier nucleic acid molecules each having the identifier nucleic acid sequence, wherein the second actual number approximates the second expected copy count. The method may further include performing a linear function on the vector by at least one of PCR, aliquoting, and mixing. This may involve converting a binary vector to a unary value in an output sample by performing the linear function. The linear function may be a scoring function. For example, the scoring function computes a higher output value for target vectors than for non-target vectors, such that copy counts for identifier sequences corresponding to target vectors are enriched in the output sample. Identifier sequences corresponding to target vectors may be determined by sequencing the output sample.

In some implementations, a ratio of copy counts between two identifier sequences in the output sample is increased by using a double-stranded DNA selection operation to form a new output sample where identifier sequences corresponding to target vectors are even more enriched in the output sample. The operation, or a repeated application thereof, may correspond to an activation function in a neural network or a quadratic function. The output sample may be allowed to reach equilibrium prior to the double stranded DNA selection operation. The method may involve changing the temperature or adding cofactors to the output sample prior to double stranded DNA selection operation. The double stranded DNA selection operation may involve at least one of chromatography, gel electrophoresis, mass spectrometry, flow cytometry, fluorescent-activated sorting, membrane capture, silica column capture, silica bead capture, or affinity capture.

In some implementations, the vector is a compressed representation of a larger data object, the compressed representation being a hash, a bloom filter, a signature, a structural array, or a fingerprint of the larger data object. The larger data object may be retrieved using the corresponding identifier nucleic acid sequence as a key.

In a fourth aspect, provided herein is a method for preparing a plurality of nucleic acid libraries encoding a dataset. The method comprises providing a dataset comprising at least one data object, each data object having an object-rank and comprising at least one byte-value; dividing each data object into a plurality of parts, wherein the plurality of parts is ranked such that each part of a respective data object comprises: (1) a respective byte-value of the at least one byte-value from the corresponding data object of the part, and (2) a part-rank indicating a position of the respective byte-value of the at least one byte-value of the corresponding data object of the part; and mapping the dataset to a plurality of nucleic acid libraries having a solid, liquid, or powder form, wherein each nucleic acid library has a library-rank and comprises a plurality of nucleic acid molecules that encode parts having the same part-rank from different data objects, wherein the same part-rank corresponds to a respective library-rank, and wherein each nucleic acid molecule comprises a key encoding the respective object-rank and an operand encoding the respective byte-value.

In some implementations, each nucleic acid molecule comprises L components, each component selected from C possible components of a distinct layer of L layers, wherein M of the L components encode the key, and wherein N of the L components encode the operand, such that M+N≤L. The byte-value of the part encoded by each nucleic acid molecule may be stored in the operand of the nucleic acid molecule. In some implementations, each part contains no more than K byte-values, wherein each data object comprises at most T byte-values, and wherein each data object is divided into at most P=[T/K] parts. K may be any value less than $L \times [\log_2 C]/8$. In some implementations, the dataset is encoded using W nucleic acid libraries, each library containing nucleic acid molecules each having an identifier-rank of 1, ..., R, wherein the dataset comprises D data objects, wherein R≥D. The $j^{th}$ part of the P parts of the $r^{th}$ data object of the D data objects is encoded in the operand of a nucleic acid molecule of rank in interval [$C^N r$, $C^N(r+1)-1$] in the $j^{th}$ library.

In a fifth aspect, provided herein is a method of retrieving a subset of a data object of a dataset encoded in a plurality of nucleic acid libraries according to the method of the fourth aspect. The method comprises providing a target nucleic acid library and a query nucleic acid library, each library comprising nucleic acid molecules each comprising a key and an operand; extracting keys from nucleic acid molecules in the query nucleic acid library; matching nucleic acid molecules in the target nucleic acid library having keys that match the keys extracted from the query nucleic acid library; and selecting and outputting the matched nucleic acid molecules.

In some implementations, extracting comprises converting each nucleic acid molecule in the query nucleic acid library to a single-stranded nucleic acid molecule, and wherein matching comprising hybridizing nucleic acid molecules in the target nucleic acid library to complementary single-stranded keys. Selecting may involve applying an enzyme that selectively degrades single-stranded nucleic acids. For example, the enzyme is P1.

In some implementations, extracting comprises digesting each nucleic acid molecule in the query nucleic acid library using a sequence-specific enzyme that recognizes a specific sequence found in each nucleic acid molecule. Extracting may further comprise size-selecting keys present in double-stranded form.

In some implementations, extracting comprises introducing a nick between the key and the operand of each nucleic acid molecule using a sequence-specific nicking enzyme, incorporating a labeled nucleotide at the nick, and capturing the labeled nucleotides to retain keys in a single-stranded form. The labeled nucleotide may include a biotin label, and wherein capturing comprises affinity capture with streptavidin-coated beads.

In some implementations, extracting comprises selectively amplifying via PCR and purifying the keys from the query nucleic acid library, the keys being flanked by universal sequences that serve as primer binding sites for the PCR.

In some implementations, matching comprises converting the target nucleic acid library and the extracted keys to single-stranded forms and hybridizing single-stranded extracted keys to complementary keys in the target nucleic acid library. Selecting may involve selectively degrading remaining single-stranded molecules. Selecting may alternatively involve gel electrophoresis.

In some implementations, the query nucleic acid library encodes a first set of parts of the dataset and the target nucleic acid library encodes a second set of parts of the data set. In this case, the extracting step acts as a first if-then-else operation on the dataset, and wherein the matching step and selecting and outputting step act as a second if-then-else operation on the dataset.

In some aspects, provided herein is a system configured to perform any of the methods described herein. The system may be a printer-finisher system configured to dispense DNA components at discrete locations (e.g., reaction compartments) on a substrate, dispense reagents provide optimal conditions for the ligation reaction, and pool all of the DNA identifiers that comprise a library. The system may store and manipulate nucleic acid molecules in containers (e.g., via automated liquid handling). The system may dispense probes into compartments or containers to access subsets of nucleic acid molecules. The system may be configured to aliquot and replicate pools of nucleic acid molecules.

In some aspects, provided herein is a composition including nucleic acid molecules representing digital information according to any of the methods described herein. The composition includes identifier nucleic acid molecules comprising component nucleic acid molecules. Identifier nucleic acid molecules may be collected in a pool and mapped to digital information. For example, the presence of an identifier indicates a particular bit or symbol value in a string of symbols, and the absence of an identifier indicates another bit or symbol value in the string of symbols.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 13A-13C show compiling of if-then-else programs using identifiers, according to an illustrative implementation;

FIGS. 14A-14F shows execution of if-then-else programs using identifiers, according to an illustrative implementation;

FIG. 15 shows encoding of numerical values using copies of identifiers and protocols for computation with numerical values encoded with identifiers, according to an illustrative implementation;

DETAILED DESCRIPTION

Figure 1A:
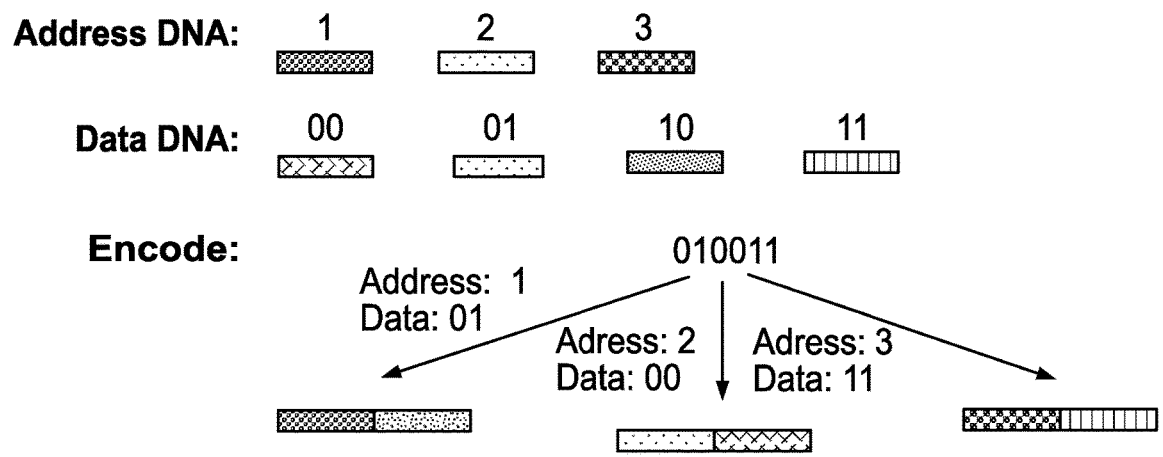
FIGS. 1A and 1B show a schematic of "data at address" encoding, using identifiers (e.g., nucleic acid molecules), according to an illustrative implementation.

To provide an overall understanding of the systems, method, and devices described herein, certain illustrative embodiments will be described. Although the embodiments and features described herein are specifically described for use in connection with particular encoding schemes utilizing nucleic acid molecules, it should be understood that certain methods, techniques, or schemes may be applied to other applications of nucleic acid-based data storage or other chemical-based systems.

Base-by-base synthesis of nucleic acids for encoding digital information can be costly and time consuming, because it generally requires a de novo base-by-base synthesis of distinct nucleic acid sequences (e.g., phosphoramidite synthesis) for every new information storage request. The present disclosure relates to systems and methods that do not rely on base-by-base or de novo synthesis, and instead encode the digital information in a plurality of identifiers, or nucleic acid sequences, that include combinatorial arrangements of components (or component nucleic acid sequences). In this manner, the systems and methods of the present disclosure improve the efficiency and commercial viability of digital information storage.

The present disclosure describes methods that produce a first set of distinct nucleic acid sequences (or components) for the first request of information storage, and can thereafter reuse the same nucleic acid sequences (or components) for subsequent information storage requests. These approaches significantly reduce the cost of DNA-based information storage by reducing the role of de novo synthesis of nucleic acid sequences in the information-to-DNA encoding and writing process.

Moreover, unlike implementations of base-by-base synthesis, such as phosphoramidite chemistry-based or template-free polymerase-based nucleic acid elongation, which use cyclical delivery of each base to each elongating nucleic acid, the systems and methods of the present disclosure relate to information-to-DNA writing using identifier construction from components are highly parallelizable processes that do not necessarily use cyclical nucleic acid elongation. Thus, the present disclosure increases the speed of writing digital information to DNA compared to other methods. Various systems and methods of writing digital information into nucleic acid molecules are described in U.S. Pat. No. 10,650,312 entitled "NUCLEIC ACID-BASED DATA STORAGE", filed Dec. 21, 2017 (describing encoding digital information in DNA); U.S. application Ser. No. 16/461,774 entitled "SYSTEMS FOR NUCLEIC ACID-BASED DATA STORAGE", filed May 16, 2019 and published as U.S. Publication No. 2019/0362814 (describing encoding schemes for DNA-based data storage); U.S. application Ser. No. 17/012,909, entitled "CHEMICAL METHODS FOR NUCLEIC ACID-BASED DATA STORAGE", filed Sep. 4, 2020 and published as U.S. Publication No. 2021/0079382 (describing chemical techniques and instruments for implementing various encoding schemes); U.S. application Ser. No. 16/414,758 entitled "COMPOSITIONS AND METHODS FOR NUCLEIC ACID-BASED DATA STORAGE", filed May 16, 2019 and published as U.S. Publication No. 2020/0193301 (describing encoding schemes, partitioning, and logic gates); U.S. application Ser. No. 16/414,752 entitled "PRINTER-FINISHER SYSTEM FOR DATA STORAGE IN DNA", filed May 16, 2019 and published as U.S. Publication No. 2019/0351673 (describing an assembly for producing encoded nucleic acid libraries); U.S. Application No. U.S. application Ser. No. 16/532,077 entitled "SYSTEMS AND METHODS FOR STORING AND READING NUCLEIC ACID-BASED DATA WITH ERROR PROTECTION", filed Aug. 5, 2019 and published as U.S. Publication No. 2020/0185057 (describing data structures and error protection and correction); and U.S. application Ser. No. 16/872,129 entitled "DATA STRUCTURES AND OPERATIONS FOR SEARCHING, COMPUTING, AND INDEXING IN DNA-BASED DATA STORAGE", filed May 11, 2020 and published as U.S. Publication No. 2020/0357483 (describing advanced data structures and protocols for access, rank, count, search, and extract operations), each of which is hereby incorporated by reference in its entirety.

The following description begins with an overview of various systems and methods for encoding data in nucleic acid molecules, and describes various writing and archival systems configured to print and store nucleic acid molecules that encode digital data, as described in relation to FIGS. 1-8. Translation of bits to ordered nucleic acid molecules is described in relation to FIGS. 9 and 10. Encoded information can be allocated in a data structure to allow for easier access and reading of the information, as described in relation to FIGS. 11 and 21. The ordered nucleic acid molecules may be structured with native key-value pairs to encode metadata of the data structure or encoded dataset, as described in relation to FIGS. 12 and 21. Nucleic acids encoded in this manner are particularly useful for large-scale computation using graph programs, or if-then-else operations, as described in relation to FIGS. 13A-14 and 22.

Nucleic acids are also advantageous for physical storage of numerical values by approximation with copy counts of nucleic acid sequences, as described in relation to FIGS. 15-17B and 23. Another encoding scheme involves dividing data objects into parts, with byte-values of said parts encoded by distinct "stripe libraries", as described in relation to FIGS. 18 and 24. Stripe libraries can be "filtered" to obtain target sequences, as described in relation to FIGS. 19A-19B and 24. Stripe libraries can also be used for computation with if-then-else operations, as described in relation to FIGS. 20 and 24.

Generally, the present disclosure encodes data (which is represented by a string of one- or zero-bits, or by a string of symbols, where each symbol is selected from a set of more than two symbol values) into a set of identifier nucleic acid sequences (or identifier sequence), where each unique identifier sequence has a corresponding bit or symbol in the string. The identifier sequence encodes the bit or symbol's position in the string, its value, or both the position and value. One way to implement the systems and methods of the present disclosure is to create each identifier nucleic acid molecule (or identifier molecule), which is represented by an identifier sequence, by ligating premade DNA component molecules (represented by component sequences) in an ordered manner that is based on defined layers, as is discussed in relation to FIGS. 1-8. Specifically, the component sequences in the different layers are combinatorially combined across the layers (one component sequence is selected per layer, for example) and concatenated (e.g., ligated) to form identifier sequences that are mapped one-to-one to each symbol or bit in the string.

Generally, a component nucleic acid sequence is configured to bind one or more probes that can be used to select for all identifiers comprising said sequence. For example, a component may comprise a target sequence of 20 bases and a probe may comprise a complementary 20 base oligonucleotide for binding the target sequence. As described in the present disclosure, the composition of identifier nucleic acid sequences from components, each of which are capable of binding a unique probe, offers beneficial features when it comes to accessing and operating on the stored data. Though the methods of generating identifiers presented herein are especially configured to generate identifiers comprising components, it should be understood that such identifier nucleic acid molecules may be formed through a number of alternative methods. For example, de novo synthesis that generates nucleic acid sequences of length 100 bases can be used to create identifier nucleic acid sequences wherein each identifier comprises five components of 20 bases each. If all combinations of bases are available for synthesis, there may be up to $4^{20}$ possible sequences for each component.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence or nucleic acid molecule. A component may comprise a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some implementations, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some implementations, the absence of a given identifier in the identifier library may indicate a symbol value at a particular position. One or more identifier libraries may be combined in a pool, group, or set of identifiers, for example, having solid, liquid, or powder form. Each identifier library may include a unique barcode that identifies the identifier library.

The term "probe," as used herein generally refers to an agent that binds a target sequence on an identifier nucleic acid molecule. The target sequence can be a portion of a component. The probe may comprise a sequence that matches or is the complement of its target sequence. The probe may be further used to isolate all identifier nucleic acid molecules comprising said target sequence. For example, the probe may be a primer in a PCR reaction that enriches all identifier nucleic acid molecules comprising a target sequence. Alternatively, the probe may contain be an affinity tagged oligonucleotide molecule that can be used to select all identifier nucleic acid molecules with a sequence that corresponds to said oligonucleotide. Probes may also be used for negative selection. For example, an affinity tagged probe can be used to remove all identifiers containing a particular target sequence. Alternatively, a probe may comprise an active nuclease, such as Cas9, that cleaves or digests all identifiers containing a particular target sequence.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" refers to the alphabetical representation of a polynucleotide that defines the order of nucleotides; the term "nucleic acid molecule" refers to physical instance of the polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

It is to be understood that the terms "index" and "position" are used interchangeably in the present disclosure, and it is to be understood that both terms are used to refer to a specific element or entity of an ordered collection, such as a list or a string. For example, an index or position may be used to specify an element in an array, vector, string, or data structure. Index/position notation uses a numbering scheme to assign nominal numbers to each entry/entity. The examples in the present disclosure often use a first index/position of 0, known in the art as zero-based numbering. The first position (also referred to as the zero-th position) of an array/string is denoted by 0 for purposes of computation involving the specific position). A set of length n would have a numbering scheme of 0, 1, . . . , n−1. It is to be understood that other numbering schemes may be used in the systems and methods described herein. For example, a numbering scheme may start at 1 and continue to n for a set of length n.

The present disclosure describes methods in relation to the figures of the application. It is to be understood that these methods, including computational steps, are configured to be performed in DNA. Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Writing Digital Data Into Nucleic Acids

Identifiers (nucleic acid molecules) have nucleic acid sequences that can be used to encode digital information, such as a string of symbols. Identifiers are formed by assembling components (nucleic acid molecules). Components may be configured to bind a probe (as described in the foregoing), and these components configured as such are "addressable components." All components described herein may be addressable components.

In some embodiments, the identifiers may be comprised entirely of addressable components. The addressable components may be assembled to form an identifier or they may be introduced into an identifier sequence through subtractive or substitution approaches. Alternatively, they may be incorporated into a nucleic acid identifier by de novo synthesis. Different writing methods vary in speed and cost. They can also vary in the number of possible components that can be incorporated into an identifier.

FIGS. 1A/1B and 2A/2B illustrate examples of how identifiers comprising components can encode digital information using a "data at address" encoding scheme (also referred to as "longitudinal encoding" herein) whereby a data object, such as a "byte-value" is encoded along an identifier.

Figure 1B:
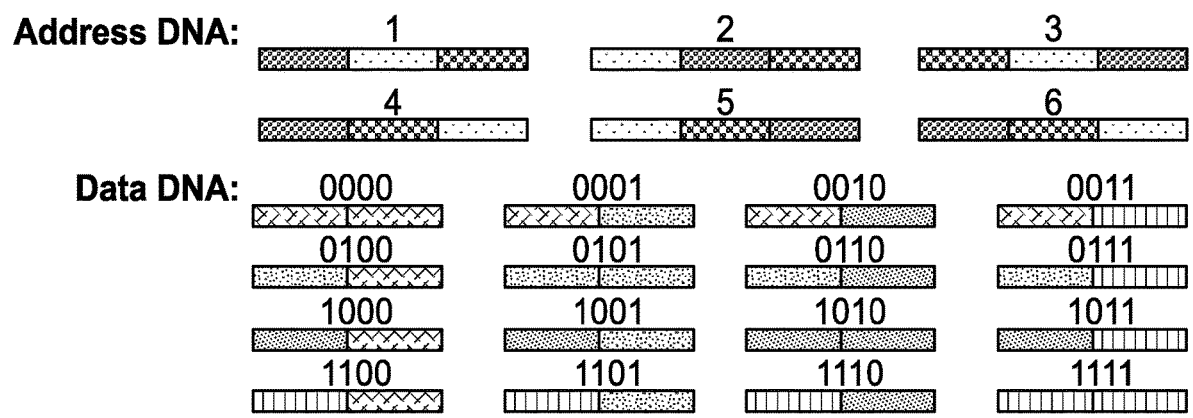

FIGS. 1A and 1B schematically illustrate an example method, referred to as "data at address", of encoding digital data in objects or identifiers (e.g., nucleic acid molecules), according to an illustrative implementation. FIG. 1A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 1B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 1A).

Figure 2A:
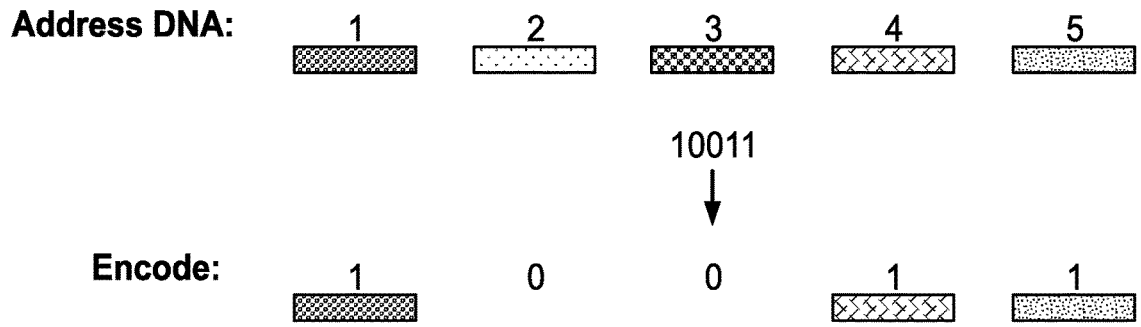
FIGS. 2A and 2B show a schematic of encoding digital information using identifiers, according to an illustrative implementation.
Figure 2B:
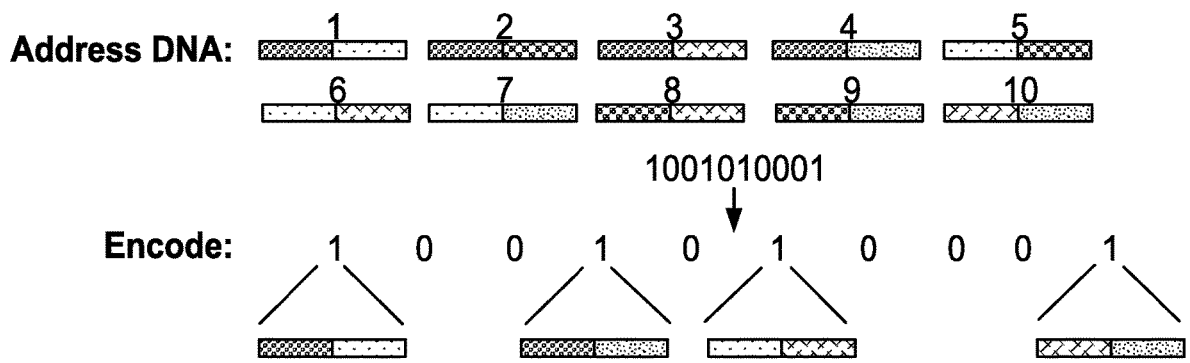

FIGS. 2A and 2B schematically illustrate another example method of encoding digital information in objects or identifiers (e.g., nucleic acid sequences), according to an illustrative implementation. FIG. 2A illustrates encoding a bit stream into an identifier library wherein identifiers are constructed from single components that specify identifier rank, corresponding to a position in the bit stream. The presence of an identifier at a particular rank (or address) specifies a bit-value of 1 and the absence of an identifier at a particular rank (or address) specifies a bit-value of 0. This type of encoding may use identifiers that solely encode rank (the relative position of a bit in the original bit stream) and use the presence or absence of those identifiers in an identifier library to encode a bit-value of 1 or 0, respectively. Reading and decoding the information may include identifying the identifiers present in the identifier library, assigning bit-values of 1 to their corresponding ranks and assigning bit-values of 0 elsewhere. While the presence of an identifier encodes a one-bit and an absense of an identifier encodes a zero-bit in the example, it will be understood that the presence of an identifier could encode a zero-bit while an absence of an identifier encodes a one-bit, without departing from the scope of the present disclosure.

FIG. 2B is similar to FIG. 2A, but in the example encoding method of FIG. 2B, each identifier is combinatorially constructed from a set of components such that each possible combinatorial construction specifies a rank. Such combinatorial construction enables more information to be written into identifiers than if the identifiers where made from the single components alone (e.g., FIG. 2A). For example, as depicted in FIG. 2B, the ten addresses, corresponding to a bit string of length N=10, are represented using a component set of five distinct components. The five distinct components are assembled in a combinatorial manner to generate ten distinct identifiers, each comprising two of the five components. The ten distinct identifiers each have a rank (or address) that corresponds to the position of a bit in a bit stream. An identifier library may include the subset of those ten possible identifiers that corresponds to the positions of bit-value 1, and exclude the subset of those ten possible identifiers that corresponds to the positions of the bit-value 0 within a bit stream of length ten.

Figure 3:
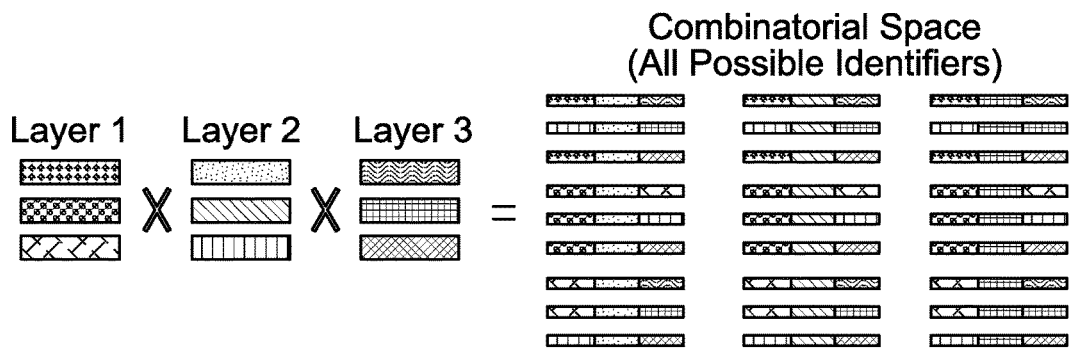
FIG. 3 shows a "product scheme" method for constructing identifiers by combinatorially assembling distinct components, according to an illustrative implementation.

FIG. 3 illustrates an example method, referred to as the "product scheme", for constructing identifiers (e.g., nucleic acid molecules) by combinatorially assembling a distinct component (e.g., nucleic acid sequence) from each layer in a fixed order, according to an illustrative implementation. The top portion of FIG. 3 depicts the architecture of identifiers constructed using the product scheme. An identifier may be constructed by combining a single component from each layer in a fixed order. For M layers, each with N components, there are $N^M$ possible identifiers. The bottom portion of FIG. 3 illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

FIGS. 4-7 illustrate chemical methods for implementing the product scheme (see FIG. 3). Methods depicted in FIGS. 4-7, along with any other methods for assembling two or more distinct components in a fixed order may be used, for example, to produce any one or more identifiers in an identifier library. These methods are described in U.S. Pat. No. 10,650,312 entitled "NUCLEIC ACID-BASED DATA STORAGE", filed Dec. 21, 2017, which is incorporated by reference in its entirety. Identifiers may be constructed using any of the implementation methods described in FIGS. 4-7, at any time during the methods or systems disclosed herein.

In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Enzymatic reactions may be used to assemble components from the different layers or sets. Assembly can occur in a one pot reaction because components (e.g., nucleic acid sequences) of each layer have specific hybridization or attachment regions for components of adjacent layers. For example, a nucleic acid sequence (e.g., component) X1 from layer X, a nucleic acid sequence Y1 from layer Y, and a nucleic acid sequence Z1 from layer Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. The one reaction may involve self-assembly of components into identifiers.

Figure 4:
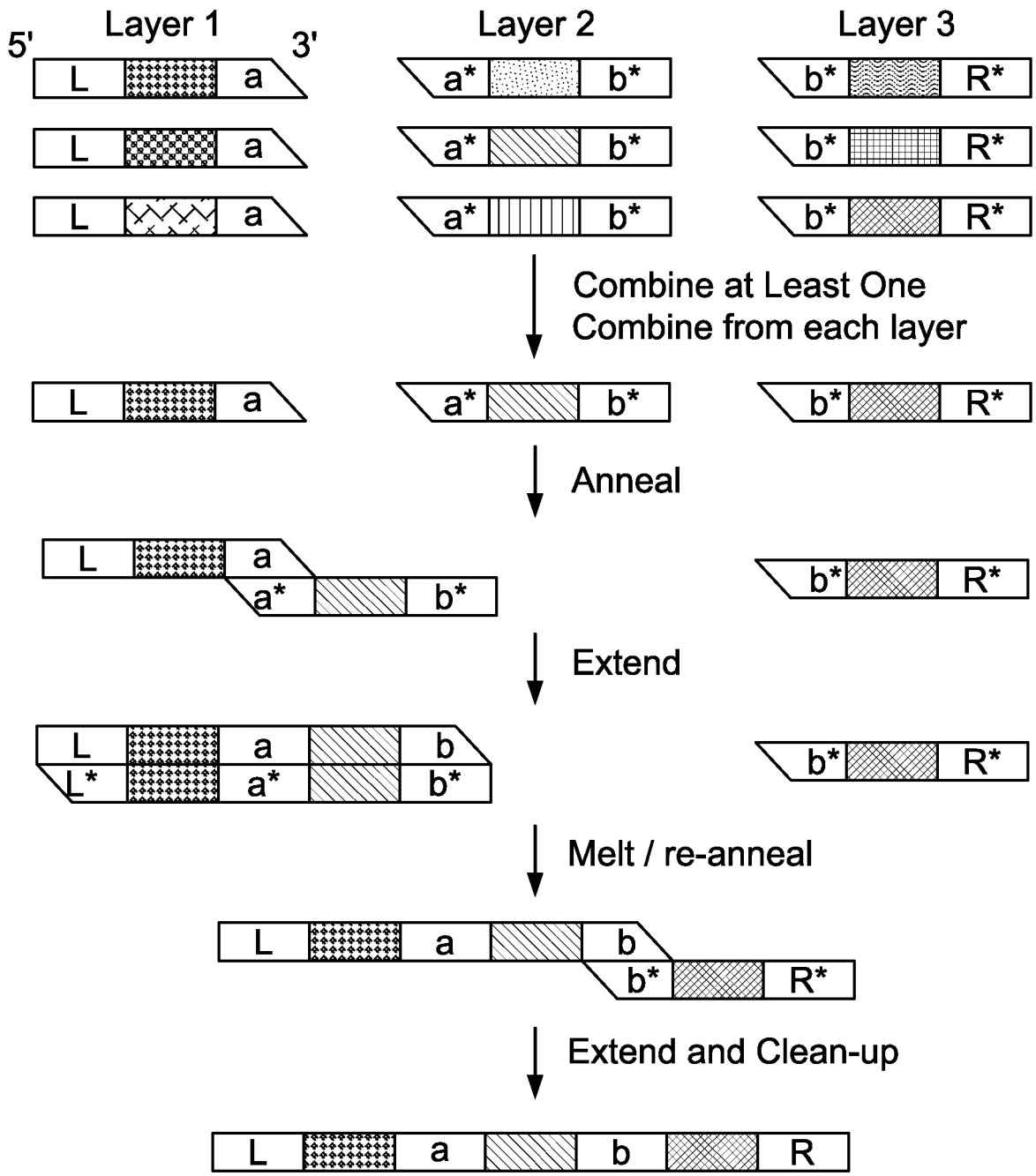
FIG. 4 shows a schematic of using overlap extension polymerase chain reaction to construct identifiers from components, according to an illustrative implementation.

Identifiers may be constructed in accordance with the product scheme using overlap extension polymerase chain reaction (OEPCR), as illustrated in FIG. 4, according to an illustrative implementation. Each component in each layer may comprise a double-stranded or single stranded (as depicted in FIG. 4) nucleic acid sequence with a common hybridization region on the sequence end that may be homologous and/or complementary to the common hybridization region on the sequence end of components from an adjacent layer. Accordingly, all the components and necessary reagents to form a plurality of identifiers may be deposited simultaneously in a reaction compartment, and the hybridization regions on each component allow them to self-assemble into the desired unique identifier molecules, because the order of assembled components is controlled by design of the hybridization regions.

Figure 5:
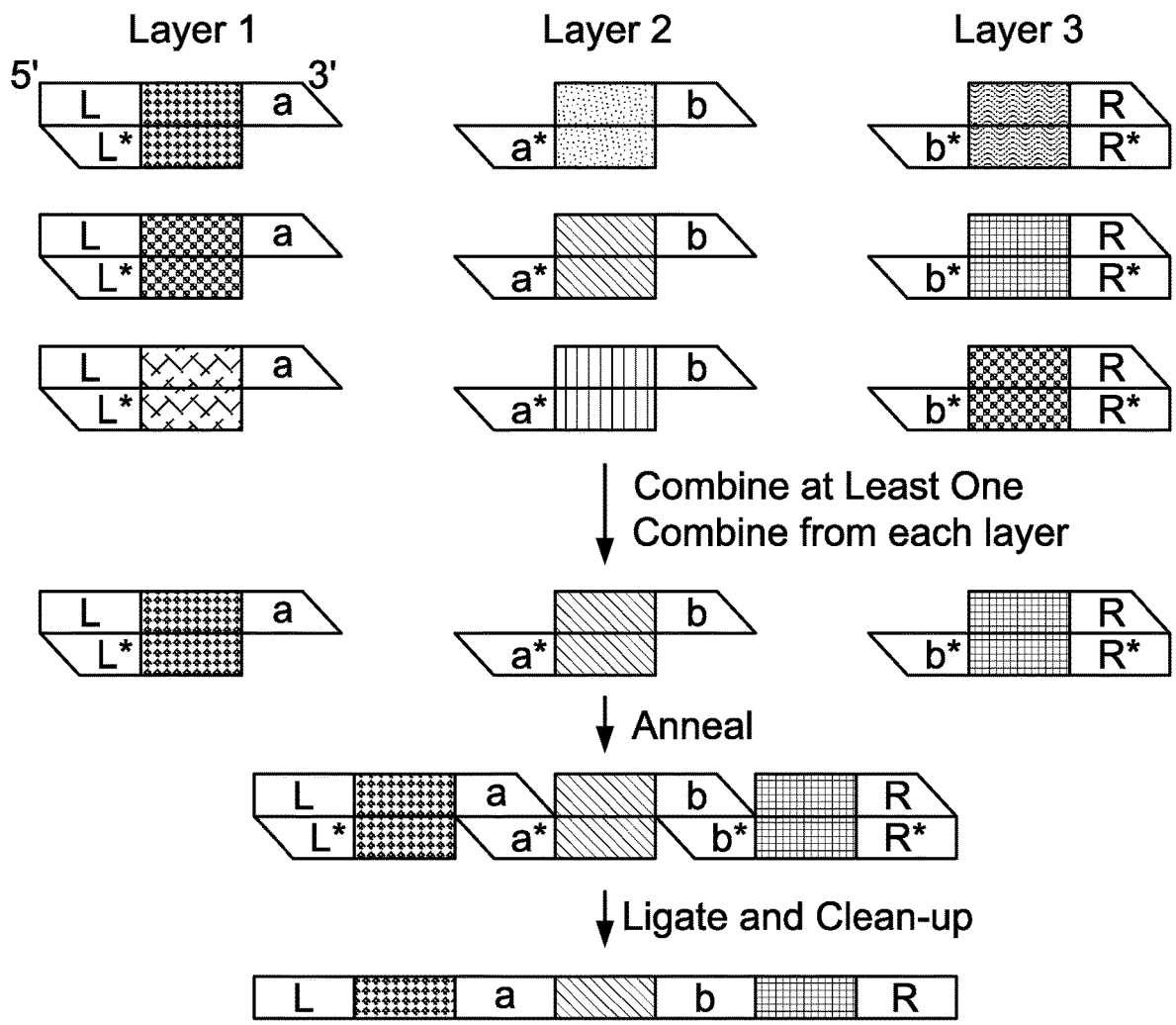
FIG. 5 shows a schematic of using sticky end ligation to construct identifiers from components, according to an illustrative implementation.

Identifiers may be assembled in accordance with the product scheme using sticky end ligation, as illustrated in FIG. 5, according to an illustrative implementation. Three layers, each comprising double stranded components (e.g., double stranded DNA (dsDNA)) with single-stranded 3' overhangs, can be used to assemble distinct identifiers. The sticky ends for sticky end ligation may be generated by treating the components of each layer with restriction endonucleases. In some implementations, the components of multiple layers may be generated from one "parent" set of components.

Figure 6A:
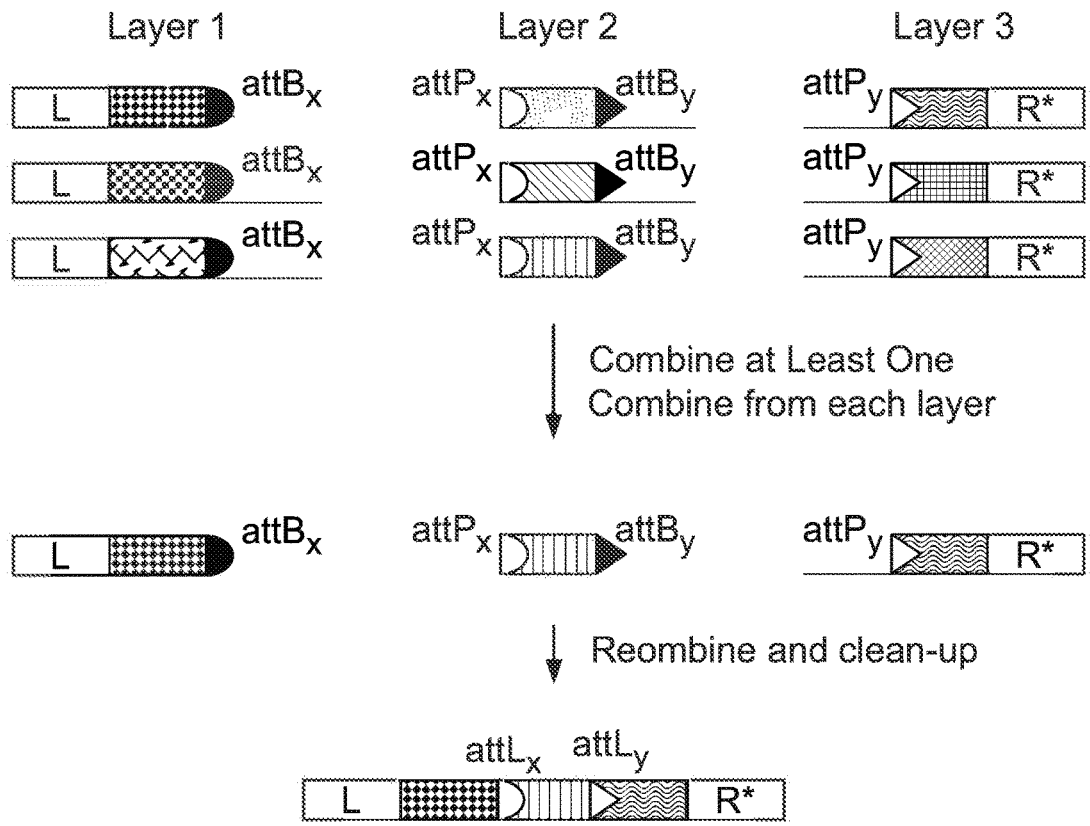
FIGS. 6A and 6B show a schematic of using recombinase assembly to construct identifiers from components, according to an illustrative implementation.
Figure 6B:

Identifiers may be assembled in accordance with the product scheme using site specific recombination, as illustrated in FIGS. 6A and 6B, according to an illustrative implementation. Identifiers may be constructed by assembling components from three different layers. The components in layer X (or layer 1) may comprise double-stranded molecules with an attBx recombinase site on one side of the molecule, components from layer Y (or layer 2) may comprise double-stranded molecules with an attP recombinase site on one side and an $attB_y$ recombinase site on the other side, and components in layer Z (or layer 3) may comprise an $attP_y$ recombinase site on one side of the molecule. attB and attP sites within a pair, as indicate by their subscripts, are capable of recombining in the presence of their corresponding recombinase enzyme. One component from each layer may be combined such that one component from layer X associates with one component from layer Y, and one component from layer Y associates with one component from layer Z. Accordingly, all the components and necessary reagents to form a plurality of identifiers may be deposited simultaneously in a reaction compartment, and the recombinase sites on each component allow them to self-assemble into the desired unique identifier molecules, because the order of assembled components is controlled by design of the recombinase sites.

Figure 7:
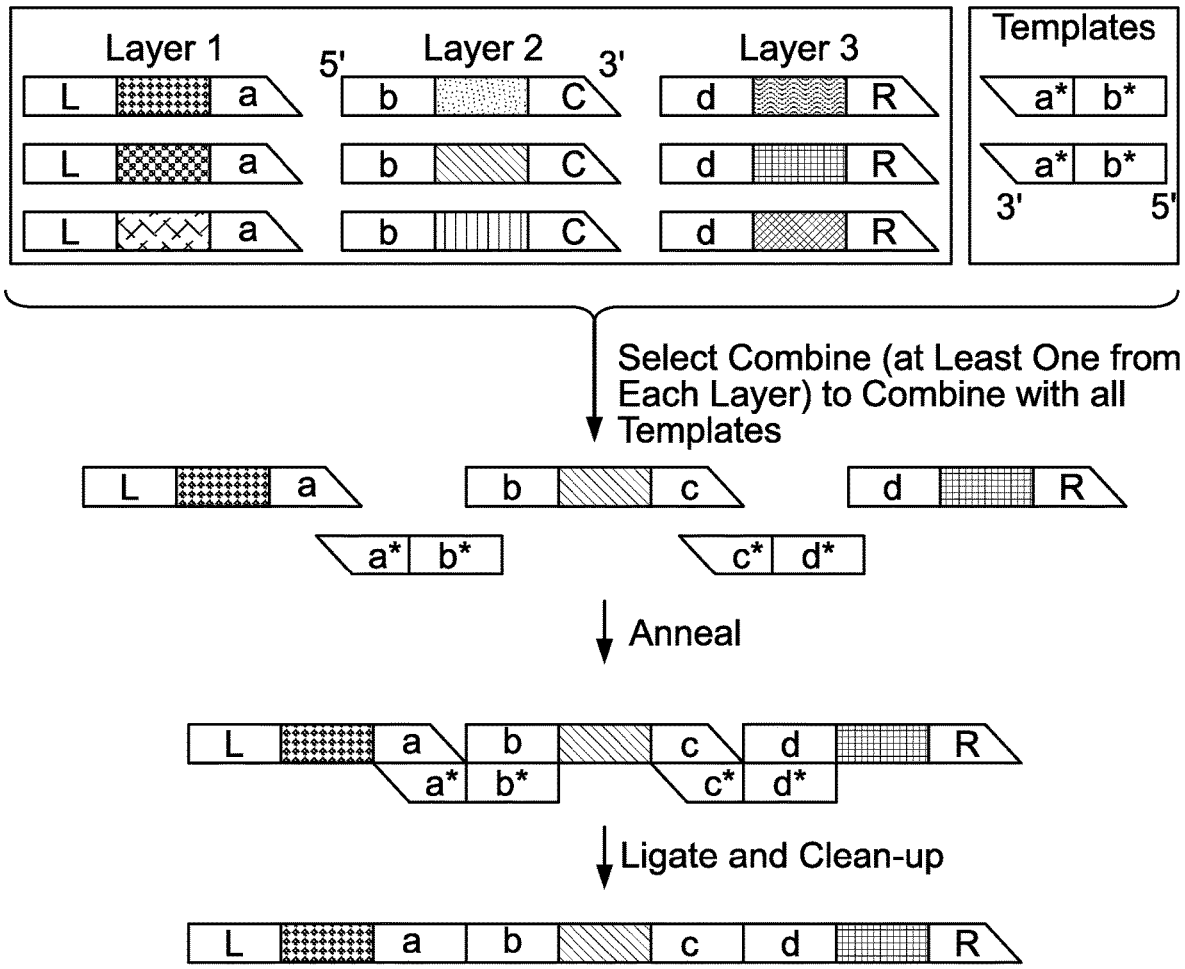
FIG. 7 shows a schematic of using template directed ligation to construct identifiers from components, according to an illustrative implementation.

Identifiers may be constructed in accordance with the product scheme using template directed ligation (TDL), as shown in FIG. 7, according to an illustrative implementation. Template directed ligation utilizes single stranded nucleic acid sequences, referred to as "templates" or "staples", to facilitate the ordered ligation of components to form identifiers. The templates simultaneously hybridize to components from adjacent layers and hold them adjacent to each other (3' end against 5' end) while a ligase ligates them. Accordingly, all the components and necessary reagents to form a plurality of identifiers may be deposited simultaneously in a reaction compartment, and the hybridization regions on each component allow them to self-assemble into the desired unique identifier molecules, because the order of assembled components is controlled by design of the templates.

Figure 8A:
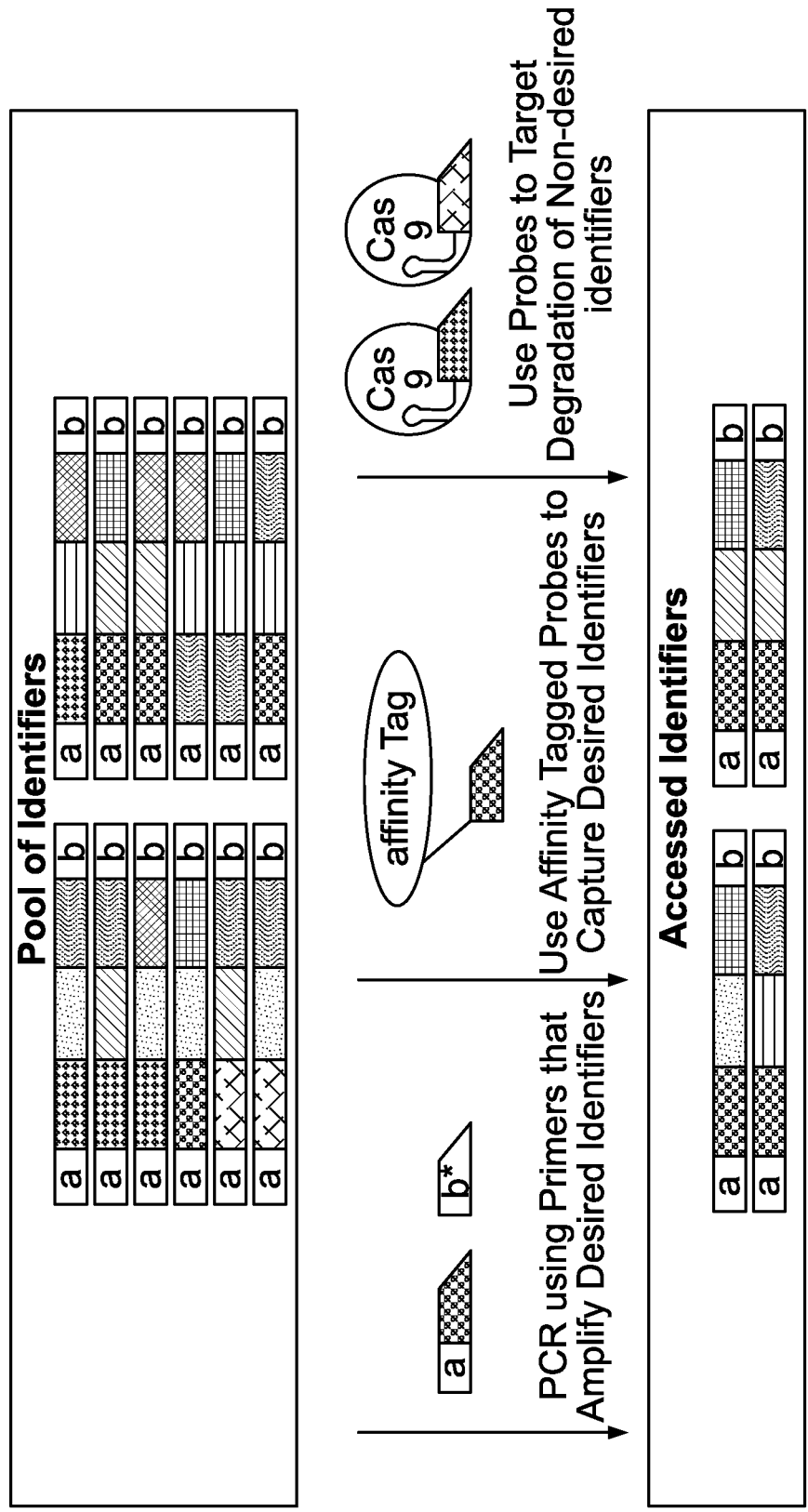
FIGS. 8A-8C show a schematic for accessing portions of information stored in nucleic acid sequences by accessing particular identifiers using probes, according to an illustrative implementation.
Figure 8B:
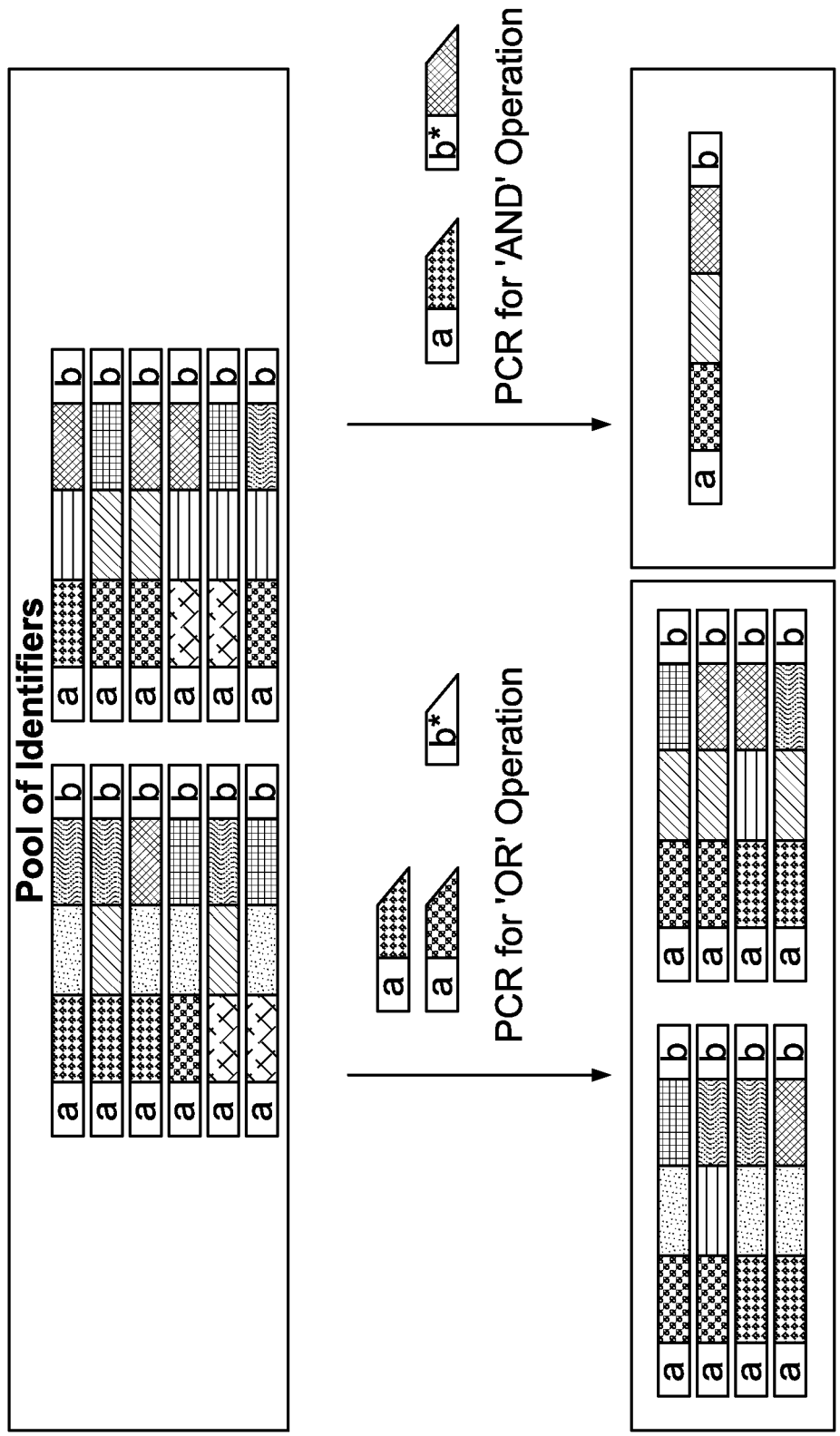
Figure 8C:
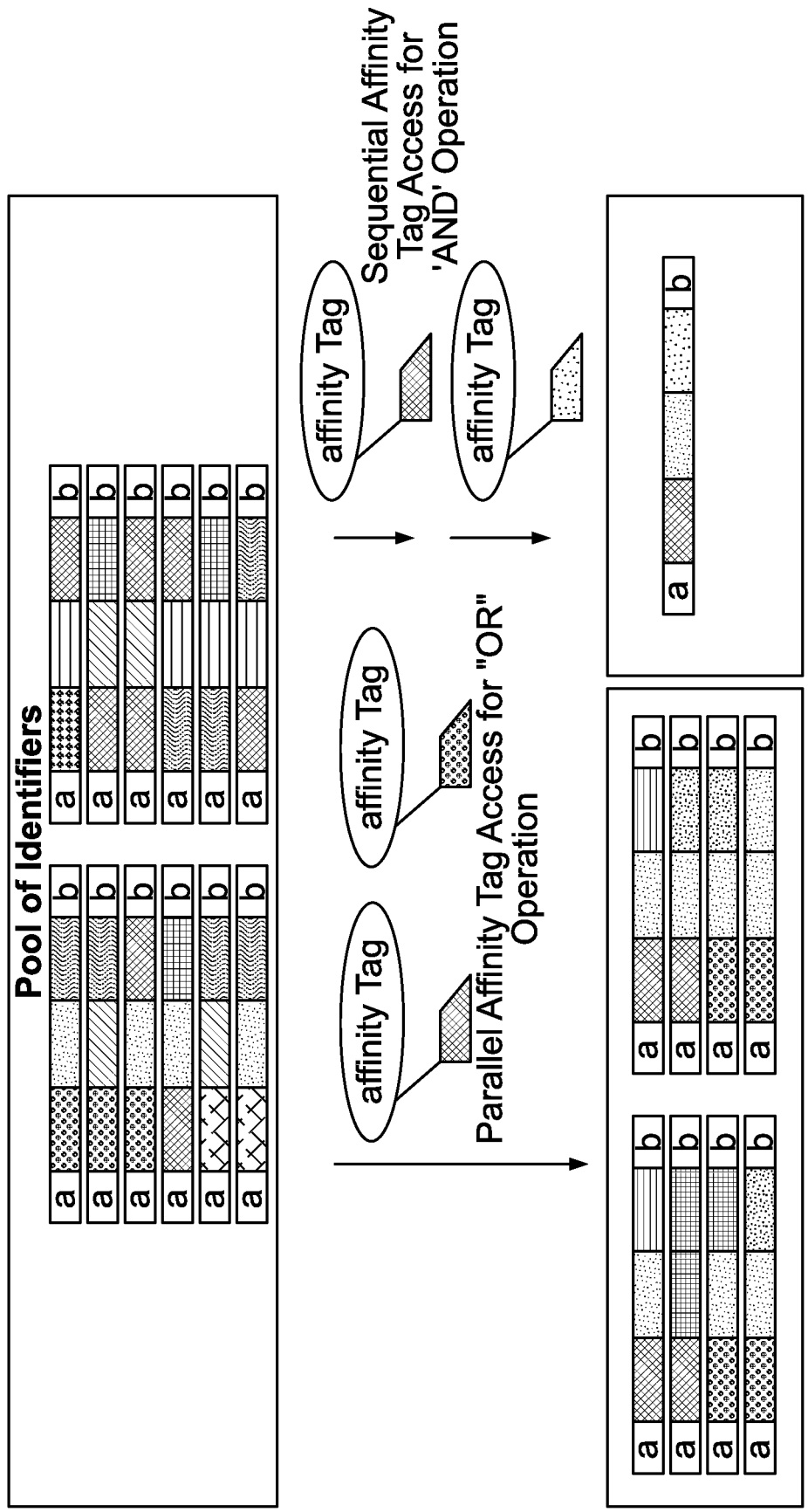

FIGS. 8A-8C illustrate examples of using probes to access specified subsets of identifiers from an identifier library. FIG. 8A shows example methods for using polymerase chain reaction, affinity tagged probes, and degradation targeting probes to access identifiers containing a specified component. For PCR-based access, a pool of identifiers (e.g., identifier library) may comprise identifiers with a common sequence at each end, a variable sequence at each end, or one of a common sequence or a variable sequence at each end. The common sequences or variable sequences may be primer binding sites. One or more primers may bind to the common or variable regions on the identifier edges. The identifiers with primers bound may be amplified by PCR. The amplified identifiers may significantly outnumber the non-amplified identifiers. During reading, the amplified identifiers may be identified. An identifier from an identifier library may comprise sequences on one or both of its ends that are distinct to that library, thus enabling a single library to be selectively accessed from a pool or group of more than one identifier libraries.

For affinity-tag based access, a process which may be referred to as nucleic acid capture, the components that constitute the identifiers in a pool may share complementarity with one or more probes. The one or more probes may bind or hybridize to the identifiers to be accessed. The probe may comprise an affinity tag. The affinity tags may bind to a bead, generating a complex comprising a bead, at least one probe, and at least one identifier. The beads may be magnetic, and together with a magnet, the beads may collect and isolate the identifiers to be accessed. The identifiers may be removed from the beads under denaturing conditions prior to reading. Alternatively, or in addition to, the beads may collect the non-targeted identifiers and sequester them away from the rest of the pool that can get washed into a separate vessel and read. The affinity tag may bind to a column. The identifiers to be accessed may bind to the column for capture. Column-bound identifiers may subsequently be eluted or denatured from the column prior to reading. Alternatively, the non-targeted identifiers may be selectively targeted to the column while the targeted identifiers may flow through the column. Accessing the targeted identifiers may comprise applying one or more probes to a pool of identifiers simultaneously or applying one or more probes to a pool of identifiers sequentially.

For degradation based access, the components that constitute the identifiers in a pool may share complementarity with one or more degradation-targeting probes. The probes may bind to or hybridize with distinct components on the identifiers. The probe may be a target for a degradation enzyme, such as an endonuclease. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s), such as the S1 nuclease, that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

FIG. 8B shows example methods for using polymerase chain reaction to perform 'OR' or 'AND' operations to access identifiers containing multiple components. In an example, if two forward primers bind distinct sets of identifiers on the left end, then an OR amplification of the union of those sets of identifiers may be accomplished by using the two forward primers together in a multiplex PCR reaction with a reverse primer that binds all of the identifiers on the right end. In another example, if one forward primer binds a set of identifiers on the left end and one reverse primer binds a set of identifiers on the right end, then an AND amplification of the intersection of those two sets of identifiers may be accomplished by using the forward primer and the reverse primer together as a primer pair in a PCR reaction. This process may be repeated in a sequential fashion (e.g., nested PCR) to access identifier sub-pools with any number of components in common.

With each iteration of PCR-based access on an identifier library, the identifiers may become shorter as primers are designed to bind components iteratively further inward from each edge. For example, an identifier library may comprise identifiers of the form A B C D E F G, where A, B, C, D, E, F, and G are layers. Upon amplifying with primers that bind particular components, for example, A1 and G1 in layers A and G respectively, the amplified portion of the identifier library may take on the form A1-B-C-D-E-F-G1. Upon further amplifying with primers that bind particular components, for example, B1 and F1 in layers B and F respectively, the amplified portion of the identifier library may take on the form B1-C-D-E-F1, where it may be assumed that these shorter amplified sequences correspond to full identifiers that further comprise component A1 in the position of layer A and G1 in the position of layer G.

FIG. 8C shows example methods for using affinity tags to perform 'OR' or 'AND' operations to access identifiers containing multiple components. In an example, if affinity probe 'P1' captures all identifiers with component 'C1' and another affinity probe 'P2' captures all identifiers with component 'C2', then the set of all identifiers with C1 or C2 can be captured by using P1 and P2 simultaneously (corresponding to an OR operation). In another example with the same components and probes, the set of all identifiers with C1 and C2 can be captures by using P1 and P2 sequentially (corresponding to an AND operation).

Encoding Data Structures in Nucleic Acids
Translating Bits to Identifiers

Each identifier in a combinatorial space can comprise a fixed number of N components where each component comes from a distinct layer in a set of N layers, and is one of a number of a set of possible components in said layer. Each component can be specified by a coordinate $(j, X_j)$ where j is the label of the layer and $X_j$ is the label of the component within the layer. For said scheme with N layers, j is an element of the set $\{1, 2, \ldots, N\}$ and $X_j$ is an element of the set $\{1, 2, \ldots, M_j\}$ where $M_j$ is the number of components in layer j. A logical order to the layers can be defined. A logical order to each component within each layer can also be defined. This labeling can be used to define a logical ordering to all possible identifiers in the combinatorial space. For example, first the identifiers can be sorted according to the order of the components in layer 1, and then subsequently according to the order of the components in layer 2, and so on, as shown by example in FIG. 9.

Figure 9:
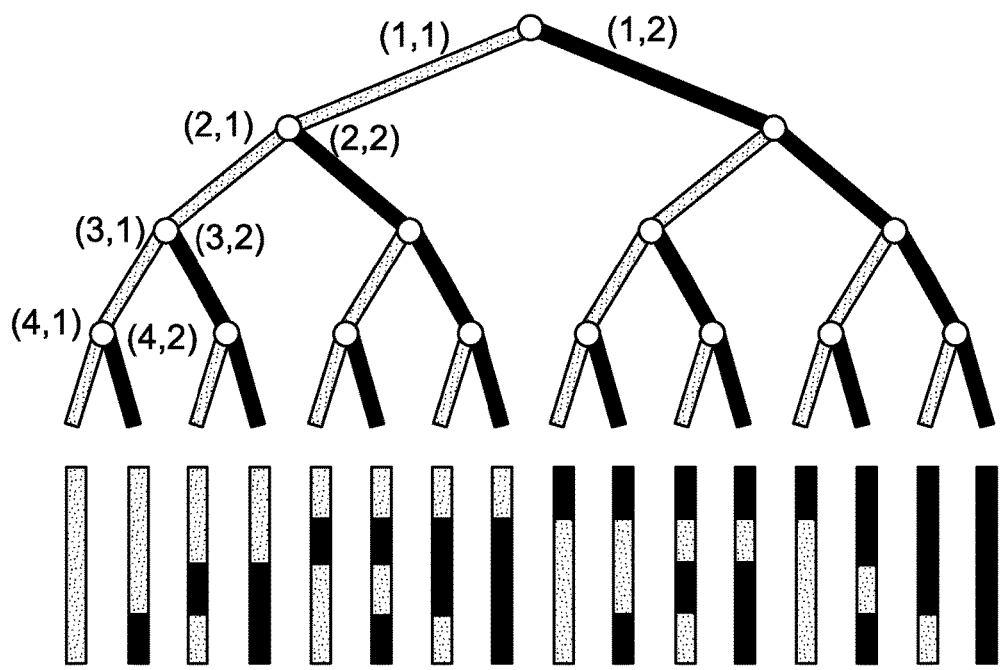
FIG. 9 shows a combinatorial space of ordered identifiers, according to an illustrative implementation.

FIG. 9 shows a tree diagram of a combinatorial space of 16 identifiers each constructed of 4 components from 4 layers, each layer comprising 2 components. Thus, each component is specified by a coordinate $(j, X_j)$, where j is an element of the set $\{1, 2, 3, 4\}$ and $X_3$ is an element of the set $\{1, 2\}$. Accordingly, all 16 identifiers are logically ordered according to the order of components in each layer.

The logical ordering of the identifiers can be further used to allocate and order digital information. Digital information can be encoded in nucleic acids that comprise each identifier, or it can be encoded in the presence or absence of the identifiers themselves. For example, a codebook can be created that encodes 4 bits of information in every contiguous grouping of 4 identifiers. In this example, the codebook could map each possible string of 4 bits to a unique combination of 4 identifiers (since there are 16 possible combinations of 4 identifiers, it is possible to store up to $\log_2(16)=4$ bits of data). As another example, a codebook can be created that encodes 6 bits of data in every contiguous group of 8 identifiers. In this example, the codebook could map each possible string of 6 bits to a unique subsets of 4 out of the 8 identifiers (since there are 8 choose 4=70 such subsets, it is possible to store up to floor($\log_2(70)$)=6 bits of data). These identifier combinations may be referred to as codewords, and the data that they encode may be referred to as words. Adjacent words within data may be stored in adjacent codewords among the logically ordered identifiers.

Figure 10:
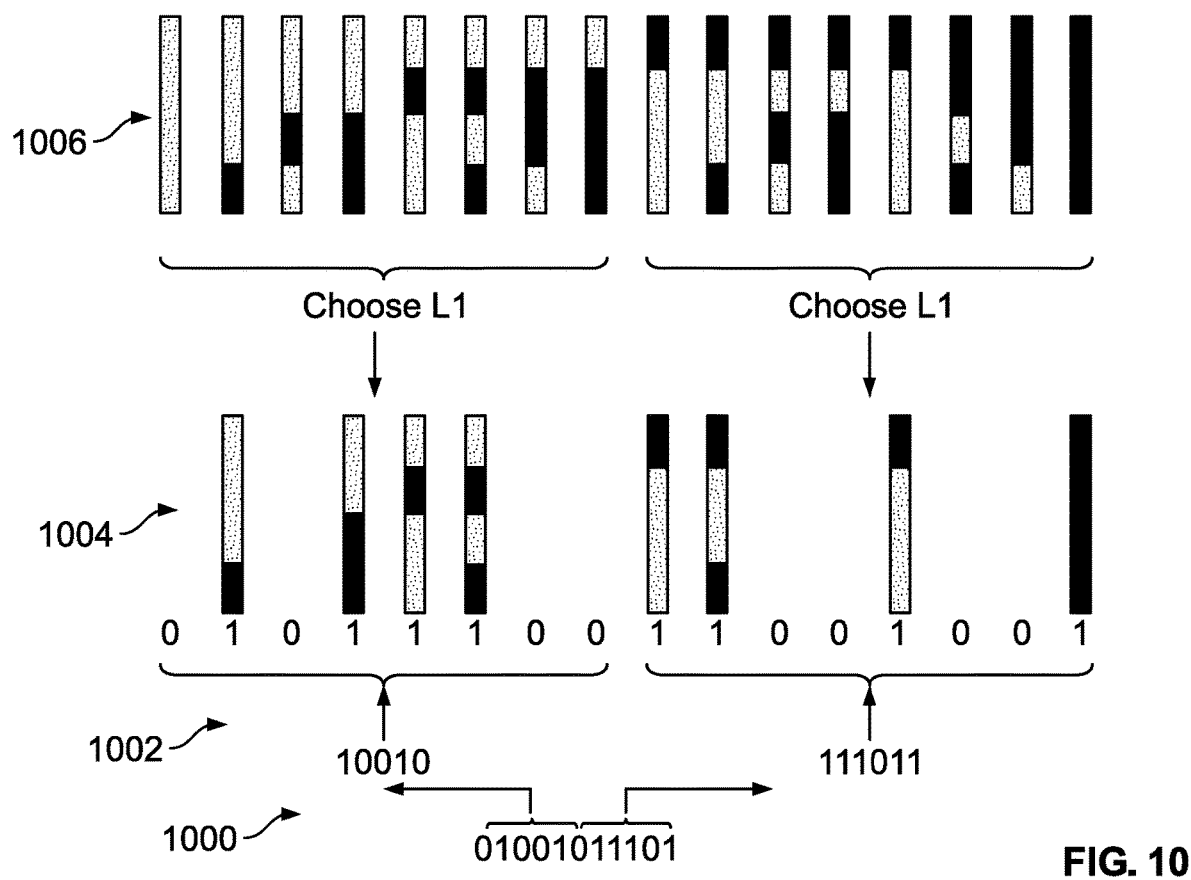
FIG. 10 shows translation of a digital string into a pool of identifiers using a codebook, according to an illustrative implementation.

FIG. 10 shows an example of translating a 12 bit digital string into a pool of identifiers using a codebook that maps 6 bit words to codewords comprised of 8choose4 identifiers (4 identifiers chosen from a group of 8). Codewords can be represented symbolically as bit strings where every bit position corresponds to an ordered identifier, where the bit-value of '0' represents the absence of the corresponding identifier in the codeword and the bit-value of '1' represents the presence of the corresponding identifier in the codeword.

Allocating and Accessing Blocks of Information

Figure 11:
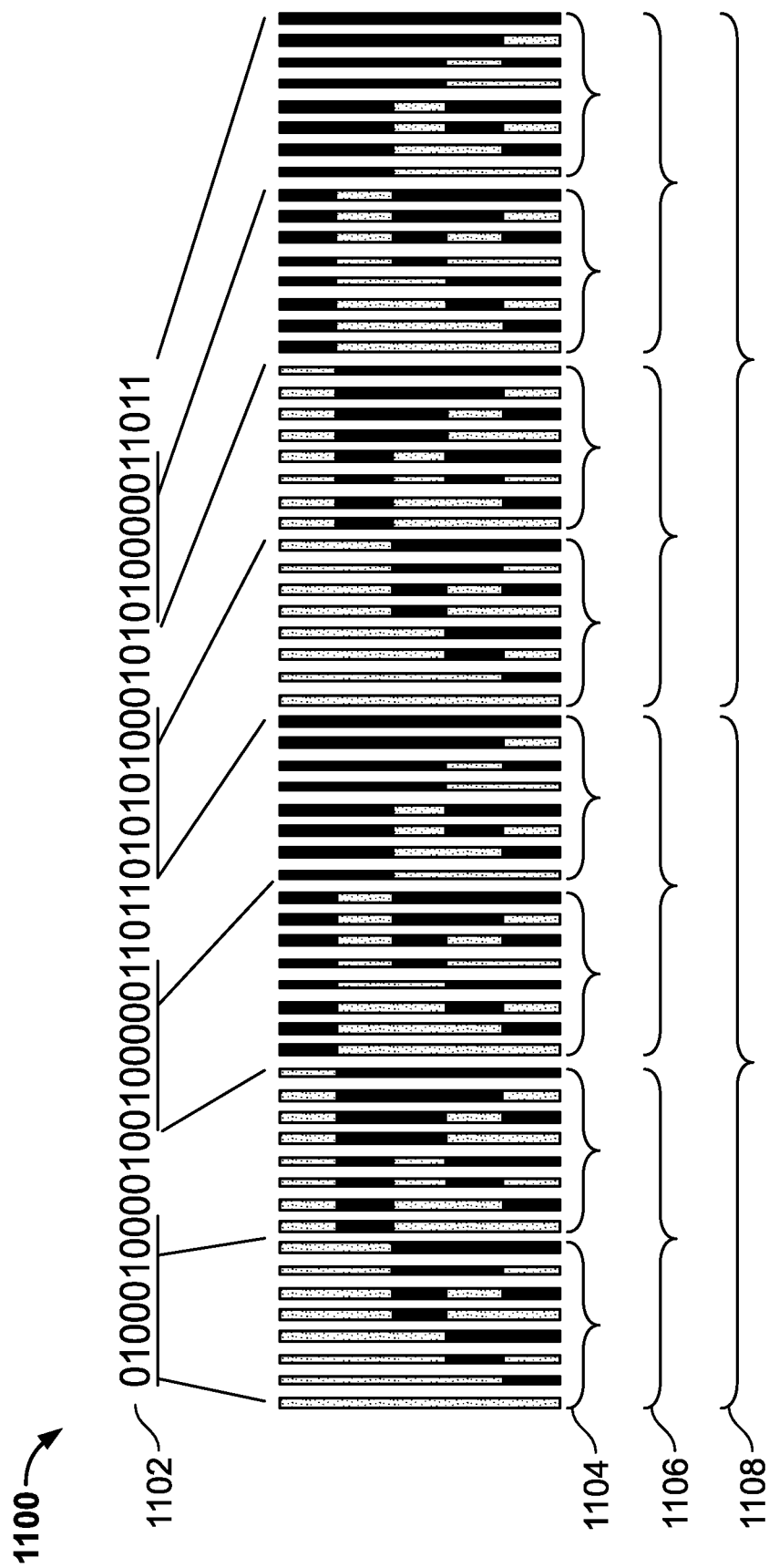
FIG. 11 shows encoding data across blocks and containers, according to an illustrative implementation.

Prior to encoding into codewords, ordered identifiers can be partitioned into blocks, where each block can contain multiple codewords. If multiple physical containers are used to store the nucleic acids, for example test tubes or per tubes, then multiple blocks can be partitioned using the same identifier space but in separate containers. FIG. 11 shows an example of how a space of 32 identifiers and 2 containers (1108) can be used to partition 4 blocks of data (1106), each of which is capable of storing 2 codewords (1104), each of which encodes 6 bits of data (1102). Blocks can be used to organize interpretable units of data. For example, a single codeword might give back the binary sequence that is not even enough to decode a single symbol of the encoded data (for example if the word size is 6 bits and the symbol size 8 bits), but a block may contain enough codewords to decode a standalone piece of the original information, even with included metadata for things like error protection and fixity. In the example of FIG. 11 above, each block was used to store each symbol of an input text string. But more generally blocks can be used to store numbers, strings, arrays, data objects, data files, and more. Blocks can be arbitrary size and can be assigned to data and identifiers arbitrarily, but when allocated effectively, they can be used as a powerful tool for querying relevant information without necessitating to read back an entire archive.

For example, on can choose to partition an identifier space into adjacent blocks of fixed size c codewords. In this way, the range of identifiers encoding the $g^{th}$ instance of a block, can be inferred as the range encoding codeword instances $(g-1)*c+1$ through $g*c$. These particular identifiers can then be readily accessed though chemical access programs which access only identifiers that share specified sets of components in common. These access programs work by selectively targeting and subsequently enriching, or selecting, identifiers with said specified sets of components using probes, for example with primers and PCR or affinity tagged oligonucleotides and affinity pull-down assays. Probes can be applied in a series of selection reactions, as in FIG. 8C, wherein each reaction targets an individual component. The output from one reaction can be used as input into another reaction. Because identifiers can be ordered by their components (as illustrated in FIG. 9), and further because blocks can be represented by a continuous range of these ordered identifiers, the identifiers that comprise a block are more likely to share components in common than if they were disparate. This reduces the complexity of the access programs needed to retrieve these identifiers. The reduced complexity can be further improved if the blocks are assigned to ranges of identifiers that form subtrees of the logical tree used to order them. Or in other words, if blocks are assigned to ranges of identifiers that exclusively share a set of components in common. In FIG. 11, a probe that targets a component in the first layer can be used to access each block. This is because each block (of each container) exclusively has a different component in the first layer.

Data Structures and Pattern Searching

Even though blocks of fixed length have finite storage capacity, the information contained within a block can refer to a subsequent block or multiple blocks from which to receive additional data. In this way, linked lists can be implanted in blocks of identifiers. Moreover blocks can represent trees or graphs. The structure of the tree or graph can be implicit by prescribing blocks that belong to different nodes of said tree or graph. For example, a first block can be reserved for a root node in a B tree, a second and third block for the second level nodes, and so on. The value of each node can be encoded in the block. And in this way, once can traverse a path in a tree to satisfy a query by accessing a block, decoding its node information, and using said information to calculate a subsequent block to access and decode (ie, a subsequent node to which to travel). Alternatively, the tree may have no prescribed structure besides a block for a starting node. From this block, and each block thereafter, the location of all blocks encoding neighboring nodes may be encoded along with the information within each node.

This structure can be used to create a trie, for example a suffix tree. A suffix tree can be used to look for patterns within a string of data. In a suffix tree, the blocks are configured to represent nodes of a suffix tree. The suffix tree is a trie, where every path from the root node to a leaf represents a suffix of a symbol string S. The edges of the trie represent substrings of symbols that comprise each path. A suffix tree can be represented in an identifier nucleic acid library where every block corresponds to a node in a suffix tree and contains information about its daughter nodes. For example, information about daughter nodes comprises the substrings of symbols that comprise the edges leading to each daughter node, and the locations of the blocks containing those daughter nodes. The root node can be a prescribed block, like the first block. Querying for the membership, count, or location of a pattern involves following a path along the suffix tree by accessing identifiers of the block corresponding to the root node, decoding the information contained therein, determining the location of the next block based on the information contained therein and the query pattern, and continuing the process until either no downstream blocks (or nodes) are left that will satisfy the corresponding query or until a lead node is reached. In the former case, the query pattern does not exist in the string S. In the latter case, the blocks corresponding to the leaf node can be configured to contain the count or locations of the query pattern.

Other approaches for looking for patterns include FM-index approaches and inverted indexes, each of which have block-based implementations using identifier nucleic acids. In an inverted index, there can be a block for each possible substring of a fixed length over a symbol alphabet that comprises a string S of symbols. Each block can contain information about the starting positions of the corresponding substring within S. The block IDs can correspond to the substrings, or they can correspond to the positions of the sorted substrings, such that the location of a block corresponding to a substring can be ascertained without additional information. A query pattern can be mapped to substrings of the inverted index that comprise it, and the blocks can be accessed and decoded. The positional information contained therein can be used to determine the count and locations of the query pattern within S. The inverted index need not be limited to substrings of fixed length. For example, it can also be used to represent the positions of words in a document, or across multiple documents.

Suitable data structures and search methods, such as the FM-index approach, are described in U.S. Application No. U.S. application Ser. No. 16/532,077 entitled "SYSTEMS AND METHODS FOR STORING AND READING NUCLEIC ACID-BASED DATA WITH ERROR PROTECTION", filed Aug. 5, 2019 and published as U.S. Publication No. 2020/0185057 (describing data structures and error protection and correction); and U.S. application Ser. No. 16/872,129 entitled "DATA STRUCTURES AND OPERATIONS FOR SEARCHING, COMPUTING, AND INDEXING IN DNA-BASED DATA STORAGE", filed May 11, 2020 and published as U.S. Publication No. 2020/0357483 (describing advanced data structures and protocols for access, rank, count, search, and extract operations), each of which is hereby incorporated by reference in its entirety.

Native Key-Value Stores With Parallel Queries

In some embodiments, the information needed to access a block of interest may be natively configured to a data object, such that the container of the block and the access program needed to retrieve it may be directly inferred from said data object without the necessity of accessing additional blocks. The data object may be referred to as a native key, the information contained within the corresponding block as a value, and their combination as a native key value (nkv) pair. In other words, a native key is the information encoded by an identifier sequence that may be used to access the identifier sequence. Whereas the value, in this context, is additional data that may be associated with the key and accessed with it.

Figure 12:
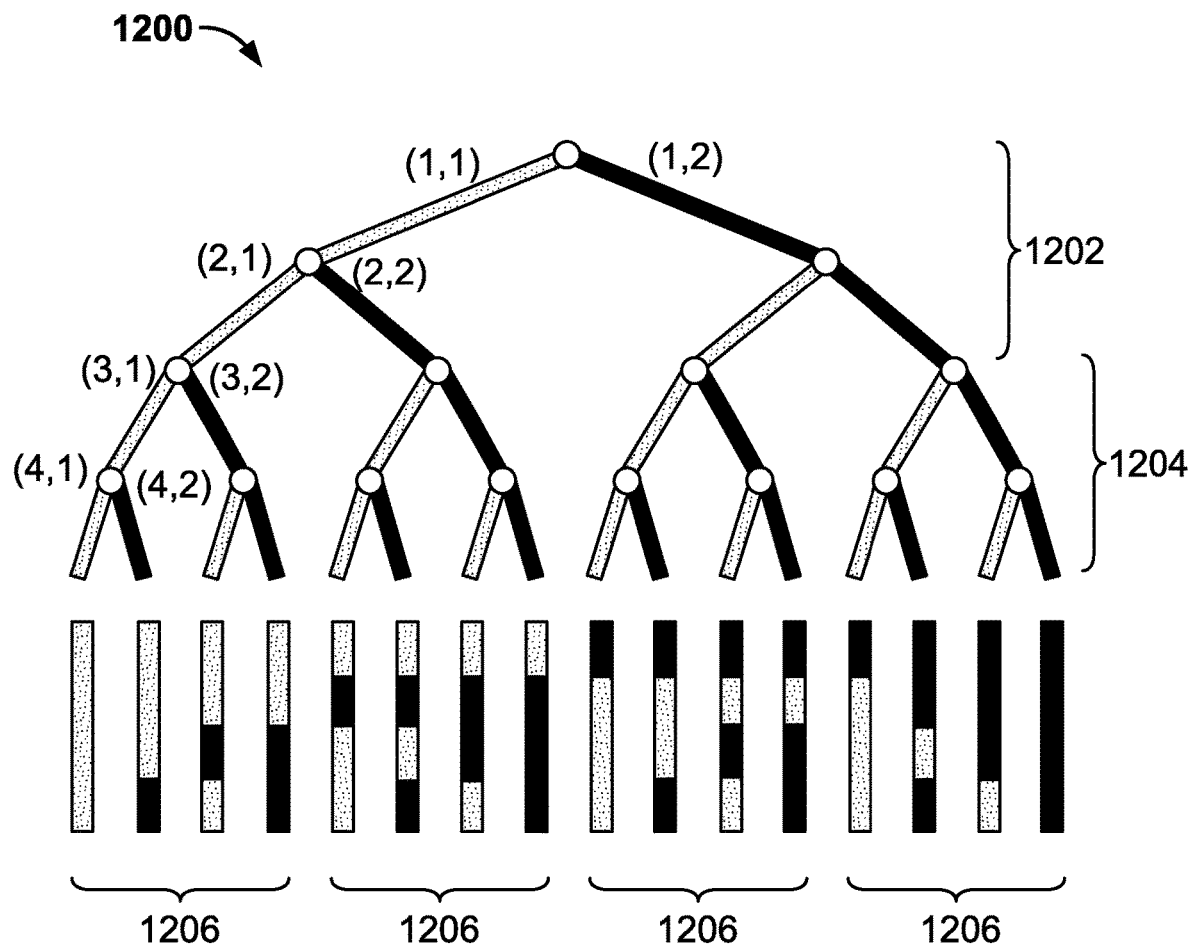
FIG. 12 shows storing native key-value pairs using identifiers, according to an illustrative implementation.

FIG. 12 illustrates an example of how to configure identifiers to store nkv pairs. In this example, certain layers of addressable components on an identifier are dedicated to storing the key, while the rest of the identifier is dedicated to storing the value. The key is stored in an identifier sequence comprising a component sequence from each of the "key layers" (1202 in FIG. 12). For example, if there are 8 key layers, and they all comprise two possible components, then there are $2^8$ possible keys. In other words, each key encodes 8 bits. As another example, if there are 16 key layers of 256 components each, then each key encodes $\log_2(256^{16})$=128 bits. The value for a key is contained in the block of identifiers with the corresponding components in their key layers. For example, if there are 16 possible identifiers with an associated key, then the value may be stored across two 8choose4 codewords, each encoding 6 bits, for a total of a 12-bit value. In the example of FIG. 12, there are two key layers 1202, each identifier having a 2 bit key, and there are 4-bit values in the remaining two layers 1204, together producing native key-value pairs as identifiers 1206.

The native key may be configured such that it is a symbol string with one position for each key layer, and one symbol value for each component in each key-layer. For example, if there are 8 key layers, and they each comprise 2 components, then the native key can be a string of 8 bits. As another example, if there are 16 key layers of 256 components each then the native key can be a string of 16 ASCII characters. Each symbol in the native key is an operand because it maps to an addressable component. A query formulation over the keys can be specified as a regular expression composed by logicals AND and OR, and by a primitive match-component operator, which is orchestrated in the form of a directed acyclic graph (DAG), the access program. The access program will specify the order in which chemical reactions will be executed over various containers containing the identifiers. For example, a range query can be performed for all keys containing a particular symbol value in the $2^{nd}$ and $4^{th}$ position by performing a series of two probe-bases reactions, one selecting for the corresponding component in the $2^{nd}$ key layer and one selecting for the corresponding component in the $4^{th}$ key layer. The accessed identifier blocks will contain only the values associated with the valid native keys. In this way, one can build a native key value store where query operations are performed over all keys simultaneously, without necessitating additional index information.

This method may be especially useful for storing native keys that are high dimensional and wherein common queries may be formulated as symbol selection operations. Such queries over such keys would be difficult to satisfy on conventional media, as the high dimensionality of the keys would make them impractical to index. But in identifier nucleic acids, architected as described above, the query could be fast and low cost. Such a method could be useful, for example, if the key is a bloomfilter, fingerprint, hash, or structural array of its corresponding data object and the query is one of symbol selection, or similarity or membership with respect to a reference object.

In one embodiment, the native keys could be records in a data table, the key layers can correspond to columns in the table, and the components of each layer can each correspond to a particular column value. Records can be queried using SQL-type commands to be compiled into an access program to be performed in DNA and select all identifier sequences that comprise a specified set of components. In some instances, the identifier sequence may be comprised entirely of key layers. In some applications, queries may involve counting the number of native keys that satisfy a certain property. Counting can be performed by sequencing, but it can be performed more natively with bulk read out methods such as fluorescence or absorbance. For example, one could determine the total amount of identifier molecules in a sample by doing qPCR with common edge primers or by using spectrophotometry, fluorimetry, gel electrophoresis, or plate reader assays. Because the expected number of identifier molecules per identifier sequences should be uniform, the bulk readout can be normalized by a standard sample (e.g. a sample comprised of a known number of identifier sequences) to find the number of unique identifier sequences (or the count), which can in turn be used to calculate a count of a number of native keys.

In some embodiments, the absolute count may not be of interest, and instead a relative count may be desired. For example, qPCR with a component specific primer (or probe) can be performed to find the relative fraction of identifier sequences in a sample that contain a particular component. The fraction may be relative to the entire population of identifier sequences in the sample or it may be relative to another subpopulation of identifier sequences that contain a different component. This type of data may be especially useful if the native keys are records, and the components of corresponding identifier sequences correspond to field values that comprise the records. One could then perform quick and effective queries of the form, find the number of records that contain data value x. Or as another, more complex example, of the records that contain data value x find the fraction that contain data value y. For example, of all the car accidents that happened in 1998 what fraction occurred in September. Bulk readout methods for absolute and relative counting may be faster and cheaper than DNA sequencing.

Because native DNA keys, for example records, may comprise components that represent data values, it follows that native keys that are semantically similar (share data in common) will also be similar in sequence. Such a property may be useful for performing similarity queries. For example, a query may be specified to find all records in a database that are similar to a reference record. The reference record may be converted into its corresponding identifier sequence and used as a probe in an identifier library to find all similar identifier sequences (corresponding to similar records). The reference identifier sequence may contain an affinity tag (e.g., biotin) such that it (and its binding partners) can be retrieved with an affinity pull-down assay (e.g., with immobilized streptavidin). The reference identifier sequence will be more likely to bind to other identifier sequences that share more sequences in common. The stringency of this binding, and therefore the stringency of the similarity query, can be controlled by using temperature and additives, such as salts. Increased temperature will increase the stringency and make it less likely that less similar identifier sequences will be returned by the query. The retrieved identifier sequences can be sequenced to determine their identity. Alternatively, the retrieved identifier sequences can be counted using the bulk readout methods described above. Such native similarity search may be less precise than conventional methods, but may be a lot faster and cheaper, especially for large databases of keys.

More broadly, any finite automata computation can be performed over native keys using access programs. This is because finite automata can be represented as regular expressions, and regular expressions can be reduced to the logical operators that comprise our query formulation. Generally, native key symbols can correspond to operands, and any logic can be performed over those operands with an access program. In an embodiment, native key symbols can correspond to numbers, and arithmetic can be performed over those numbers with an access program. For example, two 8-bit numbers that comprise native keys can be multiplied, and keys can be selected such that the product is between 412 and 500. Though this type of computation enables querying native keys using finite automata, it is not limited to this application, nor is it limited to Boolean output. Presented in the following section is a broader framework for multi-output computation over data objects comprised of operands.

Computing With Graph Programs (If-Then-Else)

An identifier library can be used to perform computations in parallel across multiple data objects in a data set. A computation derives the outputs related to the given inputs using a specified set of derivation rules. The set of all correctly related input-output pairs may be defined by some function, say $f$, which maps inputs, say X and Y, to their correct outputs, say Z and W. In this way, a computation implements a function $f$ if and only if when given some inputs (X, Y), it derives the same outputs as $f$(X, Y).

Figure 13C:
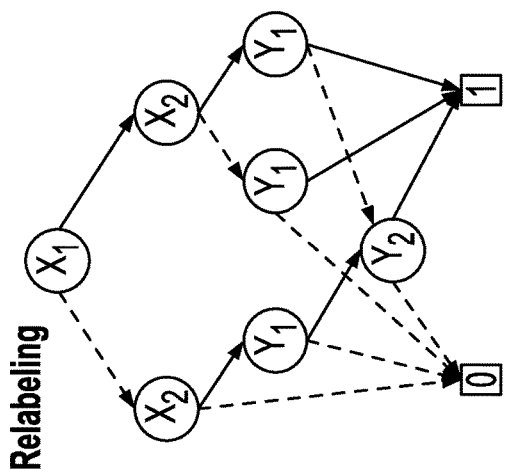

FIGS. 13A-13C illustrate how such a given function $f$ may be transformed into a set of rules amenable to implementation as computations with an identifier library. In the example shown in FIGS. 13A-13C, a function $f$ takes two 2-bit natural numbers X and Y and outputs their sum. The two-bit natural numbers are 0, 1, 2, and 3. Because the sum of two such numbers cannot exceed six, the output of $f$ can only produce at most three bits, which is a sufficient number of bits to encode the largest possible sum of six. The table in FIG. 13A shows a complete definition of $f$: for any pair of two-bit numbers shown in the top two rows labeled "Inputs," the rows labeled "Outputs" list the bit values $f$ outputs to correctly represent the addition operation. The three output bits are called the low bit, the high bit, and the carry bit, which are abbreviated as outputs L, H, and C, respectively.

To translate this tabular specification off into a ruleset amenable to DNA computing, a directed graph program is constructed and will direct the chemical operations to be performed on identifiers. Knuth's "The Art of Computer Programming Volume 4A: Combinatorial Algorithms Part 1" (which is hereby incorporated by reference in its entirety) provides theoretical details of directed graph programs, but here the process is adapted to the present disclosure's nucleic acid-based approach. The nodes in this graph are identifier libraries and arrows emanating from a node represent an operation performed on the library. Each node is labeled first by a bit string and later in the process by an input symbol. Each arrow is labeled first by an input of the function and later by a symbol of the alphabet. The graph program is constructed in two steps.

FIG. 13B illustrates the result of the first step called Factorization. In this step, a graph is constructed for each of the outputs C, H, and L, of $f$. To construct the graph, the bit string representing an output in the specification of the function is taken, and a node is created in the graph labeled by the bit string. For any node in the graph, including the first node just described, the steps given below are followed to construct the full graph: if a node is labeled by a bit string w that could be factored and rewritten as w=uv, where u and v are bit strings themselves of length half the length of w, then two new nodes are created in the graph and labeled with bit strings u and v respectively. An arrow from w to u is added with the label $x_i$=0, and an arrow from w to v is added with the label $x_i$=1, where i is the number of times this rule is applied, and $x_i$ is the i-th input bit accepted by the function $f$. Because the example shown uses a binary alphabet, a label string must be of length 2^n for some natural number n. The construction described, however, is extendible to any k-ary alphabet. In the k-ary case, the label is broken into k parts and with k arrows added, with k arrow labels $x_i$, one for each possible symbol in the alphabet. There are two caveats to the node creation rules. If a node labeled by u or v already exists in the graph, then it is reused instead of creating multiple nodes with the same label (this is referred to the "reuse rule"). If a new node is labeled by w=uv such that u=v, then labeling the node with w is foregone, and instead attempt to create a node with label u, the square-root of w (this is referred to as the "square" rule).

In FIG. 13B, consider the graph for output L for example. The label 0101101001011010 is factored into two new nodes labeled 01011010 01011010. Since this is the first application of the node creation rule, the arrows are labeled with $X_1$ as shown. Note, however, that this new node falls under the "square" rule since 0101101001011010= $(0101101)^2$. Therefore, creating that node is foregone and instead the "square root" node labeled by 0101101 is created. The root node is shown for pedagogical clarity and to prevent confusion in this special case where creation of the root node itself is prevented by the "square" rule.

The rule is reapplied to the new node 01011010, and two new nodes 0101 and 1010. The first new node 0101, however, factors into 01 and 01, so apply the "square" rule and instead create the node labeled 01. Because this is the third level of node creation, the arrows are labeled with $X_3$ as shown. Similar rules are applied to the node labeled 1010 to arrive at the final graph shown for output L. Using the same ruleset, graphs are constructed for all three outputs C, H, and L as shown in FIG. 13B. Note that three separate graphs are shown for pedagogical reasons: the three graphs may be merged so as to share reusable nodes and minimize the size of the program.

FIG. 13C shows the result of the second step in creating the graph program. In this step, the nodes and arrows are relabeled for brevity. The nodes are labeled with the input label on their outgoing arrows. Each outgoing arrow is relabeled with one of the possible values it can take from the symbol alphabet. Because there are only two possible values in this example, the dashed arrow is used to indicate the $X_i$=0 arrow and the solid arrow to indicate the $X_i$=1 arrow. All nodes except for the nodes labeled 0 and 1 are labeled with $X_i$. This label corresponds to the i-th bit of the input to the function $f$. Thus, a node labeled $X_1$ corresponds to the test of the input bit $X_1$. If this bit value is 0 in a given input instance, then the dashed arrow is followed out of the node and arriving at a new test. If the input bit value $X_1$ is a 1 in a given input instance, then the solid arrow is followed out of the node and arrive at a different test node. This process is continued until reaching the special 0 or 1 node, indicated by their square shape in FIG. 13C. These nodes encode the output of the computation: if a particular input, when tested through a graph program as described above leads to a 0 node, then it means that the output derived from this input instance is 0. Likewise, if an input leads to a 1 node, then it means that the output derived from this input instance is a 1. In this way, for any input $X_1X_2Y_1Y_2$, the graph program for outputs C, H, and L, derives a well-defined 0 or 1 output. Taken together, these graph programs implement the sum function specified FIG. 13A.

Figure 14B:
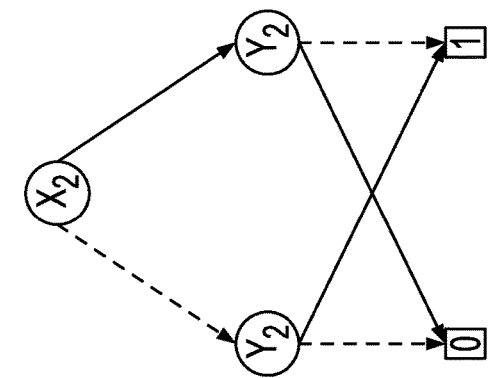
Figure 14B:
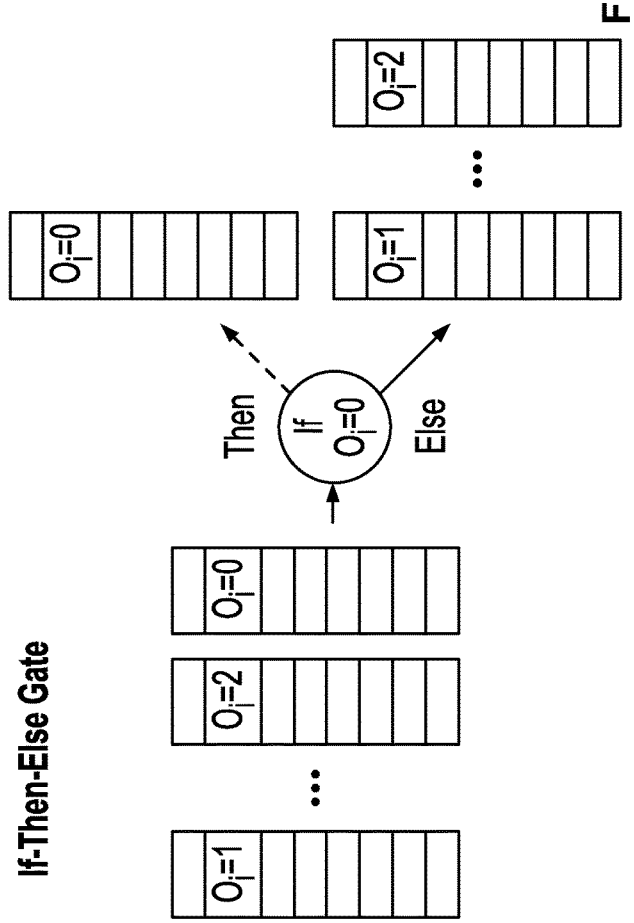
Figure 14A:
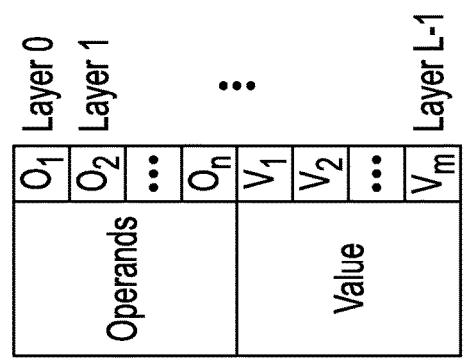

FIGS. 14A-14F illustrates how a computation may be carried out on a data set using the graph programs constructed in FIGS. 13A-13C. FIG. 14A shows the schematic of an identifier constructed via concatenation of components. In this example, an identifier comprises five components, each component chosen from a distinct layer. To enable computation with such identifiers, in this example one or more layers to carry the data are defined as operands for the computation. In this abstract example, the operand portion of the identifier, called the operand register, is denoted as $O_1O_n$. Additional layers can encode a data value that is not part of the computation but is otherwise associated with an operand register. These additional layers, which are collectively called the value register, are denoted as $V_1$-$V_m$. The operands and the additional data values, as well as the allocation of layers to each, may be arbitrarily chosen by the programmer. For example, the two-bit input numbers $X_1X_2$ and $Y_1Y_2$ described in FIGS. 13A-13C could be stored as operands in an identifier for the addition computation, and the rank of the pair of two-bit numbers in the data set could be stored in the value register. Identifier sequences of this structure are a type of nkv as previously defined, where the operands are the native keys symbols that form the native key, the operand register is made up of key layers, and the additional layers store the associated value. Generally, the value register can store any type of data. In the example of FIG. 14, the value register stores a rank. In another embodiment, the value register, can store a compressed or hashed representation of the operands. In another embodiment, the value register can store a key that is subsequently used to access more data.

FIG. 14B shows the schematic of a chemical technique used as the basis for computations. This chemical technique is referred to herein as the "if-then-else" (ITE) gate. This gate takes as input an identifier library and produces as output one or more identifier libraries. The ITE gate is defined by a parameter t called the "test layer" which defines the layer examined by the gate. The set of components $L_t$ that can possibly occur in layer t is partitioned (into disjoint sets whose union forms $L_t$) by the programmer into a collection of $n_t$ sets $L_t^j$, j=0, . . . , $n_t$-1. An output library is created for each set in the collection and is labeled with that set.

The ITE gate operates as follows. The gate is presented with an input library of identifiers. These identifiers are tested by the gate by examining the component in layer t of each identifier. If the component in layer t of an identifier is c, and c is defined by the programmer to be a member of the set $L_t^j$, then that identifier is sorted into the output library labeled $L_t^j$. In this way, an ITE gate testing layer t, classifies identifiers in the input library into output libraries based on the component in its layer t. FIG. 14B illustrates an example where the ITE gate tests layer 1 and sorts identifiers into libraries based on whether or not the identifier has component 0 in layer 1. In this example, assuming there are three possible components—{0, 1, 2}—in layer 1, the output libraries are labeled $L_1^0$={0} and $L_1^1$={1, 2}.

FIG. 14C shows an example data set to be used in a computation. Consistent with the example function described in FIGS. 13A-13C, in this example, the data set comprises pairs of two-bit natural numbers X and Y, arranged in a given order denoted by their rank in the data set. As described above, each data object in the data set is mapped to one or more identifiers. In this example, the pair of natural numbers X and Y is mapped to the operand register of an identifier, and the rank of the data object to the value register of the identifier. In this example, each input bit is mapped to a layer of the identifier, and each layer can have exactly two possible components representing the binary alphabet. FIG. 14D shows the identifier library created from the data set shown in FIG. 14C. Without loss of generality, in this example, that value register is assumed to comprise a single last layer of the identifier, and that the layer has a sufficient cardinality to encode the rank of any object in the data set.

FIG. 14E illustrates how the graph programs constructed in FIGS. 13A-13C may be combined with the ITE gate described in FIG. 14B to build an ITE gate graph program to perform a parallel sum computation on the example dataset shown in FIG. 14C. Except for nodes labeled by 0 or 1, each node of a graph program is implemented as an ITE gate. The test layer of the gate is set to the layer of the operand register containing the input bit labeling the node. For example, in the graph program for Output C in FIG. 14E, the first ITE gate tests for layer 0, because it holds bit $X_1$ of the input, as directed by the label for this node. The next two ITE gates test layer 1 of the identifier, because it holds bit $X_2$ of the input as directed by the labels those two nodes, and so on. In this example, it is assumed that the test layer always contains exactly two possible components, labeled 0 and 1, and thus, there are always exactly two output libraries, labeled $L_t^0$={0} and $L_t^1$={1}. For clarity, writing the labels is foregone, and the convention previously described is adopted, using dashed arrows to point to the output library {0} and a solid arrow to point to the output library {1}. When a node in the graph program has more than one incoming arrow, the ITE gate implementing the node has more than one input library. In this case, it is assumed that the input libraries are pooled to form a single input library containing the union of the identifiers present in all of the input libraries. Nodes labeled by 0 or 1 (rather than input bits) are output nodes: the computation terminates when all ITE gates have finished processing the input libraries presented to them and have produced their output libraries, culminating in output libraries represented by the output nodes. In this example, there are two output nodes and therefore two output libraries representing two output symbols, 0 and 1.

The computation proceeds in the following way. Consider the graph program constructed to compute output L in FIG. 14E. The identifier library shown in FIG. 14D is presented to the first ITE gate in of this program. The gate being labeled by $X_2$, tests layer 1 of each identifier in the input library, in parallel, and sorts them into two output libraries, {0} and {1}, defined by the component present in layer 1. In this example data set, three identifiers (with values 0, 2, and 4) contain component 0 and four identifiers (with values 1, 3, 5, and 6) contain component 1 in layer 1. Accordingly, the ITE gate classifies these identifiers into the two output libraries produced by the first ITE gate as shown in FIG. 14E. These output libraries in turn serve as input libraries to the next ITE gates. The next set of ITE gates are labeled Y2 and thus test layer 3. From the identifiers with values 0, 2, and 4, only identifier with value 0 has component 0 in the test layer. Therefore, it is classified into the output library labeled 0. From the identifiers with values 1, 3, 5, and 6, identifiers with values 3, 5, and 6 have component 1 in the test layer. These identifiers are classified by the other ITE gate into the output library 0. As a result, output library 0 comprises identifiers with values 0, 3, 5, and 6. By a similar sequence of steps, output library labeled 1 comprises identifiers with values 1, 2, and 4. FIG. 14E shows the output libraries constructed by each of the three graph programs for each output of the function $f$ specified in FIG. 13A. Because the graph programs were constructed by factorizing the specification of the function $f$, the identifiers classified into each output class (0 or 1) correctly implement the definition of $f$.

From the output libraries constructed by the three graph programs shown in FIG. 14E, the output of the function $f$—the sum of a pair of two-bit natural numbers—on each data object in the data set can be extracted. The output of the function $f$ for any input comprises three bits: the carry bit, the high bit, and the low bit. The low bit output for the example data set is extracted as follows. The output nodes of the graph program for output L contain two output libraries, labeled 0 and 1. The output library labeled 0 contains identifiers for which the low bit output must be a 0, as defined by the graph program. Similarly, the output library labeled 1 contains identifiers for which the low bit output must be a 1. To report the output, the value register of the identifiers in the two libraries are read. This may be done using a standard nucleic acid sequencing chemical method. For each value found in the output library 1, a 1 output is reported as the low bit output. This is shown as a "1" entry in the L-row of the Output L table shown in FIG. 14F. The remaining values must therefore be in the other output library, and hence for these values the low bit output is entered to be a 0. In this way, all three output bits for all the data objects in the data set can be retrieved. The output so extracted for each of the two-bit number pairs, when checked against the specification of $f$ shows that the program correctly computes the sum of the numbers. In this way, any function may be implemented using identifier libraries and graph programs.

Data Storage and Computation With Copy Number Manipulation

In the preceding, strategies were presented for storing data using identifier sequences and computing on the data by manipulating the presence or absence of identifier sequences. Alternatively, or in addition to this method of data storage and compute, data can also be stored in the number of molecules, or copy number, of a particular identifier sequence in an identifier library. For example, an entire identifier sequence can correspond to a key and the value of the key can correspond to the copy count of the identifier sequence in one or more identifier libraries.

Copy count may be difficult to control and may be inherently imprecise depending on the method used to encode it, manipulate it, and measure it. To circumvent these limitations, one may encode data values with expected copy count (ECC) instead of actual copy count and accept that the representation is approximate or fuzzy. Although copy count is discrete, ECC is continuous and thus enables representation of more values within a range of copy counts. An analog mapping can be defined such that numerical data values are represented by a proportional ECC. For example, if the constant of proportionality is 100, then the value 2 would be represented by an ECC of 200, the value 2.5 would be represented by an ECC of 250, the value 2.755 would be represented by an ECC of 275.5, and so on. Such an encoding scheme is referred to as "analog encoding."

Figure 16:
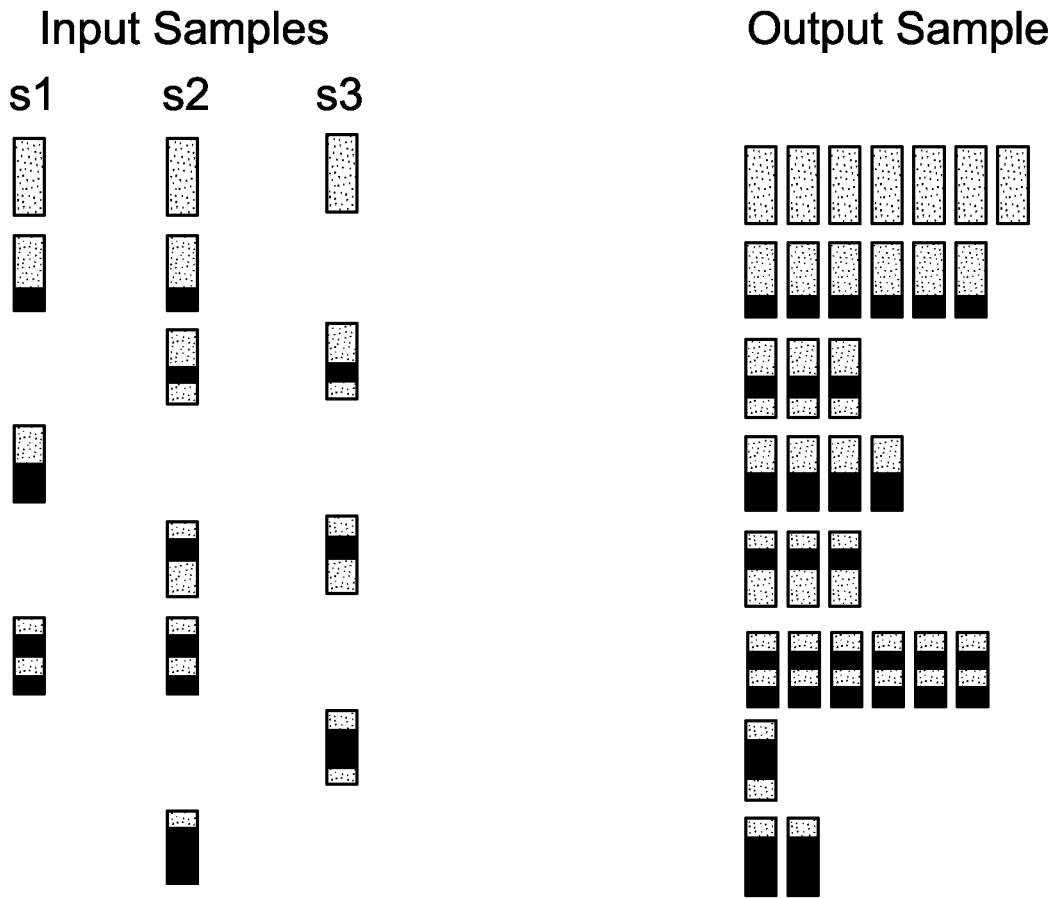
FIG. 16 shows an example protocol for performing computation on numerical values encoded with identifiers, according to an illustrative implementation.

The benefit of analog encoding is that it enables computation with native sample operations such as mixing, aliquoting, and PCR. Table 1 provides and overview of these sample operations and their logic. Mixing two samples, s1 and s2, performs addition where the two numbers being added are the respective numerical values of an identifier sequence in both samples. Aliquoting from a sample, s1, performs multiplication by a number less than one (a "fraction") where the fraction corresponds to the fractional volume of the aliquot (the volume of the aliquot divided by the volume of the sample s1 from which it was derived). PCR performs multiplication by a power of 2 where the power of 2 corresponds to the number of PCR cycles. For example, one PCR cycle corresponds to multiplying by 2, two PCR cycles corresponds to multiplying by 4, three PCR cycles corresponds to multiplying by 8, and so on. FIG. 16 demonstrates examples of logical operations performed over analog encoded data stored by an identifier sequences across two samples, s1 and s2.

TABLE 1

Sample operations and logic for computation in analog encoding.

| Sample Operation | Explanation | Logic |
|---|---|---|
| mix(s1, s2) | Mix the entirety of two samples | $x1_i + x2_i$ for all i |
| pcr(s1, y) | PCR a sample for y cycles where y is an integer | $2^y \cdot x1_i$ for all i |
| aliquot(s1, z) | Aliquot a fraction z of a sample volume where z is less than 1 | $z \cdot x1_i$ for all i |

For samples containing multiple identifier sequences, the logic performed by the sample operations are performed over all identifier sequences in parallel. Moreover, the sample operations described above are composable as they take samples as inputs and produce samples as outputs that can be further operated on. For example, multiplication by an arbitrary positive number can be accomplished by performing PCR for y cycles and aliquoting a fractional volume z since any positive number can be represented by $z \cdot 2^y$ for some fraction z and some integer y. Because of this, any arbitrary linear function with positive coefficients can be represented by composing these sample operations.

In an embodiment, one can encode a vector $x = [x_1, x_2, \ldots, x_N]$ by storing the value of each element in a different sample, but in the same identifier sequence across each sample. A linear function (or linear combination) $c_1 x_1 + c_2 x_2 + \ldots + c_N x_N$ can be applied to the vector by computing each multiplication term with a combined aliquot-PCR operation over the respective sample, and then adding the terms by mixing all of the output samples together.

FIG. 15 shows various protocols for performing the operations of Table 1 on two example samples, s1 and s2. s1 encodes the numerical value 4 using 4 identifiers, and s2 encodes the numerical value 3 using 3 identifiers. The first protocol involves performing 2 cycles of PCR on sample s1, producing an output sample of numerical value 16 represented by 16 identifiers. The output is determined by the logic of the numerical value 4 multiplied by 2 to the power of 2, for the 2 cycles of PCR. The second protocol involves taking a half aliquot of sample s1, producing an output sample of numerical value 2. This follows the logic of dividing the numerical value 4 of s1 by 2, due to the half aliquot splitting of the sample. The third protocol involves mixing samples s1 and s2, producing an output sample of numerical value 7. Mixing represents the addition of numerical values encoded according to this scheme, so it logically follows that the output is the sum of the values of samples s1 and s2. The fourth protocol of FIG. 15 shows an example of a linear function performed over the data encoded in an identifier sequence across two samples, s1 and s2. The linear function is a combination of mixing, PCR, and aliquots of both samples.

Not only can each multiplicative term and each addition in a linear function be performed in parallel, but the function itself is performed over multiple vectors simultaneously if multiple identifier sequences exist in the samples, each encoding their respective vector. For example, with a trillion identifier sequences, one can encode up to a trillion vectors. If each vector is 100 elements, then this can be encoded across 100 samples. FIG. 16 illustrates an example of a linear function being performed over 9 vectors in parallel. Each vector is 3 elements, with each element stored in a different sample. In this example, the data is originally encoded in binary with each identifier sequence in each sample either being present or absent. FIG. 16 demonstrates a linear function that converts the binary data across the three input samples into an analog, or unary, value in a single output sample. The function treats the data in sample s3 as the least significant binary digit, the data in sample s2 as the proximal binary digit, and the data in sample s1 as the most significant binary digit, and so it adds the data in sample s3 to 2x the data in sample s2 and then adds that to 4x the data in sample s1. In terms of sample operations, the protocol for this logic looks like mix(mix(per(s1, 2), pcr(s2,1)), s3). For example, the binary number 111 stored in the first identifier sequence gets converted to the analog value 7, the binary number 110 stored in the second identifier sequence gets converted to the analog value 6, the binary number 011 stored in the third identifier sequence gets converted to the analog value 3, and so on. As depicted on the bottom of FIG. 16, the data in the samples can be abstracted as a matrix where every row is a vector encoded by an identifier sequence and every column is data encoded by that identifier sequence in a sample. Likewise, the coefficients of the linear function can be represented as a column vector that gets multiplied to the matrix. The column vector has values 4 (representing the 2 cycles of PCR applied to sample s1), 2 (representing the 1 cycle of PCR applied to sample s2), and 1 (representing sample s3). The columnar output vector is encoded in the output sample. Though not illustrated, multiple linear functions can be performed over the sample data to produce multiple output samples. This would be the equivalent of multiplying two matrices two make an output matrix.

The method of digital to analog conversion illustrated in FIG. 16 is extensible to digital data stored in any format (for example, not just base 2 but also base 3, base 4, decimal, and so on). With this strategy, data can be encoded digitally and then converted to analog encoding (expected copy count representation) for computation and read out. For example, consider a 3-element vector $[x_1, x_2, x_3]$ of 3 bit numbers where the number $x_i$ is represented by $b_{i1}b_{i2}b_{i3}$. This may be represented by binary encoded (presence or absence) identifier sequences across 9 samples. Where the first three samples represent the first element, the second 3 samples represent the second element, and the third three samples represent the third element. A linear function $c_1x_1+c_2x_x+c_3x_3$ on the vector would then be compiled into a linear function $c_1(4b_{11}+2b_{12}+b_{13})+c_2(4b_{21}+2b_{22}+b_{23})+c_3(4b_{31}+2b_{32}+b_{33})$ on the binary representation which would then be performed as a protocol with sample operations over the samples containing the binary data.

The sample operations above cannot perform linear functions with negative coefficients. If the data is represented in binary, then a term with a negative coefficient in a linear function can be converted to a term with a positive coefficient using the following formula: $-c_ix_i=c_i(1-x_i)-c_i$. The $(1-x_i)$ is equivalent to $x'_i$, the complement of $x_i$ when $x_i$ is a bit. So it follows that any negative term in a linear function (over binary data) can be converted to a positive term by using the complement of the binary digit in the term. For example $c_1x_1-c_2x_2-c_3x_3$ can be converted to $c_1x_1+c_2x'_2+c_3x'_3-(c_1+c_2)$. It follows that any mixed-sign linear function can be converted to a positive sign linear function minus a constant. In order to perform this linear function conversion on a binary dataset (without prior knowledge of which terms in the linear function will be negative), the complement of the data must be stored along with the original data. In other words, for each sample s created with the presence of a set of identifier sequences A and the absence of another set of identifier sequences B there must be a complement sample s' created as well that contains the presence of the set of identifier sequences in set B and the absence of identifier sequences in set A. Once the linear function is in a form with positive sign terms, it can be executed using sample operations described above (see Table 1 and FIGS. 15-16). The constant term does not depend on the data, and so it can be subtracted from the results after it has been read out of DNA form, but for some applications the constant term may not even matter. For example, if the linear function is a scoring function then the constant will not affect the rank order of the results. For example, if there are a trillion vectors and the linear function is designed to score the vectors according to a trained model, then the constant term will not affect which vectors score higher than others.

The linear functions applied to the data can be models designed to identify target vectors that have a certain property. For example, a linear function can be designed to convert target vectors into a high score and non-target vectors into a low score. Because those scores are represented by ECCs, Identifier sequences encoding higher scores will be more abundant in an output sample than identifier sequences encoding lower scores and therefore random sampling from the output sample with DNA sequencing will be more likely to return identifier sequences represented by vectors that score higher in the model. The vectors themselves may be compressed representations of larger data objects that are stored elsewhere. For example, they may be hashes, bloom filters, signatures, fingerprints, or structural arrays derived from the original data objects. The original data objects for high scoring vectors can be retrieved using the associated identifier sequence (or a derivative thereof) as a key.

Because the operations described herein perform linear functions, they may be limited in their ability to enrich target identifier sequences (representing target data objects) over non-target identifier sequences. Subsequent application of non-linear functions, such as activation functions, may further enrich target sequences. This is akin to how neural networks function to create complex behavior, such as classification. Generally in neural networks, a layer of "neurons" calculates a weighted sum of inputs (equivalent to linear functions), and then those values (the weighted sums at each neuron in the layer) are added together after applying a non-linear function to each of them. The non-linear function in this context is called an activation function as it "activates" the signal from certain neurons. The non-linearity is crucial for activation because it effectively suppresses signal from neurons with output values that fall below a certain threshold.

The formation of double stranded DNA from complementary single strands is a dimerization process and therefore has a super-linear dependence on the concentration of DNA molecules. Eqns. 1-8 provides a model for dimerization of single stranded DNA (species Z) to form double stranded DNA (species Y). Mass action kinetics are used to derive the concentration of double stranded DNA at steady state ([Y]) as a function of the total amount of DNA [X].

Eqn. 1 represents the equilibrium reaction of dimerization, governed by the the rate of double stranded DNA degradation into single strands ($\delta$) and the rate of duplexing ($\alpha$). Eqn. 2 represents the rate of change in the concentration of double stranded DNA [Y] based on the kinetics of Eqn. 1. At steady state, Eqn. 2 is equal to zero as shown. At steady state, solving Eqn. 2 for the concentration of double stranded DNA [Y] yields Eqn. 3. The parameter K is the ratio of the rate of double stranded DNA degradation into single strands ($\delta$) and the rate of duplexing ($\alpha$) (in short, K=$\delta/\alpha$). The total amount of DNA [X] is equal to the sum of the amounts of single stranded DNA [Z] and double stranded DNA [Y], as shown in Eqn. 4. Substituting Eqn. 4 into Eqn. 3 for [Z] gives Eqn. 5. Expanding Eqn. 5 produces the quadratic equation Eqn. 6 in standard quadratic form which can be solved for [Y] to get Eqn. 7. Eqn. 7 has two solutions, but one solution has [Y]>[X] which is not possible, so only one feasible solution is shown in Eqn. 7.

$$2Z \underset{\delta}{\overset{\alpha}{\rightleftharpoons}} Y \qquad \text{Eqn. 1}$$

$$\frac{d[Y]}{dt} = \alpha[Z]^2 - \delta[Y] = 0 \qquad \text{Eqn. 2}$$

$$[Y] = K^{-1}[Z]^2 \qquad \text{Eqn. 3}$$

$$[X] = [Y] + [Z] \qquad \text{Eqn. 4}$$

$$[Y] = K^{-1}([X] - [Y])^2 \qquad \text{Eqn. 5}$$

$$[Y]^2 - (2[X] + K)[Y] + [X]^2 = 0 \qquad \text{Eqn. 6}$$

$$[Y] = \frac{2[X] + K - K(1 - 4[X]/K)^{1/2}}{2} \qquad \text{Eqn. 7}$$

$$[Y] = \frac{[X]^2}{K} \qquad \text{Eqn. 8}$$

Figure 17A:
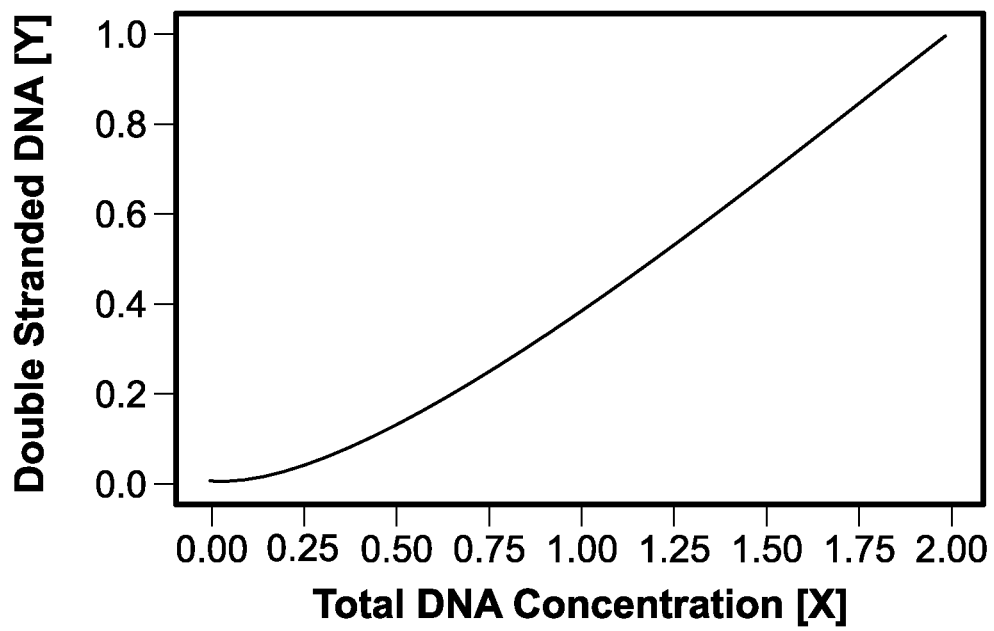
FIGS. 17A-17B are a plots of Equation 7 over different domains, according to an illustrative implementation.
Figure 17B:
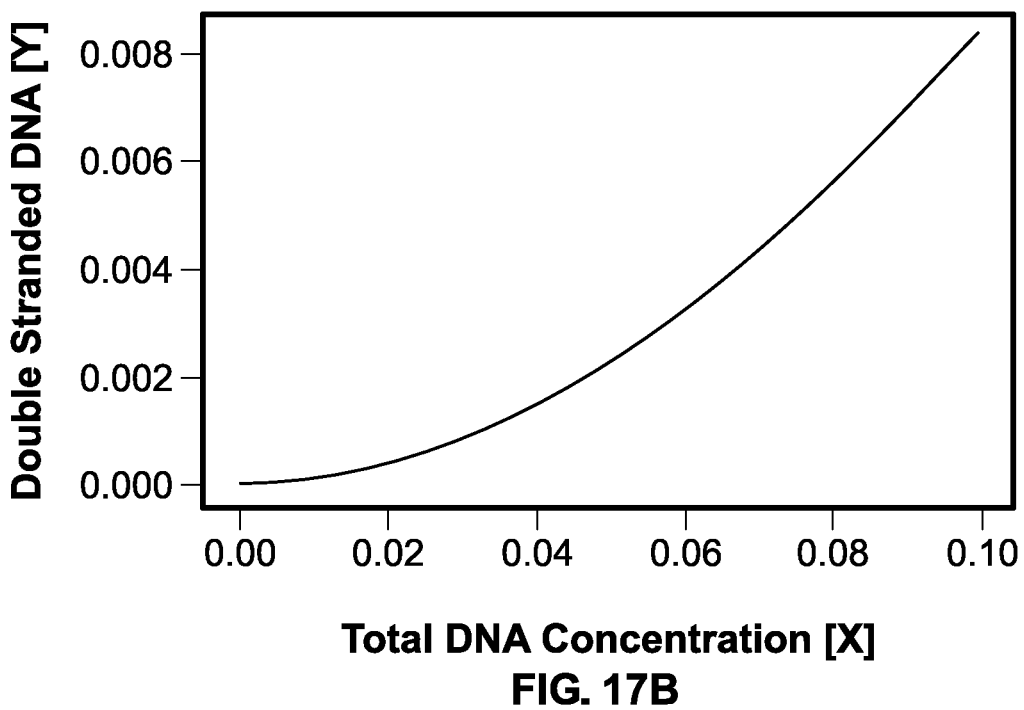

Eqn. 7 is non-linear but has different behaviors in different regimes. For [X]>K, [Y] is approximately linear to [X]. When the total amount of DNA [X] is much less than the rate constant K ([X]<<K), [Y] is quadratic in [X] and Eqn. 7 may be approximated by Eqn. 8 by using a second order approximation. FIGS. 17A and 17B support this approximation with a plot (FIG. 17A) of the relationship between [Y] and [X] as described by Eqn. 7, and an additional zoomed in plot (FIG. 17B) of a regime where [X]<<K (approximated as the range of 0 to 0.1 for [X]), where quadratic behavior in [X] is observed.

This non-linearity can be exploited to increase the copy count difference between identifier sequences in a sample. It can favorably enrich identifier sequences with higher copy counts, thus effectively suppressing identifier sequences with lower copy counts, much like an activation function in a neural network. This in turn will make identifier sequences with higher copy counts more likely to be sequenced if the sequencing process only covers a small sample size of the total sample. The non-linear function can also be applied repeatedly. Literature (such as Livni, R. et al. "On the Computational Efficiency of Training Neural Networks", arXiv:1410.1141 [cs.LG]; which is hereby incorporated by reference in its entirety) has shown that quadratic equations like the one demonstrated in Eqn. 7 can be used effectively as activation functions in a neural network when applied repeatedly. The quadratic approximation equation from Eqn. 8 or the entire exact equation can be used to train a neural network model. This model can then be applied to data stored in DNA using the operations described above.

In order to faithfully exploit the non-linear relationship in Eqn. 7, it is necessary to perform a sample operation that selectively extracts double stranded DNA from a sample. In one embodiment this may be accomplished with chromatography strategies like gel electrophoresis. In another implementation, this may be accomplished by mass spectrometry. In another implementation, this may be accomplished by flow cytometry or another fluorescent sorting technique using double-stranded DNA specific dye. In another implementation, this may be accomplished with membrane capture or affinity capture techniques, such as with silica beads or columns. Prior to double stranded DNA selection the sample must be given time to equilibrate (reach steady state) as per the model assumptions in Equations 1-8. The non-linear regime occurs with [X]<<K which can be forced by either diluting the sample to make [X] smaller. Alternatively, one could make K larger, for example by increasing the temperature of the sample or adding substances that interfere with duplexing.

Encoding Via Longitudinal Striping

In FIGS. 1A-1B, a scheme called "data at address" was described, hereon referred to as "longitudinal encoding", for encoding a data object such as a "byte-value" along an identifier. In this section, the longitudinal encoding scheme is extended to allow encoding a data object comprising multiple byte-values along identifiers in multiple identifier libraries, hereon referred to as longitudinal striping. Provided herein are methods for retrieving a part of a data object encoded longitudinally from a target library, given a part of said data object in a query library, and methods for using a longitudinally encoded dataset for computation in a "graph program" previously described above. Together, these aspects enable computations on larger data objects using graph programs by removing the limit on the length of a computable data object which was previously defined by the longitudinal data encoding capacity of one identifier.

In this section, identifiers, as described in relation to FIG. 12, comprise layers encoding a key that distinguishes data objects from each other and layers encoding the operands constituting the data object. Identifiers may comprise a total of L layers, M of which are allocated to the key and N of which are allocated to the data, where M+N≤L. Extending the previous description for encoding byte-values along identifiers (see U.S. Pat. No. 10,650,312, titled "NUCLEIC ACID-BASED DATA STORAGE", filed Dec. 21, 2017, which is incorporated by reference in its entirety), in this section, a data object comprising multiple byte-values is first divided into P parts, each part containing no more than K byte-values. The positive integer K is chosen as follows: if an identifier comprises N operand layers, each layer containing one of C possible components, then any value≤ L·⌊log$_2$C⌋/8 may be chosen for K. Given a data set comprising D data objects, each of length at most T bytes, in some embodiments, each data object is divided into at most $P = \lceil T/K \rceil$ parts. (If a data object contains less than P parts, then the end of the object may be indicated by encoding a special delimiter symbol such as "−") The set of the i-th parts of the data objects is called the i-th stripe of the dataset, and any subset of a stripe, a substripe. In some embodiments, the dataset is encoded using P identifier libraries $L_1, \ldots, L_P$ each containing identifiers of rank $1, \ldots, R$, $(R \geq D)$ in the following way: the j-th part $(0 < j \leq P)$ of the r-th data object is encoded longitudinally in the operand register of an identifier of rank in the interval $[C^N r, C^N (r+1)−1]$ in the j-th library. Data objects encoded in this manner are referred to as longitudinally striped across P identifier libraries, with each library encoding one of P stripes of the data set.

Figure 18:
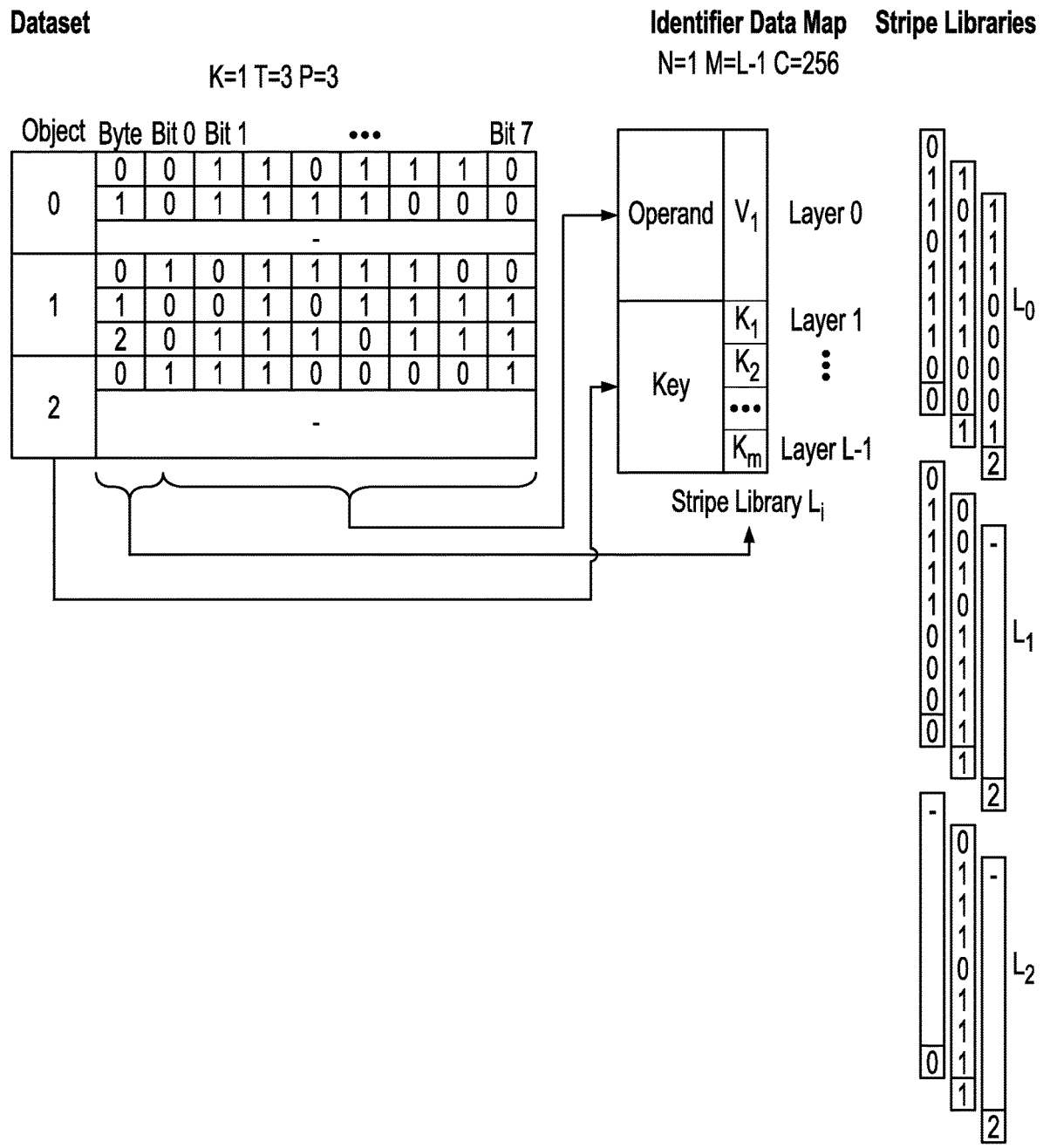
FIG. 18 shows a workflow for longitudinal encoding of a dataset across strip libraries, according to an illustrative implementation.

FIG. 18 shows an example workflow for longitudinal encoding of a dataset according to the rules described in the foregoing. A dataset (A) contains 3 data objects (D=3), each having an object-rank (0, 1, or 2) and at most 3 bytes (T=3). Data object 0 has 2 bytes (0, 1), data object 1 has 3 bytes (0, 1, 2), and data object 2 has 1 byte (0). The data objects are divided into 3 parts (P=3), each part comprising 1 byte-value (K=1)(P=$\lceil T/K \rceil$=$\lceil 3/1 \rceil$=3). An identifier data map (B) shows how identifiers used for chemically encoding this dataset each comprise an operand and a key. For each individual identifier, the key encodes an object rank (0, 1, or 2) of a respective data object, and the operand encodes the bit values of a given part of the respective data object. Stripe libraries (C) are identifiers grouped according to part-ranks, the position of the given part (and thus the corresponding byte-value) within the data object. In this example of FIG. 18, the first stripe library $L_0$ comprises three identifiers encoding the first parts of each data object. The second stripe library $L_1$ comprises three identifiers encoding the second parts of each data object. The third data object does not have a byte-value in the second part, so the special delimiter symbol "−" is shown in the operand. In some implementations, identifiers have a specific concatenation of components encoding the special delimiter, but alternatively identifiers having the special delimiter may be omitted from the library such that their absence from the library represents the lack of a byte-value for the corresponding part of the corresponding data object. The third stripe library $L_2$ comprises three identifiers encoding the third parts of each data object, where the identifiers for the first and third data objects do not have byte-values, so their operands shown the special delimiter symbol.

Longitudinal Filtering

Figure 19A:
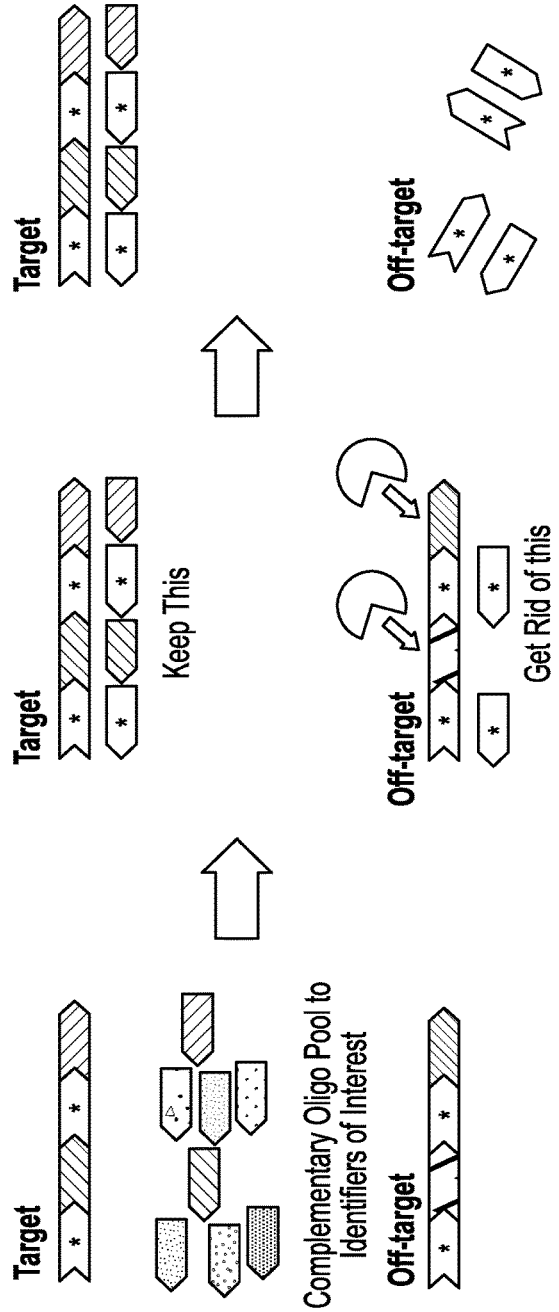
FIGS. 19A-19B shows a workflow for filtering a target library, according to an illustrative implementation.
Figure 19B:
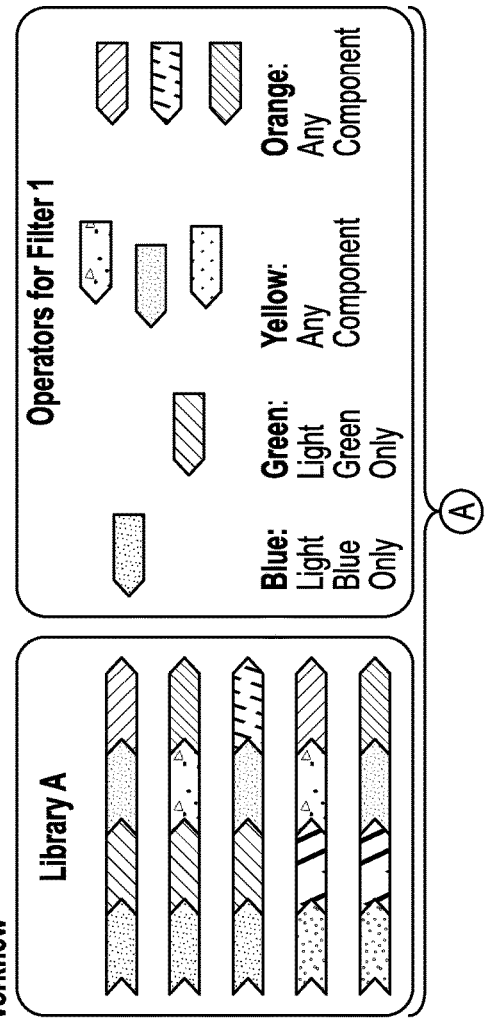
Figure 19B:
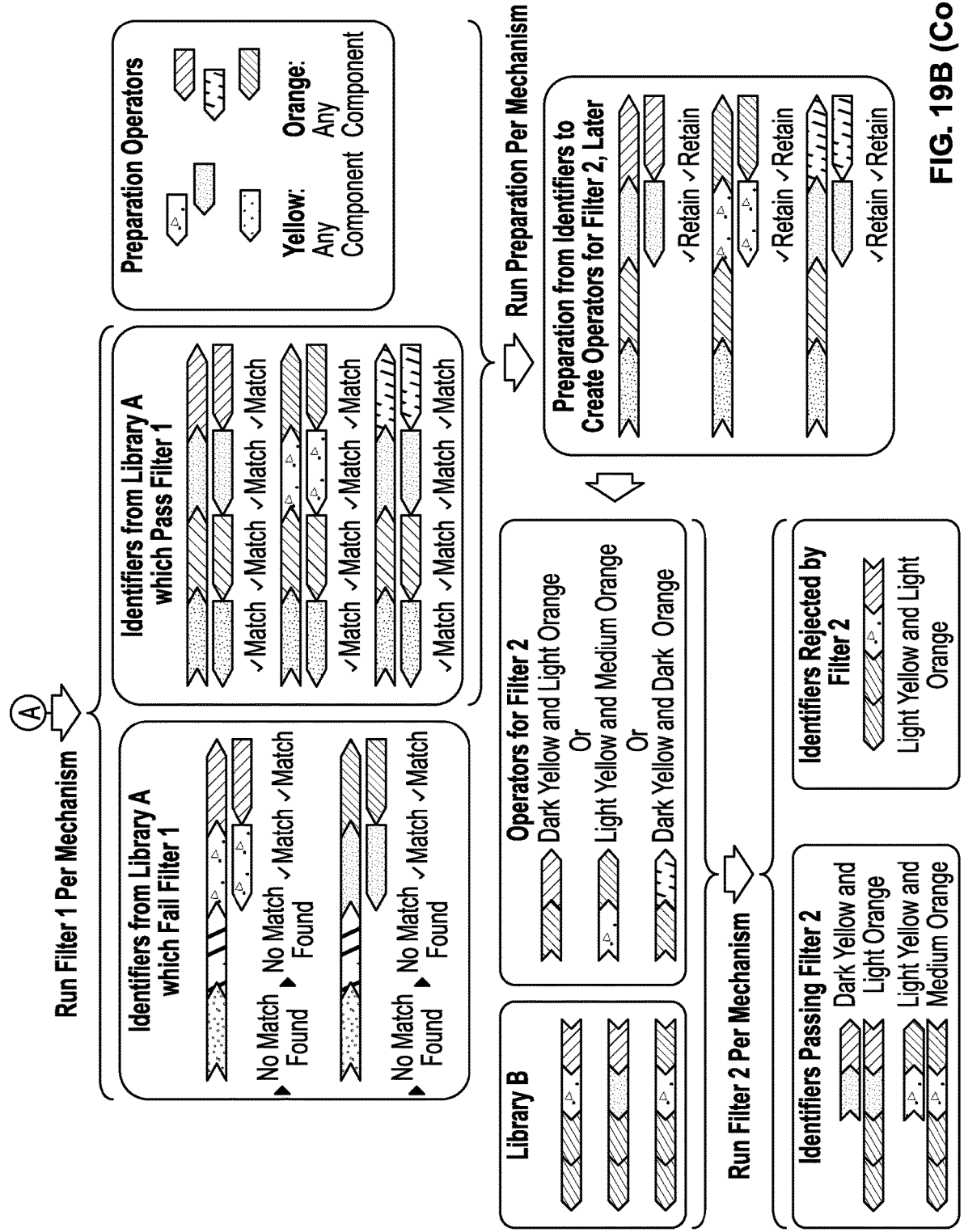

This aspect enables retrieval of any substripe of any subset of data objects, given any query substripe of the desired subset. An example of this retrieval method is shown in FIGS. 19A-19B. A dataset of D data objects is encoded with longitudinal striping over P identifier libraries. Each identifier is composed of M key layers and N operand layers, as described above. Suppose a query substripe X containing the i-th parts of some subset $S \subseteq \{1, \ldots, D\}$ of data objects is given, and we wish to retrieve the substripe Y containing the j-th parts of the same subset S of data objects. This retrieval operation, hereon referred to as filtering comprises two steps:
  1. Key extraction: The key layers of each identifier in query X are isolated from the operand layers of the identifier.
  2. Key matching: Identifiers from a target library $L_j$ whose key layers match the key layers isolated from X are selected and output as substripe Y.

In some implementations, key extraction is performed by first converting each identifier in X to a single-stranded form. The nucleic acids corresponding to all possible components that can occur in the key layers are obtained in a single stranded form complementary to that of X, and are hybridized to the single-stranded form of X. This ensures that the key layers are double-stranded whereas the operands layers are in single-stranded form. This mixture is subjected to a single-stranded DNA degrading nuclease such as P1 (as shown in FIG. 19A). This degrades the operand layers and retains the key layers of the substripe X in double-stranded form.

In some implementations, key extraction is performed by digesting each identifier in X with a restriction endonuclease that recognizes a specific sequence that is found in all identifiers between the key and operand layers, followed by size selection to retain the key layers of the substripe X in double-stranded form.

In some implementations, key extraction is performed by introducing a nick between the key and operand layers with a sequence-specific nicking enzyme, incorporating labeled nucleotides with DNA polymerase I at the nick site, melting the strands to produce single-stranded DNA, and performing affinity capture against the labeled nucleotides to retain the key layers of the substripe X in single-stranded form. In one implementation, the label may be biotin and affinity capture performed with streptavidin-coated beads.

In some implementations, key extraction is performed by selectively amplifying and purifying the key layers. Here, the identifiers are designed such that the key layers are flanked by universal sequences that serve as primer binding sites for PCR. The amplified DNA is purified to remove operand sequences, resulting in the retention of key layers of the substripe X in double-stranded form.

In some implementations, key matching is performed by first converting the target library $L_j$ and the keys extracted into complementary single-stranded forms. The nucleic acids corresponding to all possible components that can occur in the operand layers of the target library are obtained in single-stranded form complementary to that of the target library, and together with the single-stranded keys, are hybridized to the complementary single-stranded target library. This ensures that identifiers in the target library whose key layers match one of the extracted keys will be in double-stranded form, whereas an identifier whose key layers do not match any of the extracted keys will be in a partially single-stranded form. Its key layers will be partially or completely single stranded. This mixture is subjected to a single-stranded nucleic acid degrading nuclease such as P1. This degrades the key layers of non-matching identifiers in the target library, leaving only matching identifiers in their full-length double-stranded form (as shown in FIG. 19A). These identifiers may be further selected for their full-length using gel electrophoresis. Together, these chemical operations implement the filtering operation described above (as shown in the workflow of FIG. 19B).

In some implementations, key matching is performed by attaching affinity groups to the extracted key layers, where key layers are complementary to matching key layers in the target library, such that molecules of the target library hybridize to the key molecules and can be indirectly captured using affinity methods targeting those key molecules.

The full workflow shown in FIG. 19B comprises applying the Filter 1 operators to Library A comprising five identifiers. Each identifier in library A comprises four components selected from four layers. Filter operators represent a query. The Filter 1 operators select for one component in the first two layers and select any component form the last two layers. Running Filter 1, using any of the mechanisms described herein, on Library A gives identifiers which fail Filter 1 and identifiers which pass Filter 1. A preparation step is run to extract and retain the components of the last two layers of the identifiers which passed Filter 1 in order to obtain the operators for Filter 2. Library B is provided and contains three identifiers each having four components selected from four layers. The Filter 2 operators from the preparation step are applied to Library B to obtain identifiers passing Filter 2 and identifiers rejected by Filter 2.

Graph Programs for Longitudinally-Encoded Datasets

Figure 13C:
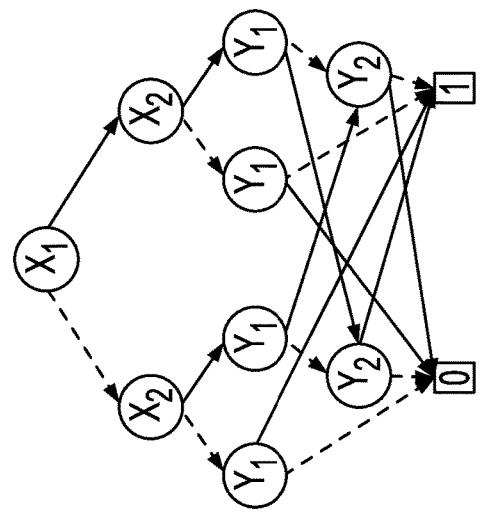
Figure 20:
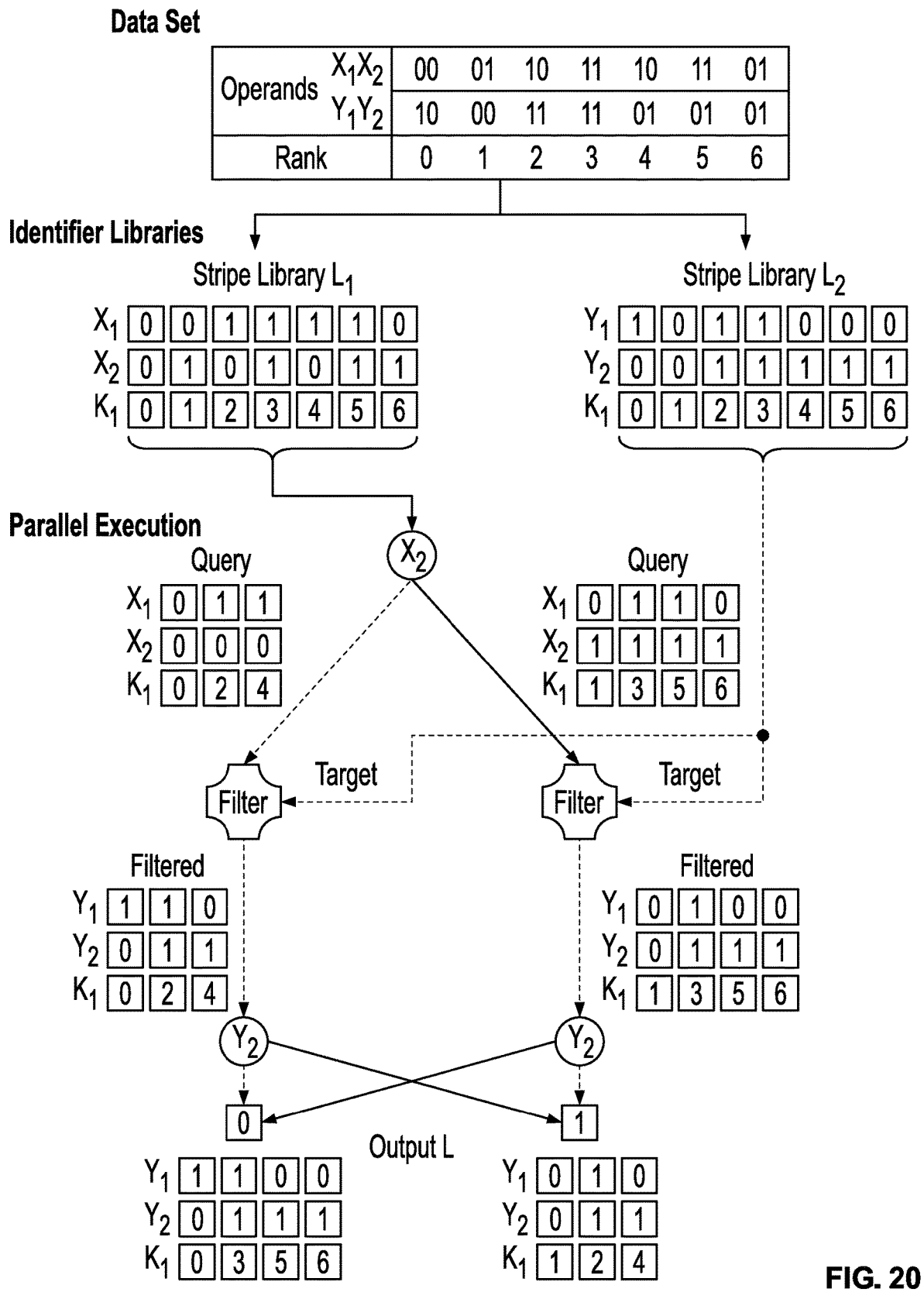
FIG. 20 shows a workflow for executing a program on a longitudinally-encoded dataset, according to an illustrative implementation.

The graph programming model described in the foregoing (see FIGS. 13A-14F) can be used to compute on a longitudinally striped input library. A graph program is a network of if-then-else (ITE) gates where each ITE gate takes as input a library of identifiers and produces as output a set of identifier libraries. Previously, graph programs execute a parallel computation on longitudinally encoded data. This was limited to a single input identifier library. The aspects described above allow graph programs to execute parallel computations on longitudinally striped data taking multiple stripes as input. Consider the example illustrated in FIGS. 13A-14F. To illustrate computation with longitudinally striped inputs, one of the three graph programs called "Output L" described in FIG. 13-14 is extended in FIG. 20. FIG. 20 shows the dataset (A) described previously comprising two integer operands X and Y. In this example, this dataset is longitudinally striped across two identifier libraries $L_1$ and $L_2$ with operand X stored in $L_1$ and operand Y stored in $L_2$ (identifier libraries B). The first ITE gate (C in FIG. 20) operates on a part of the X operand ($X_2$) and therefore, takes stripe $L_1$ as input. As described previously, the gate produces two output libraries, one where $X_2=0$ and another where $X_2=1$. Because this is a longitudinally striped dataset, these libraries cannot serve as input to the next ITE gate. Instead, these are used as query stripes to retrieve the necessary input stripe for the next ITE gates. Since the next layer of ITE gates operate on operand Y ($Y_2$), stripe $L_2$ is used as the target library for retrieval in the next ITE gate. Using these query and target libraries, the output libraries from the first ITE gate are translated into input libraries for the next layer of ITE gates. In this way, graph programs can use a longitudinally striped dataset for computation. In combination, the first ITE gate (a filter on operand $X_2$ of stripe $L_1$) and the second ITE gate (a filter on operand $Y_2$ using operators from filtered stripe $L_1$) produce an output library representing output L, where key ranks 1, 2, and 4 have value 1, and key ranks 0, 3, 5, and 6 have value 0, in accordance with the output in FIG. 13C.

Implementations

Provided below are example implementations of the various aspects described in the foregoing.

Partitioning Information Stored in Nucleic Acids

Figure 21:
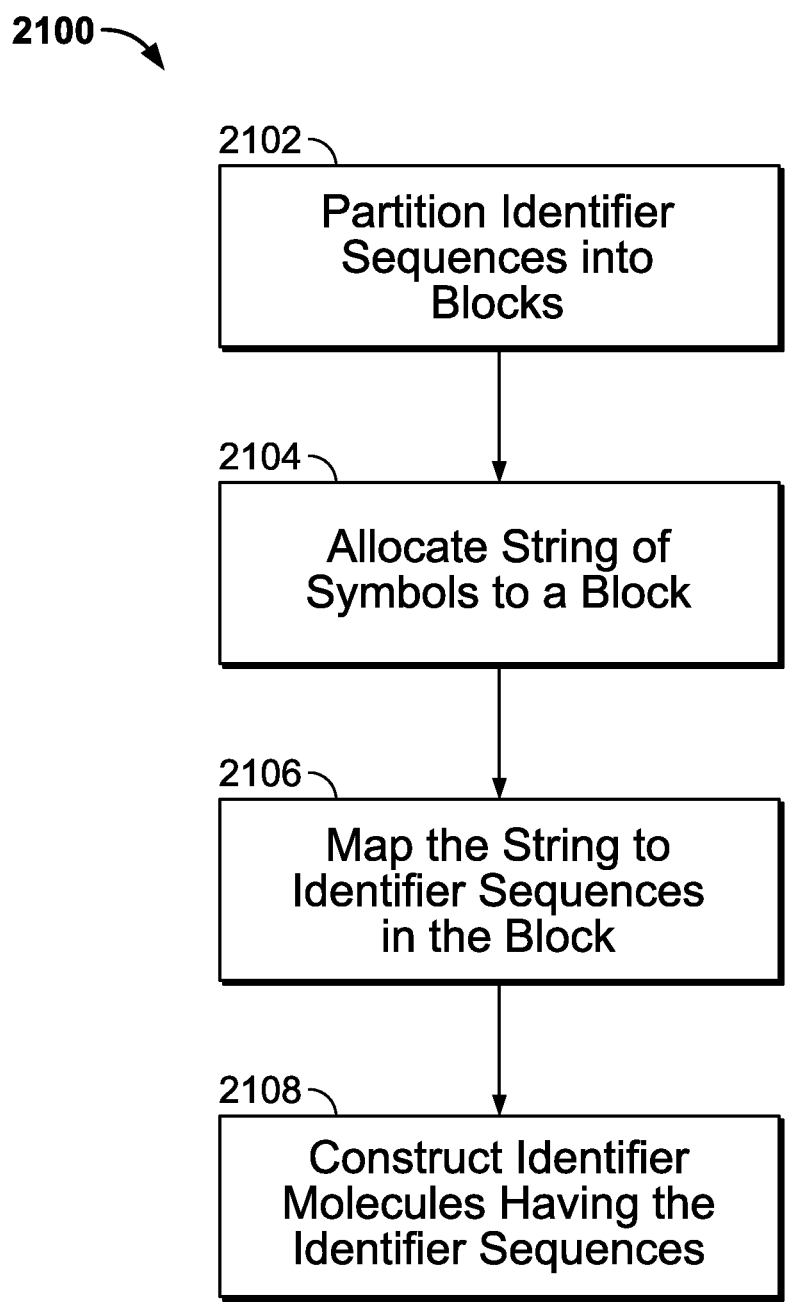
FIG. 21 shows a flowchart describing a method for storing digital information into nucleic acid molecules using partitions, according to an illustrative implementation.

As discussed in the foregoing, information stored in nucleic acids may be partitioned to provide for easier access and reading of said information. FIG. 21 is a flowchart describing a method 2100 for storing digital information into nucleic acid molecules using partitions. Method 2100 comprises steps 2102, 2104, 2106, and 2108. Step 2102 involves partitioning identifier nucleic acid sequences into blocks. Each identifier nucleic acid sequence comprises component nucleic acid sequences, at least a portion of which are configured to bind to one or more probes. Step 2104 involves allocating a string of symbols to a block of the blocks. Step 2106 involves mapping the string of symbols to a plurality of identifier nucleic acid sequences within the block. Step 2108 involves constructing individual identifier nucleic acid molecules of the plurality of identifier nucleic acid sequences (i.e., the constructed identifier nucleic acid molecules have sequences from the plurality of identifier nucleic acid sequences).

As described previously, mapping (in step 2108) may be performed using a codebook that maps words (portions of digital information to be encoded, such as the string of symbols) to codewords (groups of identifier nucleic acid sequences). Each block comprise one or more codewords. In some implementations, there is a fixed number of codewords per block. For example, a range of identifiers encoding the $g^{th}$ instance of a block can be calculated as the range encoding codeword instances (g−1)*c+1 through g*c.

In some implementations, a block can be accessed with an access program, such as those described in the foregoing. In some implementations, a block is associated with a location, said location comprising information for accessing said block. In some implementations, a block contains information about a location of another block.

In some implementations, a block represents a node in a graph. The graph may be a tree, such as a suffix tree or a B-tree. In some implementations, a block is an element of an inverted index. In some implementations, multiple blocks form a linked list, wherein a first block points to a second block to accommodate a large symbol of strings that is mapped to at least the first block and the second block.

In some implementations, the identifier sequences of each block share the same component sequences in a set of key layers. Said key layers may store a data object, such as a native key (as described in the foregoing). The native key comprises one or more symbols and may be configured such that each symbol corresponds to a component sequence of a corresponding key layer. The method may further comprise performing a range query over several keys sharing common symbol values at a set of positions by accessing all identifier molecules containing their corresponding component sequences. A query for all keys that satisfy a finite automata or regular expression may be performed by an access program.

The method may further comprise storing a value in the identifier sequences of the block associated with each key. Said value may be retrieved by accessing the corresponding key. The key may be a function of the value. The key may be a hash (e.g., a hashed value resulting from applying a hash function to the value), a bloom filter, a structural array, a classifier, a signature, a record, or a fingerprint derived from the corresponding value. An access program may be designed to access all keys that are similar to, or share symbol values in common with, a query key. Said query key may be derived from a reference value.

A count of a number of keys (e.g., across all the blocks or identifier molecules) may be determined by measuring DNA concentration. For example, DNA concentration may be measured by fluorescence (e.g., qPCR, plate reader assay, Qubit fluorimeter) or by absorbance (e.g., spectrophotometry assay). The measured DNA concentration may be normalized by a standard to determine the number of identifier sequences in a sample. A relative number of keys containing a particular symbol may be determined by performing qPCR with a probe for a key layer component corresponding to the particular symbol.

In some implementations, the method further comprises creating an identifier sequence for a reference key. Said reference key may be used for performing a query. The identifier sequence may be used as a hybridization probe in a hybridization reaction to search for or extract all keys that are similar or the same. Conditions, such as pH or temperature, of the hybridization reaction may be used to control the stringency of the search or extraction. For example, adjusting temperature allows for control of how similar the keys must be to the reference key in order to be accepted.

Operating on Information Stored in Nucleic Acids

Figure 22:
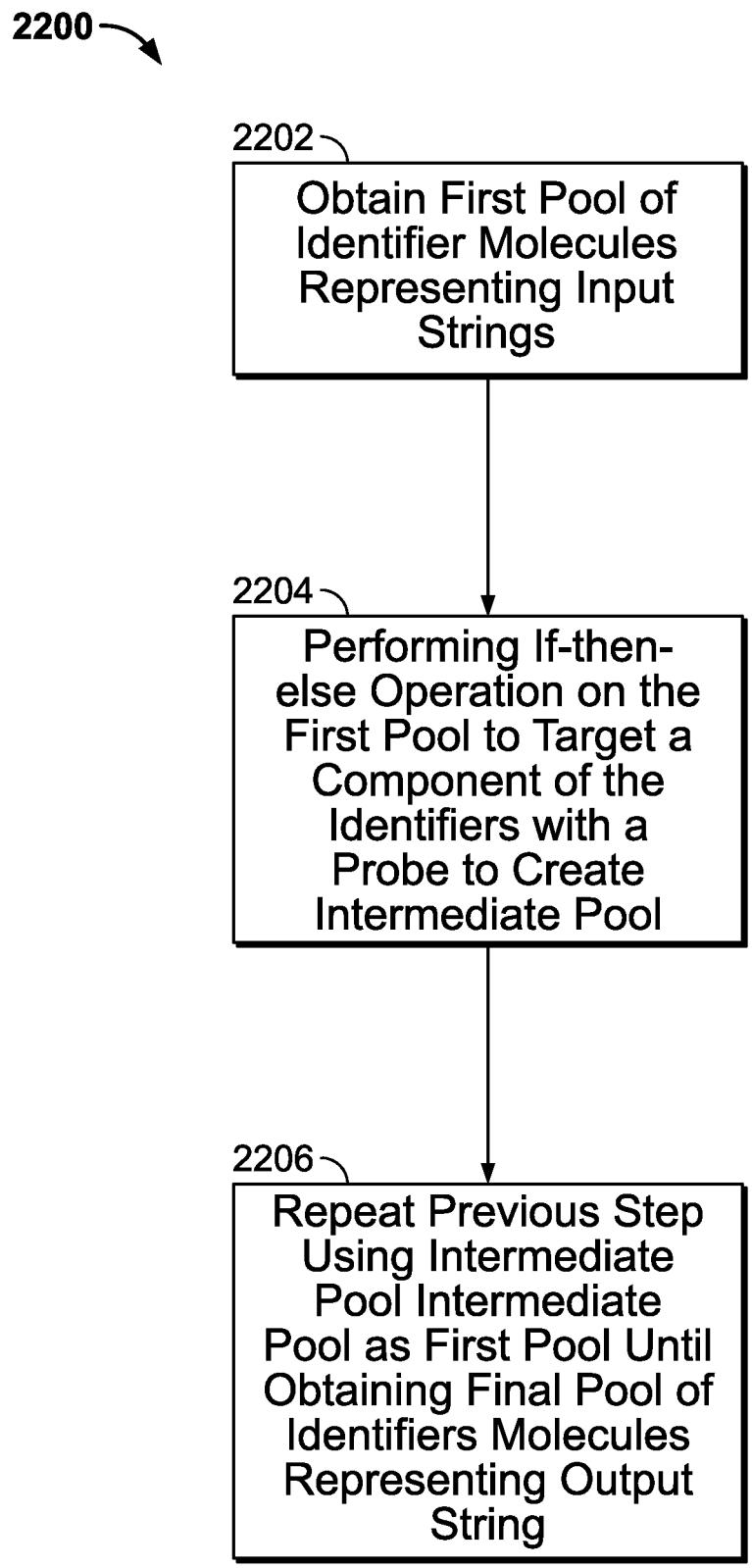
FIG. 22 shows a flowchart describing a method for operating on digital information stored in nucleic acid molecules, according to an illustrative implementation.

As discussed in the foregoing, information stored in nucleic acids may be used for computation by applying if-then-else (ITE) gates to select for certain values, symbols, or sequences. FIG. 22 shows a flowchart describing a method 2200 for operating on digital information stored in nucleic acid molecules. Method 2200 comprises steps 2202, 2204, and 2206. Step 2202 involves obtaining a first pool of identifier molecules (nucleic acids). The pool has a powder, liquid, or solid form. Each identifier molecule in the first pool comprises component molecules, at least a portion of which are configured to bind to one or more probes. The identifier molecules represent one or more input strings of symbols. Step 2204 screening the identifier nucleic acid molecules in the first pool by targeting at least one of the component nucleic acid molecules with a probe, to create an intermediate pool comprising a subset of identifier nucleic acid molecules from said first pool. The intermediate pool represents a result of an if-then-else operation performed on the input strings. Step 2204 results in the creation of an intermediate pool with a subset of identifier molecules from said first pool. Step 2206 involves repeating step 2204, such that the intermediate pool replaces the first pool at every subsequent step (undergoing an if-then-else operation), until a final pool of identifier molecules is created. The final pool represents at least a portion of an output string of symbols.

In some implementations, each identifier molecule in the first pool comprises a distinct component sequence from each of M layers. Each layer comprises a set of component sequences.

In some implementations, an identifier molecule represents a data object. A component molecule of the identifier molecule may represent an operand of the data object. In some implementations, the if-then-else operation comprises using a probe pool of identifier molecules having a specific component molecule as probes, for example, to select for identifier molecules in the first pool having the same specific component molecule. For example, the identifier molecules of the probe pool are single-stranded and at least partially hybridize to single-stranded identifier molecules in the first pool which contain the same specific component molecule. In some implementations, the probes are PCR primers, and the if-then-else operation is executed with PCR. In some implementations, the probes are affinity tagged oligonucleotides, and the if-then-else operation is executed with an affinity pull down assay.

In some implementations, two or more if-then-else operations are performed on one or more pools of identifier molecules in parallel. In some implementations, method 2200 further comprises splitting at least one of the first pool, the intermediate pool, or the final pool into at least two duplicate pools. The at least one of the first pool, the intermediate pool, or the final pool may be replicated (e.g., by PCR) prior to splitting. Method 2200 may further comprise combining at least two intermediate pools of identifier molecules to form a new intermediate pool of identifier molecules or a second pool of identifier molecules.

In some implementations, the if-then-else operation (or repeated application thereof via step 2206) represents execution of a graph program, the output of which places an identifier molecule, representing a data object, into the final pool representing the at least a portion of the output string (e.g., the outputted identifier represents a bit of the output string). Said graph program may represent a function on said data object. The at least a portion of the output string may be an output of the function on the data object. In some implementations, the final pool to which an identifier molecule is placed into, according to the graph program, determines the output of the function on the corresponding data object encoded by the identifier molecule.

Storing Numerical Data in Nucleic Acids

Figure 23:
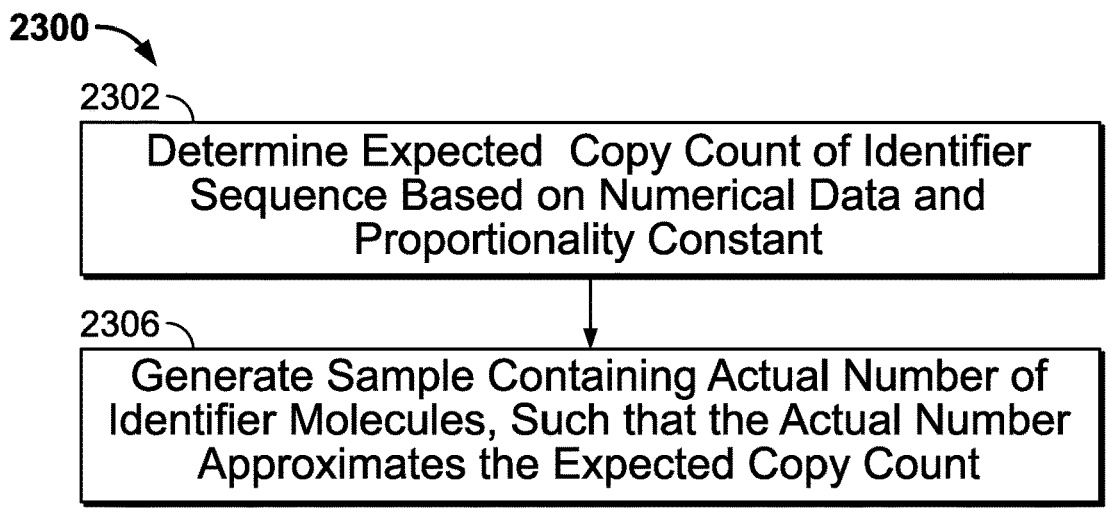
FIG. 23 shows a flowchart describing a method for storing numerical data in nucleic acids, according to an illustrative implementation.

As discussed in the foregoing, numerical data may be stored in identifier molecules by generating an expected copy count. FIG. 23 shows a flowchart describing a method 2300 for storing numerical data in nucleic acids. Method 2300 comprises steps 2302 and 2304. Step 2302 involves determining an expected copy count of an identifier nucleic acid sequence based on the numerical data and a proportionality constant. Step 2304 involves generating a sample containing an actual number of identifier nucleic acid molecules each having the identifier nucleic acid sequence, wherein the actual number approximates the expected copy count. The numerical data may be a number, and the expected copy count is proportional to the number by the proportionality constant. At least a portion of each identifier nucleic acid molecules may be configured to bind to one or more probes.

Method 2300 may further comprise inputting the sample to an operation to produce an output sample. For example, the operation may involve multiplying the number by a power of 2 by performing a polymerase chain reaction (PCR) with primers that bind to common regions on an edge of the identifier nucleic acid sequence to form the output sample containing a PCR product. The power of 2 may correspond to the number of PCR cycles performed. The operation may involve adding the number as a first number to a second number in a second input sample by a mixing operation that combines the sample and the second input sample to form the output sample. The output sample may be input to a second operation.

In some implementations, the number is a first element of a vector. Method 2300 may further comprise determining a second expected copy count of the identifier nucleic acid sequence based on a second element of the vector and the proportionality constant. Method 2300 may then further comprise generating a second sample containing a second actual number of identifier nucleic acid molecules each having the identifier nucleic acid sequence, wherein the second actual number approximates the second expected copy count.

Method 2300 may further comprise performing a linear function on the vector by at least one of PCR, aliquoting, and mixing. The linear function may be used to convert a binary vector to a unary value in an output sample. The linear function may be a scoring function. For example, the scoring function may compute a higher output value for target vectors than for non-target vectors, such that copy counts for identifier sequences corresponding to target vectors are enriched in the output sample. Identifier sequences corresponding to target vectors may be determined by sequencing the output sample. The ratio of copy counts between two identifier sequences in the output sample may be increased by using a double-stranded DNA selection operation to form a new output sample where identifier sequences corresponding to target vectors are even more enriched in the output sample. The operation (or repeated application thereof) may correspond to an activation function in a neural network or a quadratic function. In some implementations, the output sample is allowed to reach equilibrium prior to the double stranded DNA selection operation. Also prior to the operation, the temperature may be changed, or cofactors may be added to the output sample. The operation may be performed by at least one of chromatography, gel electrophoresis, mass spectrometry, flow cytometry, fluorescent-activated sorting, membrane capture, silica column capture, silica bead capture, or affinity capture.

In some implementations, the vector is a compressed representation of a larger data object (larger than the vector). The compressed representation may be a hash, a bloom filter, a signature, a structural array, or a fingerprint of the larger data object. The larger data object may be retrieved using the corresponding identifier nucleic acid sequence as a key.

Preparing Stripe Libraries Encoding a Dataset

Figure 24:
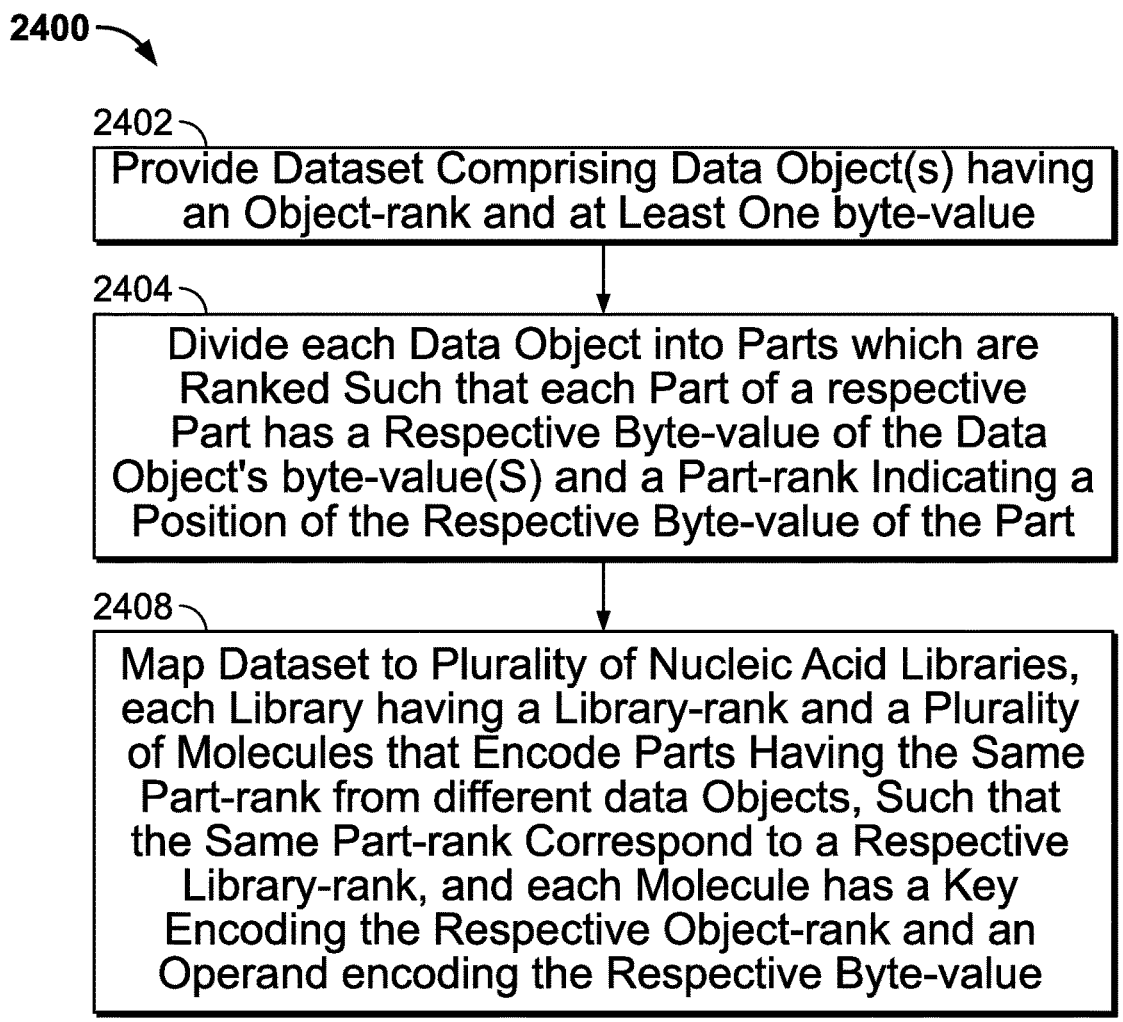
FIG. 24 shows a flowchart describing a method for preparing a plurality of nucleic acid libraries encoding a dataset, according to an illustrative implementation.

As discussed in the foregoing, a dataset may be encoded by division into parts and encoding of its parts across stripe libraries. FIG. 24 shows a flowchart describing a method 2400 for preparing a plurality of nucleic acid libraries encoding a dataset. Method 2400 comprises steps 2402, 2404, and 2406. Step 2402 involves providing a dataset comprising at least one data object, each data object having an object-rank and comprising at least one byte-value. Step 2404 involves dividing each data object into a plurality of parts. The plurality of parts is ranked such that each part of a respective data object comprises (1) a respective byte-value of the at least one byte-value from the corresponding data object of the part, and (2) a part-rank indicating a position of the respective byte-value of the at least one byte-value of the corresponding data object of the part. Step 2406 involves mapping the dataset to a plurality of nucleic acid libraries having a solid, liquid, or powder form. Each nucleic acid library has a library-rank and comprises a plurality of nucleic acid molecules that encode parts having the same part-rank from different data objects. Said same-part rank for the plurality of nucleic acid molecules of a given library corresponds to a respective library-rank of the given library. Each nucleic acid molecule comprises a key encoding the respective object-rank and an operand encoding the respective byte-value.

In some implementations, each nucleic acid molecule comprises L components, each component selected from C possible components of a distinct layer of L layers. M of the L components encode the key, and N of the L components encode the operand, such that the sum of M and N is less than or equal to L. The byte-value of the part encoded by each nucleic acid molecule may be stored in the operand of the nucleic acid molecule. In some implementations, each part contains no more than K byte-values, and each data object comprises at most T byte-values, such that each data object is divided into at most P parts, where P=[T/K]. K may be any value less than $L*[\log_2 C]/8$.

In some implementations, the dataset is encoded using W nucleic acid libraries, each library containing nucleic acid molecules having an identifier rank of 1, . . . , R. The dataset comprises D data objects, such that R is greater than or equal to D. A rule may be that the $j^{th}$ part of the P parts of the $r^{th}$ data object of the D data objects is encoded in the operand of a nucleic acid molecule of rank in the interval $[C^N r, C^N(r+1)-1]$ in the $j^{th}$ library.

Also provided herein is a method of retrieving a subset of a data object of a dataset encoded in a plurality of nucleic acid libraries according to method 2400. This method comprises providing a target nucleic acid library and a query nucleic acid library, each comprising nucleic acid molecules each comprising a key and an operand. The method then involves extracting keys from nucleic acid molecules in the query nucleic acid library. The method then involves matching nucleic acid molecules in the target nucleic acid library having keys that match the keys extracted from the query nucleic acid library. Finally, the method involves selecting and outputting the matched nucleic acid molecules.

The extraction step may comprise converting each nucleic acid molecules in the query library to a single-stranded molecule, and match may comprise hybridizing nucleic acid molecules in the target library to complementary single-stranded keys. Selecting may comprise applying an enzyme that selectively degrades single-stranded nucleic acids after the hybridization. For example, the enzyme may be P1.

The extraction step may comprise digesting each nucleic acid molecule in the query library using a sequence-specific enzyme that recognizes the specific sequence found in each nucleic acid molecule. This extraction may further comprise size-selecting keys present in double-stranded form.

The extraction step may comprise introducing a nick between the key and the operand of each molecule using a sequence-specific nicking enzyme, incorporating a labeled nucleotide at the nick, and capturing the labeled nucleotides to retain keys in a single-stranded form. For example, the labeled nucleotide has a biotin label, and capturing involves affinity capture with streptavidin-coated beads.

The extraction step may comprise selectively amplifying via PCR and purifying the keys from the query library, the keys being flanked by universal sequences that serve as primer binding sites for the PCR.

Matching may involve converting the target library and extracted keys to single-stranded forms and hybridizing single-stranded extracted keys to complementary keys in the target library. Selecting may involve gel electrophoresis.

In some implementations, the query library encodes a first set of parts of the dataset, and the target library encodes a second set of parts of the dataset (e.g., according to method 2400 of FIG. 24). The extraction step may act as a first if-then-else operation on the dataset, and the matching step and selection/output step act as a second if-then-else operation on the dataset.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in nucleic acid-based data storage, may be applied to applications involving data archival and storage or chemical data science.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

The systems and methods described may be implemented locally printer-finisher system, such as that described in U.S. application Ser. No. 16/414,752 entitled "PRINTER-FINISHER SYSTEM FOR DATA STORAGE IN DNA", filed May 16, 2019 and published as U.S. Publication No. 2019/0351673, which is hereby incorporated by reference in its entirety. The printer-finisher system may include a data processing apparatus. The systems and methods described herein may be implemented remotely on a separate data processing apparatus. The separate data processing apparatus may be connected directly or indirectly to the printer-finisher system through cloud applications. The printer-finisher system may communicate with the separate data processing apparatus in real-time (or near real-time).

In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method for operating on digital information stored in nucleic acid molecules, the method comprising:
   (a) obtaining a first pool of identifier nucleic acid molecules, the identifier nucleic acid molecules representing input strings of symbols, the pool having powder, liquid, or solid form, each identifier nucleic acid molecule in the first pool comprising component nucleic acid molecules, at least a portion of which are configured to bind to one or more probes;
   (b) performing an if-then-else operation on the input strings by applying a probe to the identifier nucleic acid molecules in the first pool, the probe configured to target at least one of the component nucleic acid molecules to create an intermediate pool comprising a subset of identifier nucleic acid molecules from said first pool; and
   (c) repeating step (b) until a final pool of identifier nucleic acid molecules is created that represents at least a portion of an output string of symbols, wherein at each subsequent step (b) the if-then-else operation is performed on the intermediate pool from the previous step.

2. The method of claim 1, wherein each identifier nucleic acid molecule in the first pool comprises a distinct component nucleic acid sequence from each of M layers, wherein each layer comprises a set of component nucleic acid sequences.

3. The method of claim 1, wherein each identifier nucleic acid molecule represents a data object.

4. The method of claim 3, wherein a component nucleic acid sequence of the identifier nucleic acid molecule represents an operand of the data object.

5. The method of claim 3, wherein the probe comprises identifier nucleic acid molecules in a pool that includes a specific component nucleic acid molecule.

6. The method of claim 3, wherein the probe is a polymerase chain reaction (PCR) primer, and the if-then-else operation is executed with PCR.

7. The method of claim 3, wherein the probe is an affinity tagged oligonucleotide, and the if-then-else operation is executed with an affinity pull down assay.

8. The method of claim 3, wherein two or more screening steps are performed on one or more pools of identifier nucleic acid molecules in parallel.

9. The method of claim 3, further comprising splitting at least one of the first pool, the intermediate pool, or the final pool into at least two duplicate pools.

10. The method of claim 9, further comprising replicating the at least one of the first pool, the intermediate pool, or the final pool prior to splitting.

11. The method of claim 10, wherein the replicating is executed with polymerase chain reaction (PCR).

12. The method of claim 9, further comprising combining at least two intermediate pools of identifier nucleic acid molecules to form a new intermediate pool of identifier nucleic acid molecules or a second pool of identifier nucleic acid molecules.

13. The method of claim 1, wherein the repetition of step (b) in (c) represents execution a graph program, the output of which places an identifier nucleic acid molecule, representing a data object, into the final pool representing the at least a portion of the output string.

14. The method of claim 13, wherein said graph program represents a function on said data object.

15. The method of claim 14, wherein the at least a portion of the output string is an output of the function on the data object.

16. The method of claim 15, wherein the final pool to which an identifier nucleic acid molecule is placed into, according to the graph program, determines the output of the function on the corresponding data object.

* * * * *